(12) United States Patent
Chu et al.

(10) Patent No.: US 6,177,417 B1
(45) Date of Patent: Jan. 23, 2001

(54) CHOLANIC ACID RING BASED 4-(TRIFLUOROACETYL)PHENYL DERIVATIVES, PROCESS FOR PREPARATION AND USE THEREOF

(75) Inventors: Junho Chu, Seoul; Hyung Jung Pyun, #106-507 Woosung Apt., 400 Gil-dong, Kangdong-ku, Seoul 134-011; In Jun Yoon, Seoul; Jae Ho Shin, Seoul; Hakhyun Nam, Seoul; Geun Sig Cha, #4-207 Cheongwoon Apt., San 4-25, Cheongwoon-dong, Chongro-ku, Seoul 110-030, all of (KR)

(73) Assignees: Hyung Jung Pyun; Geun Sig Cha, both of (KR)

( * ) Notice: Under 35 U.S.C. 154(b), the term of this patent shall be extended for 0 days.

(21) Appl. No.: 09/338,028

(22) Filed: Jun. 22, 1999

(30) Foreign Application Priority Data

Jul. 9, 1998 (KR) .................................. 98-27564

(51) Int. Cl.[7] .............................. A61K 31/56; C07J 9/00
(52) U.S. Cl. ..................... 514/179; 514/169; 514/182; 552/502; 552/526; 552/538; 552/540; 552/548; 552/550
(58) Field of Search ..................................... 552/502, 526, 552/538, 550, 540, 548; 514/169, 179, 182

(56) References Cited

PUBLICATIONS

Davis et al; Journal of Chemical Society, Chem.Commun., p. 1050, 1989.*

Maitra et al; Journal of Organic Chemistry, vol. 61, p. 9494, 1996.*

1993 Analytical Chemistry, 65, pp. 3151–3155, entitled Asymmetric Carbonate Ion–Selective Cellulose Acetate . . . , By Kang Shin Lee et al.

1996 Journal of Organic Chemistry, 61, pp. 9494–9502, entitled Design, Synthesis, and Evaluation of Bile Acid–Based Molecular . . . , By D'Souza et al.

* cited by examiner

*Primary Examiner*—Sreeni Padmanabhan
(74) *Attorney, Agent, or Firm*—Bachman & LaPointe, P.C.

(57) ABSTRACT

The present invention relates to a cholanic acid ring based 4-(trifluoroacetyl)phenyl derivatives of the following formula 1, process for preparation and use thereof. The cholanic acid ring based 4-(trifluoroacetyl)phenyl derivatives of the present invention may be used as a host material in the host-guest chemistry, in detail as a material for ion sensors, optical sensors, gas sensors, biosensors, chromatographies, photostimulated ion-binding resins, ion exchange resins and organic reactions.

FORMULA 1

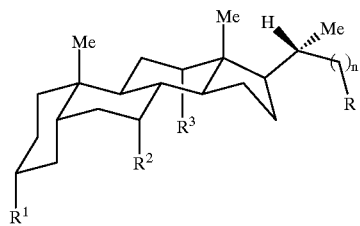

(In the above formula 1, R, $R^1$, $R^2$, $R^3$ and n are defined in the specifications).

18 Claims, 14 Drawing Sheets

CHOLANIC ACID RING BASED 4-(TRIFLUOROACETYL)PHENYL DERIVATIVES, PROCESS FOR PREPARATION AND USE THEREOF

BACKGROUND OF THE INVENTION

The present invention relates to cholanic acid ring based 4-(trifluoroacetyl)phenyl derivatives of the following formula 1, process for preparation thereof and use thereof as host materials in the host-guest chemistry.

FORMULA 1

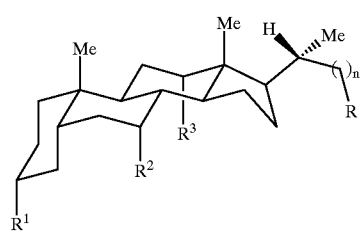

In formula 1, n is a value representing the length of an alkyl chain and is 0–3;

R represents alkyl($C_1$–$C_{20}$), alkoxy($C_1$–$C_{20}$) methyl, alkoxy($C_1$–$C_{20}$) carbonyl, dialkyl($C_1$–$C_{20}$) amide, dialkyl ($C_1$–$C_{20}$) ethylene or diphenylethylene;

$R^1$ and $R^3$ represent acetoxy or 4-trifluoroacetyibenzoxy; and $R^2$ represents hydrogen, keto, acetoxy or 4-trifluoroacetylbenzoxy.

In the last twenty years there has been extensive development in the supramolecular chemistry, and in recent years supramolecules are applied in various and complex ways.

The supramolecules, obtained from natural sources or synthesized by introduction of various functional groups in a molecule, can be used diversely in the host-guest chemistry. The host-guest chemistry is a field to study the interaction of ions or molecules with a compound having several functional groups or an empty site in the molecule. It has attracted a good deal of attention and has been actively studied since Morf et al. had reported that most of the ionophores in nature, which usually act as antibiotics, tend to transport cations selectively across biomembrane (Helv. Chim. Acta 1971, 54, 268).

The supramolecules in the host-guest chemistry are designed by suitably arranging functional groups stereospecifically to bind a guest molecule selectively, so that it is possible to recognize a guest molecule energetically and/or stereospecifically by intermolecular interactions. The scope of guest molecules is also extended to ion species as well as neutral molecules. The compounds such as crown ethers, podants, cryptands and spherands are used as representative ion-selective hosts which can quantify specific ions in ion-selective electrodes and optical sensors, and as ion-selective membranes acting as signal transducer in biosensors and gas sensors.

The steroid-type molecules can be used as primary skeleton for application to the supramolecular chemistry and the host-guest chemistry in considering the aforesaid size, chirality and multiple ring fixed structurally. In particular, the bile acid-type molecules have been actively studied since those are readily available and it is possible to control the extend of introduction of functional groups. The examples of the above bile acid-type molecules are shown below.

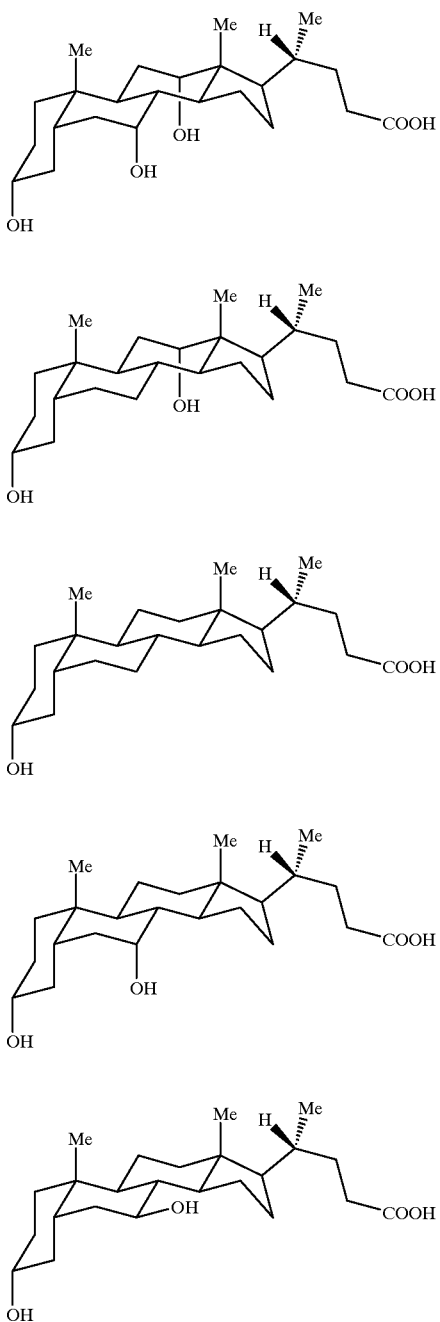

As represented below, the applicability of the above molecules has been studied recently for a host molecule of carbohydrate, wherein a cholaphane having a cavity in a supramolecule was synthesized by connecting the two units of cholic acid, one of bile acids, by two benzyl linkers (A. P. Davis, R. P. Bonar-law, *J. Chem. Soc.*, Chem. Commun., 1989, 1050).

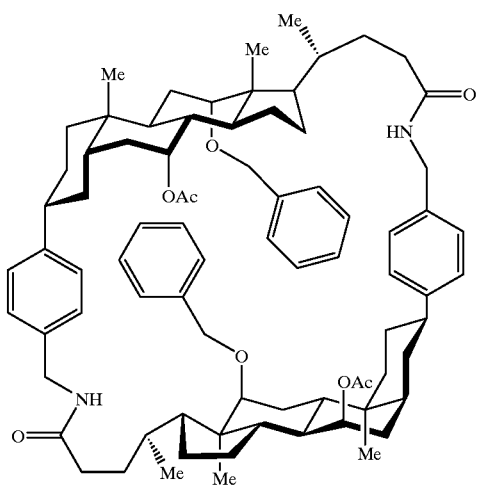

In addition, the host molecules shown below have been reported as molecular tweezers, in which the two pyrene groups were introduced into cholic, ketocholic, and deoxycholic acid esters, and the resultant host molecules can interact with an aromatic molecule (U. Maitra, *J. Org. Chem.*, 1996, 61, 9494).

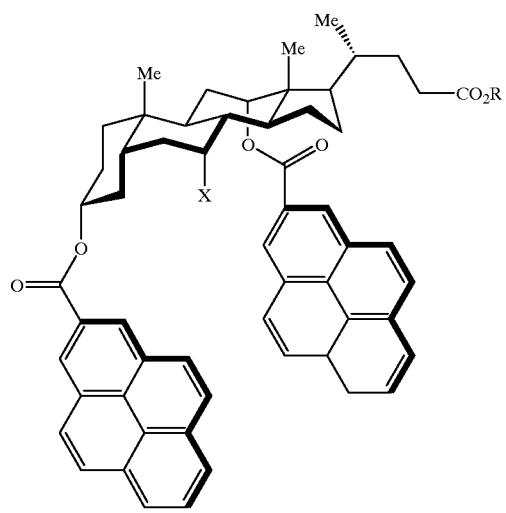

Cholic acid, one of bile acids, is characterized by containing a rigid steroidal ring structure and having the 3α-, 7α- and 12α-hydroxyl groups arranged nearly perpendicularly to the one side of the ring plane. In considering the proposed mechanism that two molecules of 4-(trifluoroacetyl)phenyl derivatives interact with a carbonate anion as represented below, the above properties have advantages that more than two 4-(trifluoroacetyl)benzoxy groups can be introduced into the one side of the molecule. That is, the binding of a carbonate anion to one 4-(trifluoroacetyl)benzoxy group could enhance the binding of the other 4-(trifluoroacetyl)benzoxy group in the same molecule.

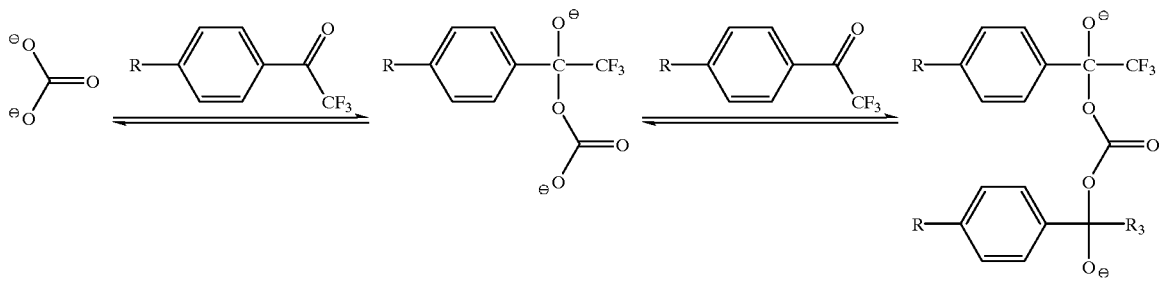

The distances between 3- and 7-, 7- and 12-, and 3- and 12-hydroxyl groups are expected to be 4.9 Å, 4.6 Å, and 6.2 Å, respectively. Since the distances between the two hydroxyl groups are similar to, or a little larger than the size of carbonate anion (4.8 Å), it is expected that compounds with two or more 4-(trifluoroacetyl)benzoxy groups at hydroxyl groups in cholanic acid derivatives can exhibit an excellent property as hosts of carbonate anion.

A representative usage of ionophores is an ion sensor. An ion-selective membrane electrode, one of ion sensors, measures the potential difference generated by a charge separation between layers formed on membrane surface when a specific ion or a molecule binds to ionophores in the ion-selective membrane attached in the electrode. This electrode has advantages of an excellent selectivity for specific ions, a short analysis time and a low cost, and therefore it has been used for measuring ion species in the food chemistry, the fermentation process, the environmental chemistry and the clinical chemistry such as a hemodialysis, a blood electrolyte continuous autoanalysis, and an extracorporeal blood, owing to the development during the last 30 years. In particular, ion-selective membrane electrodes have been successfully applied to analysis of electrolyte ions such as potassium ion, sodium ion, calcium ion, carbonate ion and chloride ion in biological sample analysis by using various neutral carriers, as ionophores, which can bind selectively to specific ions.

An ion-selective membrane electrode can be classified into a conventional ion-selective membrane electrode and a solid-state ion-selective membrane electrode. The former has an inner reference filling solution between an ion-selective membrane and an inner reference metal electrode, and the latter needs not an inner reference filling solution (See FIG. 1a and FIG. 1b).

The general composition of ion-selective membranes attached in the electrode comprises a polymer as a matrix, an ionophore which binds with a specific ion to separate charge and a plasticizer of a non-volatile organic solvent, and may contain lipophilic additives further according to the type of ion-selective membrane.

p-Decyl-$\alpha,\alpha,\alpha$-trifluoroacetophenone (hereinafter, referred to as "TFADB"), one of 4-(trifluoroacetyl)phenyl derivatives has been most extensively used as an ionophore of carbonate ion-selective membrane electrode. However, there is a limit for the selective detection of carbonate ion because the response to lipophilic anions such as salicylate is higher than to carbonate ion in biological sample analysis (See FIG. 2a). In the case of the serum of patient administered a lot of aspirin, particularly, the interference of salicylate ion is known to be very serious. There have been several studies for removing the interference of salicylate ion, such as the method of inserting an error code to induce the measurement by a different analysis tool in the case of a serious interference of salicylate ion detected and the method of adding anion-binding complexone into buffer solution to precipitate salicylate ion, suggested by Scott et al. (W. J. Scott, E. Chapoteau, A. Kumar, *Clin. Chem.*, 1986, 32, 137). However, these methods are just a pretreatment of sample and cannot remove the interference essentially. Recently, as another method, Lee et al. have developed the method of reducing the interference of salicylate ion by using the asymmetric carbonate ion-selective membrane electrode having a hydrophilic membrane introduced into the carbonate ion-selective membrane (K. S. Lee, J. H. Shin, S. H. Han, G. S. Cha, D. S. Shin, H. D. Kim, *Anal. Chem.*, 1993, 65, 3151). However, the said method also doesn't change the selectivity of carbonate ion-selective membrane and has a disadvantage of difficulty in the construction of a membrane electrode because of a bilayer membrane structure. Therefore in order to remove or reduce the interference of salicylate ion essentially, the ionophore interacting directly with ions in membrane has to be substituted by a material having the excellent selectivity for carbonate ion.

We, the inventors of this invention, have investigated the improvement of ionophores used in an ion-selective membrane electrode and a biosensor, and have synthesized cholanic acid ring based 4-(trifluoroacetyl)phenyl derivatives. These materials can be used as host materials in the host-guest chemistry, and particularly they have an excellent selectivity for carbonate ion, so that the said derivatives can be widely used in -ion sensors, optical sensors, gas sensors, biosensors, chromatographies, photostimulated ion binding resins, ion exchange resins, and organic reactions.

SUMMARY OF THE INVENTION

The present invention provides cholanic acid ring based 4-(trifluoroacetyl)phenyl derivatives of the above formula 1.

The present invention provides preparation methods of cholanic acid ring based 4-(trifluoroacetyl)phenyl derivatives.

The present invention provides compositions for host materials comprising cholanic acid ring based 4-(trifluoroacetyl)phenyl derivatives.

The present invention provides uses of a cholanic acid ring based 4-(trifluoroacetyl)phenyl derivatives having an excellent selectivity for a carbonate ion, particularly as a host material in the host-guest chemistry, and in analysis of carbonate ion in a biological or an environmental sample, and uses in ion sensors, optical sensors, gas sensor, biosensors, chromatographies, photostimulated ion-binding resins, ion exchange resins, and organic reactions.

EXPLANATION OF SYMBOLS IN THE FIGURES

Figure 1A:
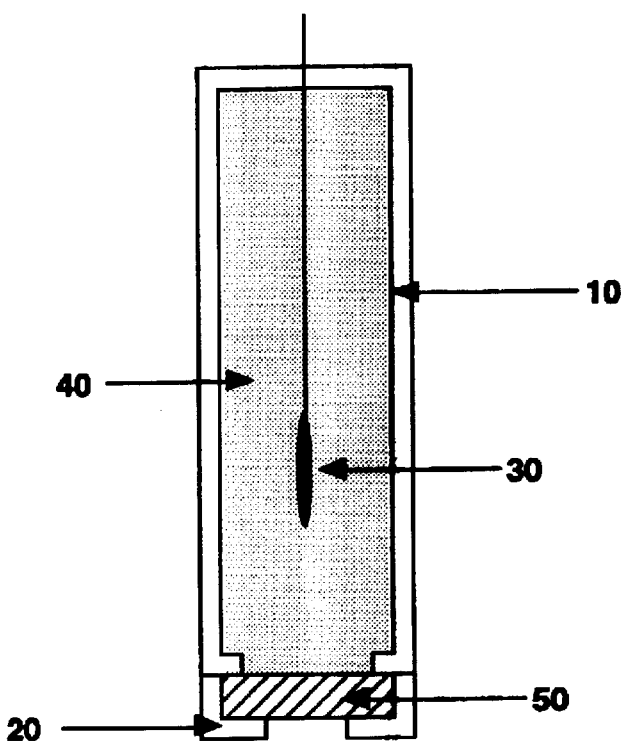
FIG. 1a depicts a schematic view of a conventional ion-selective membrane electrode.
Figure 1B:
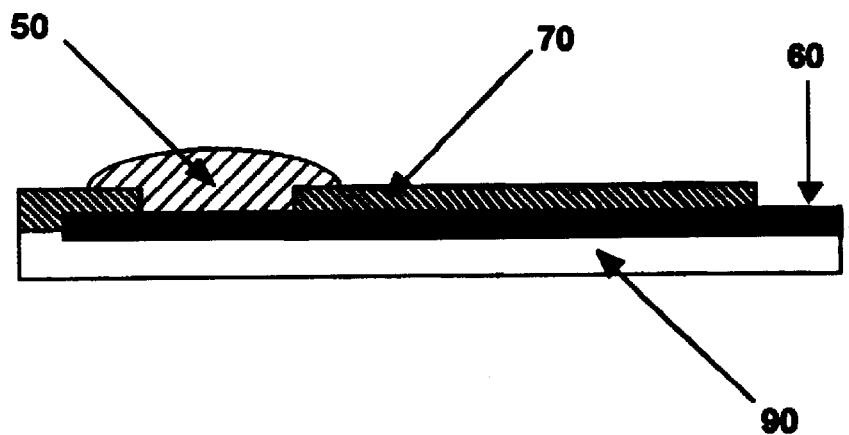
FIG. 1b depicts a schematic view of a solid-state ion-selective membrane electrode.

10: electrobody
20: fixing body
30: inner reference electrode (Ag/AgCl)
40: inner reference solution
50: carbonate ion-selective membrane
60: copper wire
70: insulation film
80: Ag stick
90: aluminum plate
100: enzyme layer
110: gas permeable membrane
120: outer reference electrode (Ag/AgCl)

DETAILED DESCRIPTION OF THE INVENTION

In order to attain the above objective, the present invention provides novel cholanic acid ring based 4-(trifluoroacetyl)phenyl derivatives of the following formula 1.

FORMULA 1

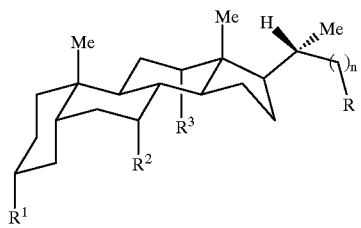

In the foregoing formula 1, n is a value representing the length of alkyl chain and is 0–3; R represents alkyl ($C_1$–$C_{20}$) alkoxy ($C_1$–$C_{20}$) methyl, alkoxy ($C_1$–$C_{20}$) carbonyl, dialkyl ($C_1$–$C_{20}$) amide, dialkly ($C_1$–$C_{20}$) ethylene or diphenylethylene; $R^1$ and $R^3$ represent acetoxy or 4-(trifluoroacetyl) benzoxy; and $R^2$ represents hydrogen, keto, acetoxy or 4-(trifluoroacetyl)benzoxy.

Representative compounds of the present invention are the followings:

1) N,N-dioctyl-3α-acetoxy-7α,12α-bis[4-(trifluoroacetyl)benzoxyl]-5β-cholan-24-amide (compound of example 2);

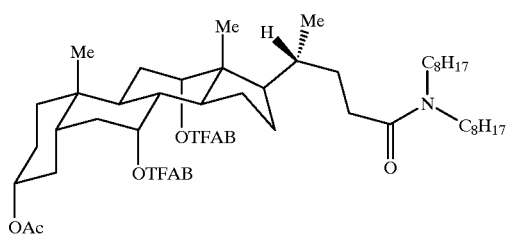

2) N,N-dioctyl-3α, 7α-diacetoxy-12α-[4-(trifluoroacetyl) benzoxyl]-5β-cholan-24-amide (compound of example 3);

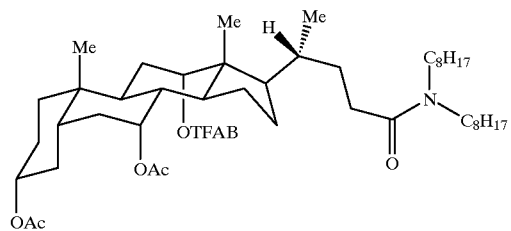

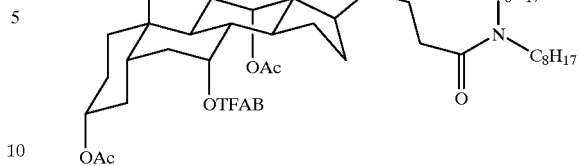

3) N,N-dioctyl-7α-acetoxy-3α, 12α-bis[4-(trifluoroacetyl)benzoxyl]-5β-cholan-24-amide (compound of example 4);

7) N,N-dioctyl-12α-acetoxy-3α, 7α-bis [4-(trifluoroacetyl)benzoxyl]-5β-cholan-24-amide (compound of example 8);

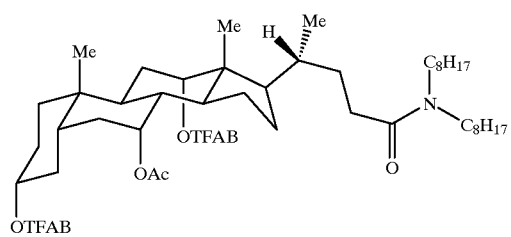

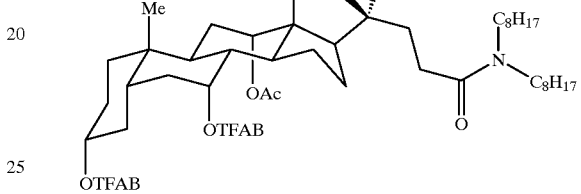

4) N,N-dioctyl-7α, 12α-diacetoxy-3α-[4-(trifluoroacetyl)benzoxyl]-5β-cholan-24-amide (compound of example 5);

8) N,N-dioctyl-3α-acetoxy-12α-[4-(trifluoroacetyl)benzoxyl]-5β-cholan-24-amide (compound of example 9);

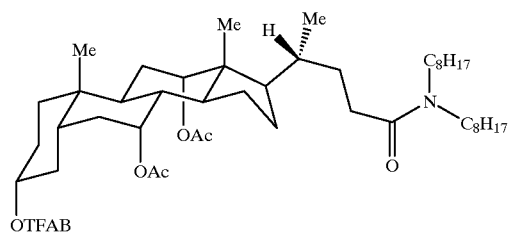

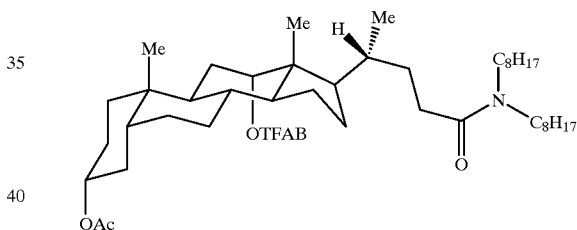

5) N,N-dioctyl-3α, 7α, 12α- tris[4-(trifluoroacetyl)benzoxyl]-5β-cholan-24-amide (compound of example 6);

9) N,N-dioctyl-12α-acetoxy-3α-[4-(trifluoroacetyl)benzoxyl]-5β-cholan-24-amide (compound of example 10);

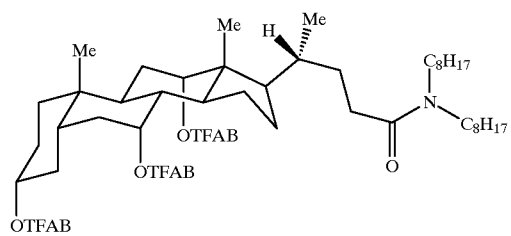

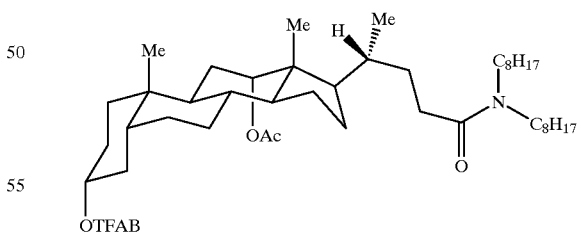

6) N,N-dioctyl-3α, 12α-diacetoxy-7α-[4-(trifluoroacetyl)benzoxyl]-5β-cholan-24-amide (compound of example 7);

10) N,N-dioctyl-3α, 12α-bis[4-(trifluoroacetyl)benzoxyl]-5β-cholan-24-amide (compound of example 11);

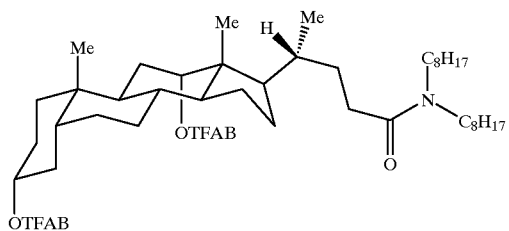

11) N,N-dioctyl-3α, 12α-bis[4-(trifluoroacetyl) benzoxyl]-7- oxo-5β-cholan-24-amide (compound of example 12);

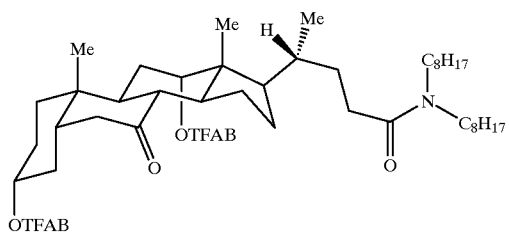

12) 24-(3α, 12α-bis[4-(trifluoroacetyl)benzoxyl]-5β-cholanyl) dodecyl ether (compound of example 13);

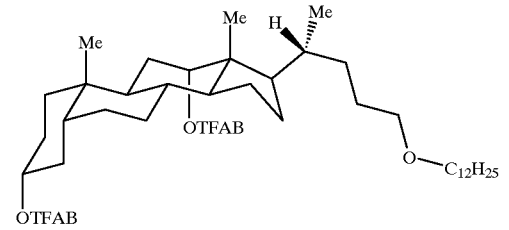

13) 3α, 12α-bis[4-(trifluoroacetyl)benzoxyl]-5β-cholane (compound of example 14);

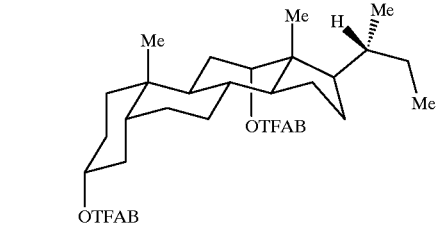

14) 3α, 12α-bis[4-(trifluoroacetyl)benzoxyl]-bisnor-5β-cholanyldimethylethylene (compound of example 15); and

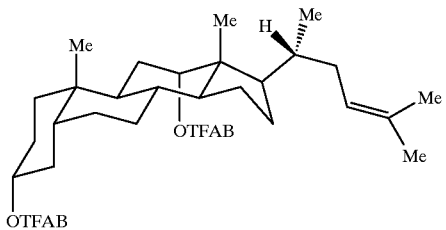

15) 3α, 12α-bis[4-(trifluoroacetyl)benzoxyl]-bisnor-5β-cholanyldiphenylethylene (compound of example 16);

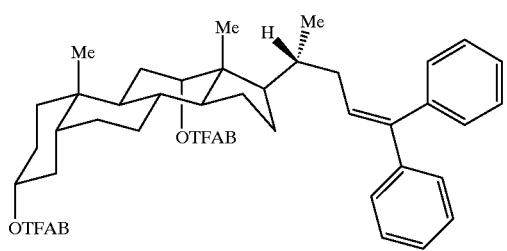

In addition, the present invention provides the preparation method of cholanic acid ring based 4-(trifluoroacetyl)phenyl derivatives of the said formula 1.

The preparation method of cholanic acid ring based 4-(trifluoroacetyl)phenyl derivatives comprises;

1) a step in which the carboxyl group of cholanic acid derivatives is converted to alkyl, alkoxy methyl, alkoxy carbonyl, dialkyl amide, dialkylethylene or .diphenyl-ethylene (step 1);

2) a step in which some of hydroxyl groups of a material prepared in step 1 are selectively acetylated via selective acetylations, selective oxidation-reduction reactions and selective hydrolyses (step 2); and 3) a step in which the material prepared in step 1 or step 2 is reacted with 4-(trifluoroacetyl)benzoyl chloride synthesized by a known method, $CaH_2$ and tetra-n-butylammonium bromide (step 3).

The said preparation method will be described in detail hereinafter.

A step 1 is a protecting step in which the carboxyl group of cholic acid and deoxycholic acid is protected with alkyl, alkoxy methyl, alkoxy carbonyl, dialkyl amide, dialkyleth-ylene or diphenylethylene as described in reaction scheme 1.

REACTION SCHEME 1
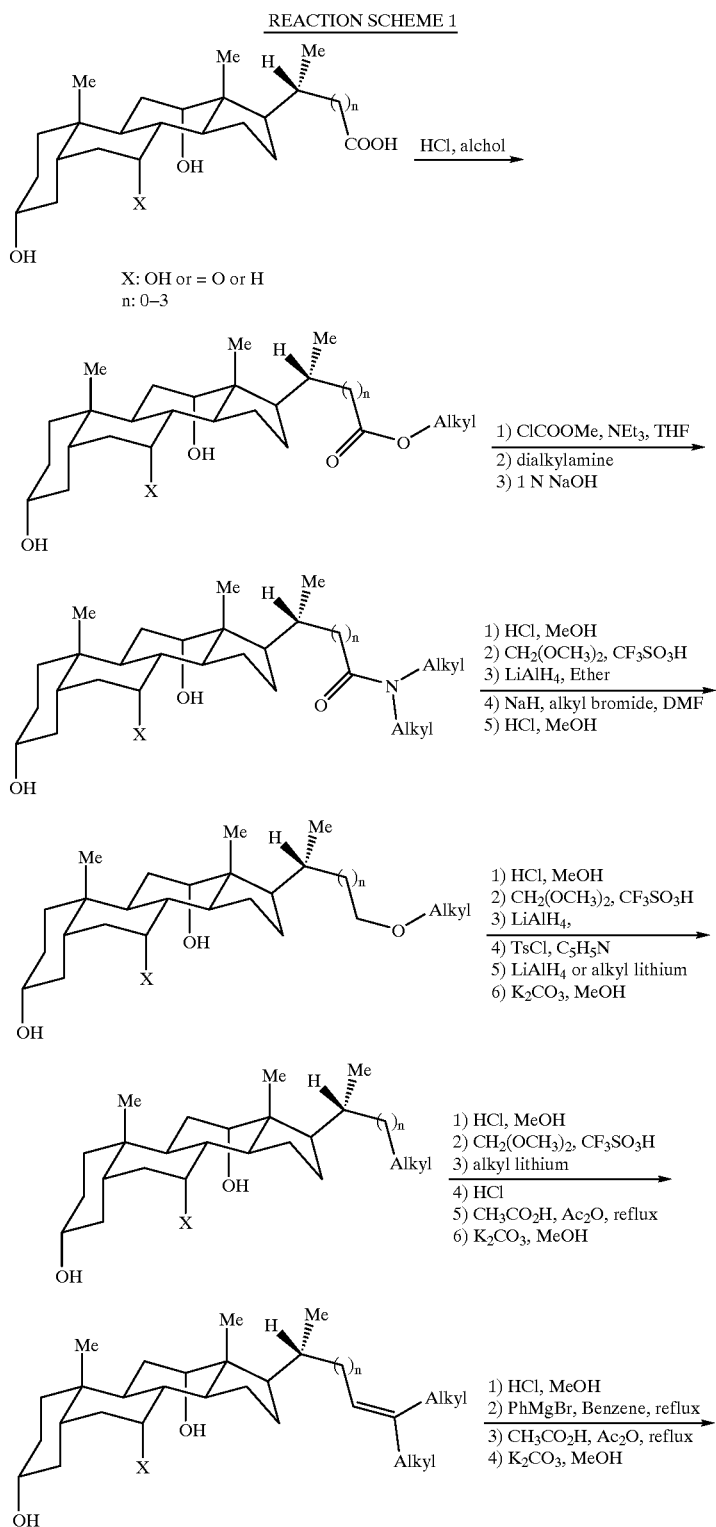

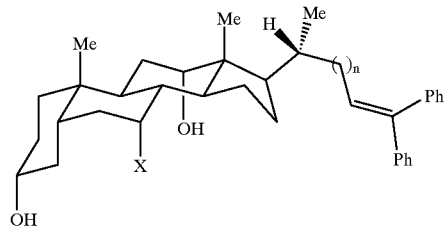

In step 2, it is particularly preferable to protect a hydroxyl group with formyloxy group, before the carboxyl group is activated for the reaction with dialkylamine, when a carboxyl group is a dialkyl amide. The formyloxy groups can be converted to hydroxyl groups after the conversion of carboxyl group. On the other hand, in the case of transforming a carboxyl group to alkyl, alkoxy methyl or dialkylethylene, it is preferable to transform the carboxyl group to methylester, to protect hydroxyl groups with methoxymethyl groups, to transform the ester group to a desired functional group in order.

In step 2, some of the hydroxyl groups of cholanic acid derivatives prepared in step 1 must be selectively acetylated. The first, hydroxyl groups are acetylated by reaction with acetic anhydride ($Ac_2O$) and triethylamine ($NEt_3$) in dichloromethane ($CH_2Cl_2$) solvent as described in reaction scheme 2. In this method, $3\alpha, 7\alpha$, or $12\alpha$-positioned hydroxyl groups can be selectively transformed to acetoxy groups according to the equivalents of acetic anhydride and triethylamine, reaction temperature, and the addition of 4-dimethylaminopyridine. The second, some of acetoxy groups introduced need to be hydrolyzed to hydroxyl group by treatment with $K_2CO_3$ in methanol in order to obtain materials acetylated selectively as described in reaction scheme 3. The third, a $7\alpha$-positioned hydroxyl group is selectively oxidized to keto group and it is reduced to hydroxyl group with the original stereochemistry as described in reaction scheme 4. Acetyl group(s) can be introduced into some of hydroxyl groups of cholanic acid derivatives by the said 3 methods.

REACTION SCHEME 2

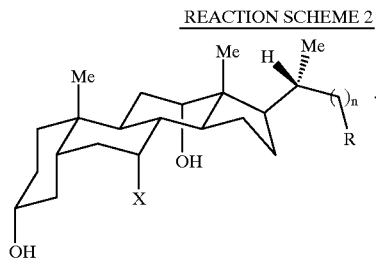

X: OH or = O or H
$R_2$: OAc or = O or H
n: 0–3

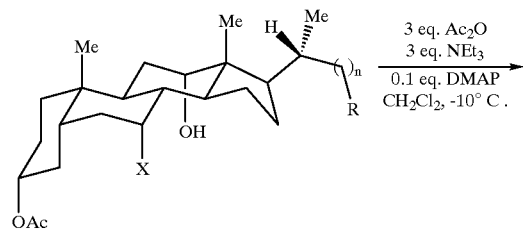

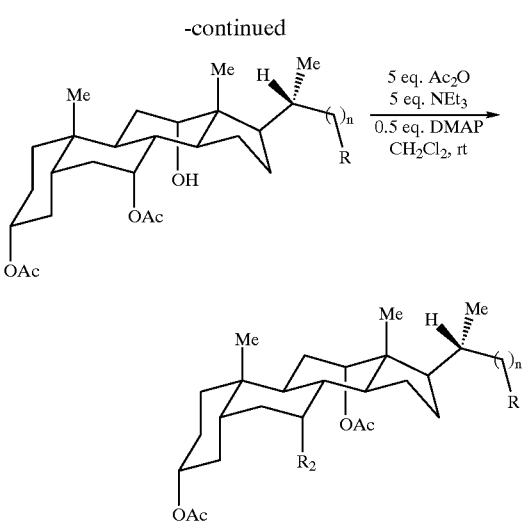

REACTION SCHEME 3

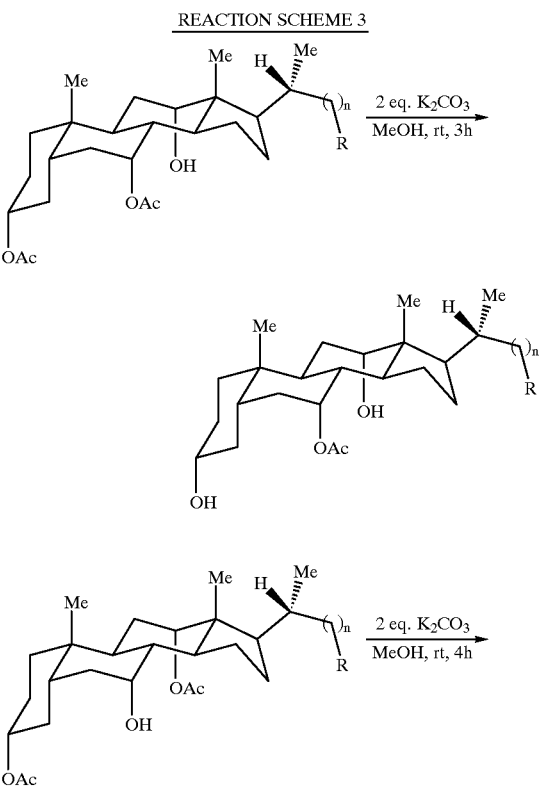

-continued

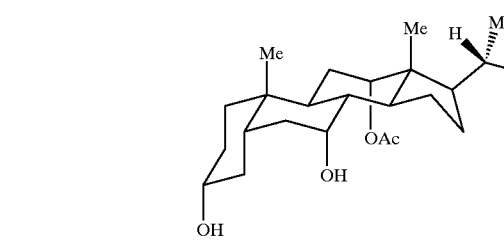

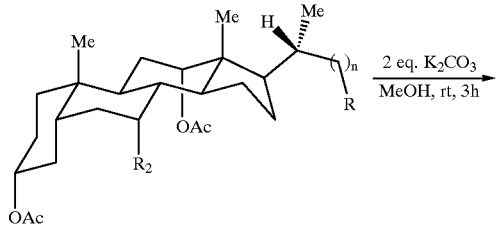

$R_2$: OAc or = O or H
n: 0–3

REACTION SCHEME 4

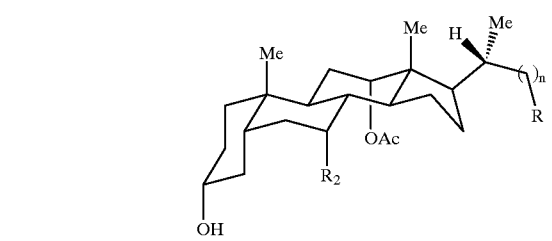

n: 0–3

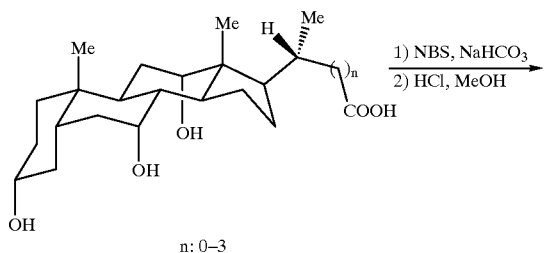

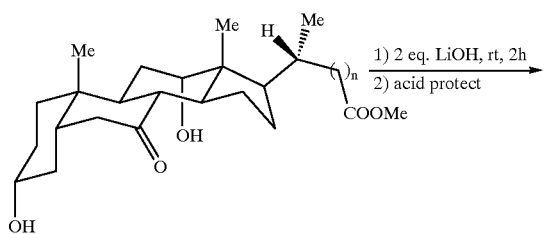

-continued

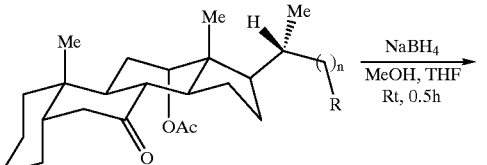

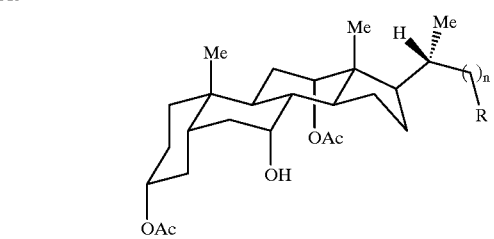

In step 3, a cholanic acid derivative prepared in step 2 is stirred and refluxed with 4-(trifluoroacetyl)benzoyl chloride (TFAB-Cl), CaH$_2$, and tetra-n-butylammonium bromide (n-Bu$_4$NBr) in toluene as described in reaction scheme 5, to obtain cholanic acid ring based 4-(trifluoroacetyl)phenyl derivatives of the present invention. In this step, the desired compound can be prepared by controlling the equivalents of 4-(trifluoroacetyl)benzoyl chloride and CaH$_2$. 4-(trifluoroacetyl)benzoyl chloride was synthesized according to the reported method (*Anal. Chim. Acta*, 1990, 233, 41) with a slight modification as described in reaction scheme 6.

REACTION SCHEME 5

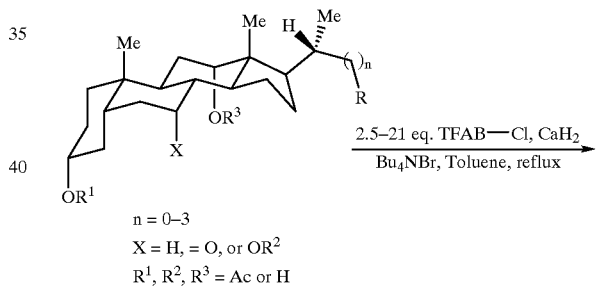

n = 0–3
X = H, = O, or OR$^2$
R$^1$, R$^2$, R$^3$ = Ac or H

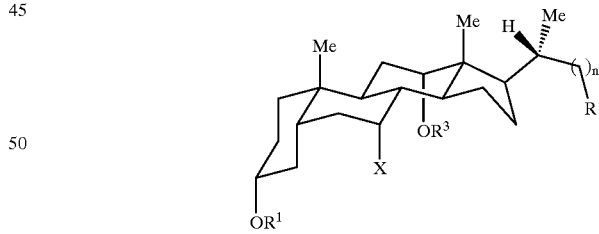

n = 0–3
X = H, = O, or OR$^2$
R$^1$, R$^2$, R$^3$ = Ac or TFAB

TFAB =

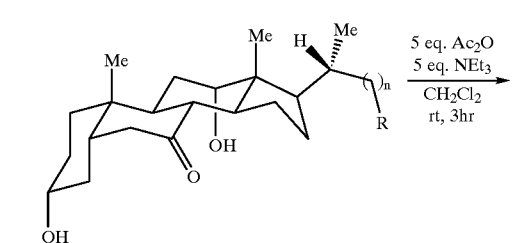

REACTION SCHEME 6

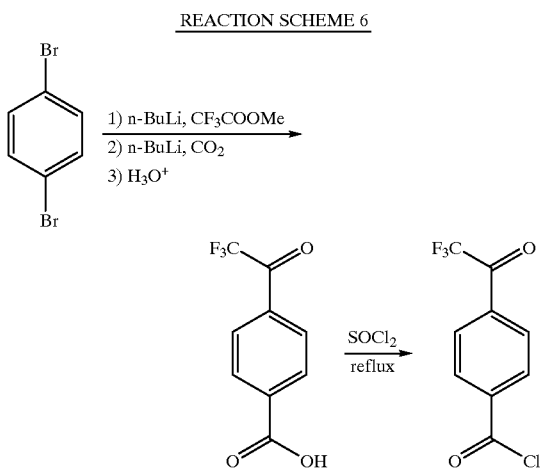

In addition, the present invention provides the use of the said compounds of formula 1 as host-guest materials. That is, the present invention provides the compositions containing the said compounds of formula 1 for host materials.

In the host-guest chemistry, a host material acts as a carrier and a receptor of guest materials and can be used as following uses. For example, it can be used as an ionophore to quantify a specific ion in ion-selective electrodes, optical sensors and gas sensors, and as ion-selective membranes acting as signal transducers in biosensors. And it can be used as a stationary phase separating ions or neutral organic materials in ch-romatographies, as a material for separating, obtaining, concentrating and removing various anions via ionic bonding in photostimulated ion-binding resins and ion exchange resins, as a phase transferring agent in organic reactions, and as a stabilizer of organic polymers such as plastic, wax and rubber.

Therefore the compounds of the present invention can be used as the said host materials.

In addition, the present invention provides, as the one example of the said uses, the compositions for the host materials used in ion sensors and biosensors, which are characterized by containing a cholanic acid ring based 4-(trifluoroacetyl)phenyl derivatives of formula 1, a polymer as a matrix and a non-volatile solvent as a plasticizer.

Besides of the use in the said ion sensor and biosensor, the said composition for a host material can be used in various sensors for detecting carbonate ion and derivatives thereof in the analysis of environmental or biological sample.

When the said composition for a host material is used in a biosensor, the urea enzyme layer can be introduced onto the ion-selective membrane electrode of the biosensor.

In the said composition for a host material, all the compound of formula I can be used as an ionophore.

In the said composition for a host material, a polymer such as poly(vinylchloride) (hereinafter, referred to as "PVC"), polyurethan, silicone rubber, cellulose acetate or cellulose triacetate can be used as a matrix.

In the said composition for a host material, a compound selected from the group comprising ether compounds such as bis(2-ethylhexyl)adipate (hereinafter, referred to as "DOA"), bis(2-ethylhexyl)sebacate (hereinafter, referred to as "DOS"), bis(2-ethylhexyl)phthalate (hereinafter, referred to as "DOP"), bis (1-butylphenyl)adipate (hereinafter, referred to as "BBPA") and 2-nitrophenyl octyl ether (hereinafter, referred to as "NPOE") can be used as a plasticizer.

In the said composition for a host material, a lipophilic additive can be further added, and a quarternary ammonium salt such as tridodecylmethylammonium chloride (hereinafter, referred to as "TDMA-Cl") can be used as a lipophilic additive.

The compound of formula 1 of the present invention has particularly excellent selectivity for carbonate ion, so it can substitute TFADB, an tonophore for carbonate ion, which has been used in an ion-selective membrane electrode, one of ion sensors.

The mechanism of interaction between a carbonate ion and TFAP derivatives was suggested by Meyerhoff et al. According to this mechanism, TFAP derivatives are bound to carbonate ion to form 2:1 complex by the mechanism shown below. The binding affinity is determined by the binding force between an electophilic neutral carrier and a nucleophilic carbonate ion, affected by an inducing effect or a resonance effect controlled by substituent of para position, and it has a great effect on the selectivity for a carbonate ion.

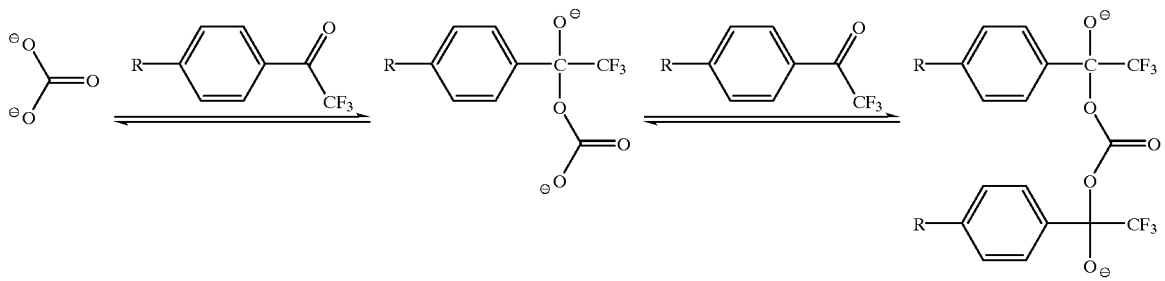

Therefore, in the present invention structurally fixed cholanic acids with TFAP groups substituted at $3\alpha$, $7\alpha$ and $12\alpha$-position of which number and position are varied were synthesized, based on the response mechanism of a carbonate icn-selective material with TFAP groups. And then it was examined whether the said synthesized compounds with two or more TFAP groups can respond to a carbonate ion and change the selectivity against lipophilic anions, especially salicylate ion. These properties were compared with those of already known TFADB, according to the number and the position of substituents. As a result, by using the composition comprising the material into which is introduced by TFAP groups, the interference of lipophilic anions, which has been indicated as a serious problem, has been greatly decreased in detecting carbonate ions of biological sample.

A biosensor was designed in order to measure biological materials such as various enzymes, microorganisms, antibodies, antigens and tissues of animals and plants, and it can be widely applied to medical diagnosis, food engineering, and measurement and observation of environmental polluting materials as well as biological science.

For example, a urea sensor, one of biosensors, is used to determine the concentration of urea in the body which is a barometer for the abnormality of a liver and a kidney because the concentration of urea in the body is determined by the amount generated by a liver and the amount excreted from a kidney. The principle of a urea sensor is for urease adsorbed onto a electrode surface to react with urea in the urine to generate carbonate dons by the reaction mechanism as shown below and for carbonate ion-selective membrane of signal transducer to respond to the carbonate ions generated in the above step.

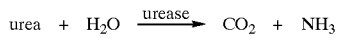

TFAP derivative of the present invention can be substituted for TFADB, a carbonate ion-selective material acting as signal transducer in a biosensor, like as the said carbonate ion-selective material of an ion-selective membrane, one of ion sensors.

As above, L-glutamic acid and glutamate decarboxylase or tyrosine and tyrosine decarboxylase are used as a substrate and an enzyme of a biosensor which can use a carbonate ion-selective membrane as signal transducer, and the reaction mechanism is as followings.

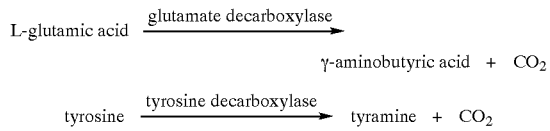

A $CO_2$ gas sensor of the present invention among gas sensors is used Lo measure the concentration of $CO_2$ in the body. A small amount of $CO_2$ is dissolved in blood as a final product of the metabolic pathway. The concentration of $CO_2$ in the body is closely related to the balance between acid and base and the pH of blood, and is an important standard to determine the gas exchange function of a lung and the abnormality of metabolism, and the abnormal concentration of $CO_2$ causes various diseases. Therefore measuring concentration of $CO_2$ is a general test for patient with lung trouble and a standard test for determining the balance of electrolytes.

Figure 8A:
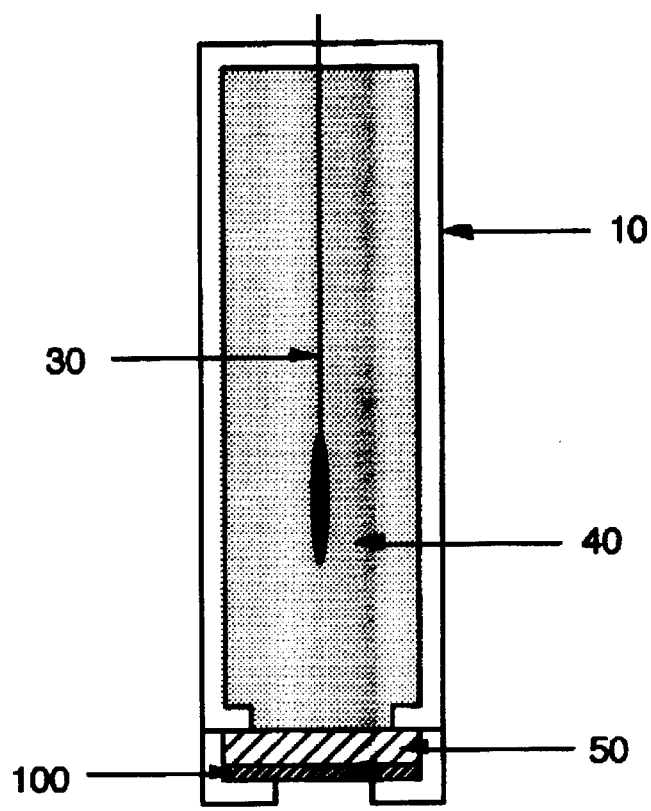
FIG. 8a depicts a schematic view of a conventional urea sensor using, as signal transducer, a carbonate ion-selective membrane electrode prepared with TFAP derivative as an ionophore, to which an enzyme layer is introduced.

FIG. 8 shows the structure of a Severinghause-type $CO_2$ gas sensor. $CO_2$ of sample permeates across a gas permeable membrane and enter the high pH recipient solution. The entered $CO_2$ then reacts with $H_2O$ of the recipient solution to generate a carbonate ion and a proton. The carbonate ion-selective membrane electrode responds to the carbonate ion generated by the said process and quantifies the amount of $CO_2$ of sample indirectly. The $CO_2$ gas sensor which uses, as signal transducer, the carbonate ion-selective membrane prepared with the composition for a host material of the present invention, has excellent response to carbonate ions (See FIG. 9).

The novel cholanic acid ring based 4-(trifluoroacetyl) phenyl derivatives of the present invention may be used as a host material in the host-guest chemistry by including a suitable matrix, plasticizer or lipophilic additive. The compounds of the present invention show the excellent selectivity for carbonate ion particularly. The ion-selective membranes containing these compounds have the more improved response slope than that prepared with the already known TFADB, which was formed on the surface of the carbonate ion-selective electrode prepared with the composition membrane of the present invention, and decreases the interference of lipophilic anions, especially salicylate ion. Therefore the ion-selective membrane of the present invention may be used as an ionic binding material for carbonate ion and derivatives thereof in analysis of carbonate ions in a biological or an environmental sample. In addition, the compounds of the present invention may be applied to ion sensors, optical sensors, gas sensors, biosensors, chromatographies, photostimulated ion-binding resins, ion exchange resins and organic reactions.

Practical and presently preferred embodiments of the present invention are illustrative as shown in the following examples.

However, it will be appreciated that those skilled in the art, on consideration of this disclosure, may make modification and improvements within the spirit and scope of the present invention.

EXAMPLES

Example 1

Preparation of 4-(trifluoroacetyl)benzoyl chloride (Step 1) Preparation of 4-(trifluoroacetyl)benzoic acid A solution of 10.00 g (42.4 mmol) of 1,4-dibromobenzene in 160 mL of ether-THF (1:1) mixture was stirred at −78° C. when 18.90 mL (42.4 mmol) of 2.24 M butyithium in hexane was added dropwise over a period of 35 min. After the solution was stirred for 30 min, 4.26 mL (42.4 mmol) of methyl trifluoroacetate was added for 20 min at the same temperature. The solution was stirred for 20 min more and 18.90 mL (42.4 mmol) of 2.24 M butyllithium in hexane was added for 35 min. After 25 min stirring, $CO_2$ gas was added for 1 h and then the cold bath was removed. The slurry was stirred for 30 min, 200 mL of 1 M HCl was added, and the two layers were separated. The aqueous fraction was extracted 3 times with 100 mL, of diethyl ether. The combined organic fractions were dried over anhydrous $MgSO_4$ and concentrated. The residue was triturated in 100 mL of hexane for 1 h at 0° C. The solid was filtered and washed with 200 mL of hexane. The combined filtrate and washing were concentrated and the residue was triturated with 70 mL of hexane again to obtain additional product. Collected solid products were combined and dried in vacuum to obtain 7.80 g (84%) of the crude desired compound as a yellowish white solid. The crude product was used without further purification for the preparation of the corresponding acid chloride at the following step. The following $^1$H NMR spectrum data was obtained from the sample obtained from the hydrolysis of 4-(trifluoroacetyl)benzoyl chloride, which is described below.

$C_9H_5F_3O_5$; TLC (ethyl acetate:n-hexane=1:1) $R_f$, 0.15; mp 176–178° C.; $^1$H NMR (300 MHz, DMSO-$d_6$/CDCl$_3$) δ 13.20 (br, 1H), 7.99–7.71 (m, 4H); IR (KBr) $v_{max}$ 3600–2500(br), 1711, 1600 cm$^{-1}$.

(Step 2) Preparation of 4-trifluoroacetylbenzoyl chloride

A mixture of 7.80 g (35.8 mmol) of the product of step 1 in 13 mL of SOCl$_2$ was refluxed for 3 h. After excess SOC$_2$ was removed under reduced pressure, the residue was purified by Kugelrohr distillation at 70° C. (0.3 mmHg) to obtain 6.60 g (78%) of the desired compound. The purity of this compound was confirmed by the IR spectrum of this compound and the $^1$H NMR spectrum of the sample of step 1 which was obtained by hydrolysis of this compound.

IR (neat) $v_{max}$ 3112, 3059, 1789, 1736, 1572, 1499, 1420, 1335, 1190, 1150, 953, 894, 749 cm$^{-1}$.

Example 2

Preparation of N,N-dioctyl-3α-acetoxy-7α, 12α-bis [4-(triflucoroacetyl)benzoxy]-5β-cholan-24-amide (Step 1) Preparation of 3α,7α,12α-triformyloxy-5β-cholic acid A mixture of 2.05 g (5 mmol) of cholic acid and 2 drops of 70% $HClO_4$ in 8 mL of 98% formic acid was stirred at 40–45° C. for 1.5 h. After the mixture was allowed to cool to 35° C., $Ac_2O$ was added slowly to let the temperature of the solution maintained between 40–45° C. until a large quantity of bubbles appeared. After the solution was poured into 80 mL of water, the precipitate was filtered, washed with water, and dried to give 2.46 g (100%) of the desired compound as white powder.

$C_{27}H_{40}O_8$; TLC (acetoorne:n-hexarie=1:1) $R_f$, 0.55; mp 206–208° C.; $^1H$ NMR (300 MHz, $CDCl_3$) δ 12.0 (br m, 1H), 8.15 (s, 1H), 8.09 (s, 1H), 8.01 (s, 1H), 5.25 (s, 1H, 12-CH), 5.06 (s, 1H, 7-CH), 4.70 (br, 1H, 3-CH), 2.41–0.75 (m, 33H).

(Step 2) Preparation of N,N-dioctyl-3α,7α,12α-triformyl oxy-5β-cholan-24-amide

A solution of 2.46 g (5 mmol) of the product of step 1 and 0.770 mL (5.5 mmol) of triethylamine ($NEt_3$) in 45 mL of $CH_2Cl_2$ was stirred at 0° C. as 0.428 mL (5.5 mmol) of methyl chloroformate was added dropwise. The solution was stirred for 2 h at 0° C. and 1.81 mL (6 mmol) of N,N-dioctylamine was added dropwise. After 2 h, the solution was diluted with 100 mL of $CH_2Cl_2$, washed with 100 mL of water, dried over anhydrous $MgSO_4$, and concentrated. The residue was purified by silica gel column chromatography (ethyl acetate:n-hexane=3:17) to give 2.7 g (75%) of the desired compound as a waxy solid.

$C_{43}H_{73}NO_7$; TLC (ethyl acetate:n-hexane=3:7) $R_f$, 0.42; $^1H$ NMR (300 MHz, $CDCl_3$) δ 8.16–8.02 (s, 3H), 5.28 (s, 1H, 12-CH), 5.06 (s, 1H, 7-CH), 4.85 (br m, 1H, 3-CH), 3.4–3.18 (m, 4H), 2.39–0.68 (m, 63H); IR (film) $v_{max}$ 2940, 2861, 2736, 1729, 1637, 1473, 1314, 1190, 762 $cm^{-1}$.

(Step 3) Preparation of N,N-dioctyl-3α,7α,12α-trihydroxy-5β-cholan-24-amide

To a solution of 850 mg (1.19 mmol) of the product of step 2 in 17 mL of THF was added 15 mL of 3% $K_2CO_3$ in 80% aq. MeOH and the mixture was stirred at 60° C. for 72 h. After the solution was concentrated to a small volume, the residual solution was diluted with 100 mL of $CH_2Cl_2$, washed with 40 mL of saturated $NH_4Cl$ and 100 mL of water, dried over anhydrous $MgSO_4$, and concentrated. The mixture was purified by silica gel column chromatography (ethyl acetate:n-hexane=13:7) to give 570 mg (76%) of the desired compound as a waxy solid.

$C_{40}H_{73}NO_4$; TLC (ethyl acetate) $R_f$ 0.25; $^1H$ NMR (300 MHz, $CDCl_3$) δ 3.99 (s, 1H, 12-CH), 3.84 (s, 1H, 7-CH), 3.43 (br m, 1H, 3-CH), 3.37–3.20 (m, 4H), 2.24–0.67 (m, 63H); IR ($CHCl_3$) $v_{max}$ 3408 (br), 2943, 2864, 1625, 1474, 1383 $cm^{-1}$.

(Step 4) Preparation of N,N-dioctyl-3α-acetoxy-7α,12α-dihydroxy-5β-cholan-24-amide A solution of 580 mg (0.92 meol) of the product of step 3, 0.385 mL (2.76 mmol) of $NEt_3$, and 0.260 mL (2.76 mmol) of $Ac_2O$ in 3 mL of $CH_2Cl_2$ was stirred at rt for 65 h. The solution was concentrated and the residue was dissolved in 30 mL of ether. The solution was washed with 30 mL of 1 M HCl, dried over anhydrous $MgSO_4$ and concentrated. The residue was purified by silica gel column chromatography (ethyl acetate:n-hexane=1:3) to give 350 mg (56%) of the desired compound as a waxy solid.

$C_{42}H_{75}NO_5$; TLC (ethyl acetate:n-hexane=1:2) $R_f$, 0.31; $^1H$ NMR (300 MHz, $CDCl_3$) δ 4.10 (s, 1H, 12-CH), 4.06 (br m, 1H, 3-CH), 3.99 (s, 1H, 7-CH), 3.24–3.19 (m, 4H), 2.03 (s, 3H), 2.21–0.69 (m, 63H); IR ($CHCl_3$) $v_{max}$ 3426 (br), 2949, 2846, 1734, 1631, 1474, 1371, 1257 $cm^{-1}$.

(Step 5) Preparation of N,N-dioctyl-3α-acetoxy-7α,12β-bis [(4-trifluoroacetyl)benzoxy)]-5β-cholan-24-amide A mixture of 520 mg (0.78 mmol) of the product of step 4, 344 mg (7.80 mmol) of CaH, and 66 mg (0.20 mmol) of tetra-n-butylammonium bromide ($Bu_4NBr$) in 7 mL of toluene was stirred at rt as 2.58 g (10.9 mmol) of 4-trifluoroacetylbenzoyl chloride was added. The mixture was refluxed for 24 h, allowed to cool to rt, and filtered through celite. The celite was washed with 100 mL, of ethyl acetate and the combined filtrate and washing were concentrated. To the residue were added 0.2 mL of water, 40 g of silica gel and 70 mL of toluene and the mixture was stirred at rt for 2 h. The silica gel was filtered and washed with 150 mL of ethyl acetate. The combined filtrate and washing were concentrated and the residue was dissolved in 70 mL of ether, washed twice with 70 mL of the saturated $NaHCO_3$, dried over anhydrous $MgSO_4$, and concentrated. The residue was purified by silica gel column chromatography (ethyl acetate:n-hexane=1:4) to give 480 mg (57%) of the desired compound as a waxy solid.

$C_{60}H_{81}F_6NO_9$; TLC (ethyl acetate:n-hexane=1:1) $R_f$ 0.47; $^1H$ NMR (300 MHz, $CDCl_3$) δ 8.26–8.10 (m, 8H), 5.48 (s, 1H, 12-CH), 5.32 (s, 1H, 7-CH), 4.51 (br m, 1H, 3-CH), 3.27–3.06 (m, 4H), 2.18 (s, 3H), 2.37–0.81 (m, 63H); $^{13}C$ NMR (75 MHz, $CDCl_3$) δ 12.12, 13.95, 17.67, 21.04, 21.31, 22.34, 22.49, 22.90, 25.43, 26.54, 26.68, 26.85, 27.03, 27.55, 28.89, 29.02, 29.10, 29.23, 29.59, 29.85, 31.12, 31.29, 31.58, 31.65, 31.81, 34.33, 34.43, 34.74, 34.93, 38.10, 40.41, 43.64, 45.44, 45.83, 47.85, 48.19, 72.54, 73.44, 77.00, 116.22 (q, J=291 Hz), 129.75, 129.81, 130.00, 133.00, 133.10, 136.21, 163.63, 163.95, 170.24, 172.60, 179.58 (q, J=35 Hz); $^{19}F$ NMR (282 MHz, $CDCl_3$) δ 120.08, 120.10; IR (film) $v_{max}$ 2934, 2861, 1729, 1618, 1473, 1374, 1282, 1190, 1065, 736 $cm^{-1}$; LRFABMS (NBA) m/z 1074.58 (M+H), 1092.59 (M+$H_2O$+H), 1110.57 (M2$H_2O$+H) 1227.62 (M+NBA+H), 1245.7 (M+NBA+$H_2O$+H); HRFABMS (NBA) Calcd for $C_{60}H_{82}F_6NO_9$ (M+H); 1074.5894 Found; 1074.5870.

Example 3

Preparation of N,N-dioctyl-3α,7α-diacetoxy-12α-[(4-trifluoroacetyl)benzoxyl]-5α-cholan-24-amide (Step 1) Preparation of N,N-dioctyl-3α,7α-diacetoxy-12α-hydroxy-5β-cholan-24-amide A solution of 1.58 g (2.50 mmol) of the product of step 3 of example 2, 1.01 mL (7.50 mmol) of $NEt_3$, 15 mg (0.25 mmol) of 4-dimethylaminopyridine (DMAP) in 10 mL of $CH_2Cl_2$ was stirred and allowed to cool to –78° C. as 0.710 mL (7.50 mmol) of $Ac_2O$ was added. The reaction mixture was stirred for 1 h and left at –10° C. for 20 h. After the solution was concentrated, the mixture was dissolved in 50 mL of ether, washed with 50 mL of 1 M HCl, dried over anhydrous $MgSO_4$, and concentrated. The residue was purified by silica gel column chromatography (ethyl acetate:n-hexane=1:4) to give 1.10 g (62%) of the desired compound as a waxy solid.

$C_{44}H_{77}NO_6$; TLC (ethyl acetate:n-hexane=1:1) $R_f$ 0.46; $^1H$ NMR (300 MHz, $CDCl_3$) δ 4.87 (s, 1H, 7-CH), 4.56 (br m, 1H, 3-CH), 3.99 (s, 1H, 12-CH), 3.19–3.17 (m, 4H), 2.04 (s, 3H), 2.00 (s, 3H), 2.20–0.56 (m, 63H); IR ($CHCl_3$) $v_{max}$ 3689, 2929, 1739, 1634, 1482, 1389, 1250 $cm^{-1}$.

(Step 2) Preparation of N,N-dioctyl-3α,7α-diacetoxy-12α-[(4-trifluoroacetyl)benzoxy]-5β-cholan-24-amide A mixture of 240 mg (0.34 mmol) of the product of step 1, 78 mg (1.70 mmol) of $CaH_2$ and 22 mg (0.07 mmol) of Bu$_4$NBr in 3 mL of toluene was stirred at rt as 279 mg (1.19 mmol) of 4-trifluoroacetylbenzoyl chloride was added. The mixture was refluxed for 24 h, allowed to cool to rt, and filtered through celite. The celite was washed with 80 mL of ethyl acetate and the combined filtrate and washing were concentrated. The residue was dissolved in 70 mL of ether, washed twice with 70 mL of the saturated NaHCO$_3$, dried over anhydrous MgSO$_4$ and concentrated. The residue was purified by silica gel column chromatography (ethyl acetate:n-hexane=1:3) to give 280 mg (91%) of the desired compound as a waxy solid.

C$_{53}$H$_{80}$ F$_3$NO$_8$; TLC (ethyl acetate:n-hexane=1:1) R$_f$, 0.50; $^1$H NMR (300 MHz, CDCl3) δ 8.24–8.19 (m, 4H), 5.41 (s, 1H, 12-CH), 4.98 (s, 1H, 7-CH), 4.52 (br m, 1H, 3-CH), 3.27–3.11 (m, 4H), 2.12 (s, 3H), 1.92 (s, 3H), 2.08–0.61 (m, 63H); $^{13}$C NMR (75 MHz, CDCl$_3$) δ 12.21, 13.99, 17.71, 21.23, 21.49, 22.41, 22.52, 22.55, 22.87, 25.53, 26.67, 26.79, 26.95, 27.24, 27.69, 28.83, 29.02, 29.08, 29.16, 29.18, 29.30, 29.60, 30.03, 31.16, 31.26, 31.64, 31.71, 34.31, 34.55, 34.64, 34.94, 37.78, 40.75, 43.59, 45.45, 45.82, 47.86, 48.28, 70.72, 73.74, 77.23, 116.37 (q, J=291 Hz), 129.92, 130.13, 132.99, 136.58, 164.28, 170.03, 170.39, 172.50, 179.99 (q, J=36 Hz); $^{19}$F NMR (282 MHz, CDCl$_3$) δ 120.32; IR (film) ν$_{max}$ 2940, 2861, 1723, 1624, 1473, 1387, 1282, 1183, 1071, 1025, 769 cm$^{-1}$; LRFABMS (NBA) m/z 916.49 (M+H), 934.50 (M+H$_2$O+H), 1069.50 (M+NBA+H); HRFABMS (NBA) Calcd for C$_{53}$H$_{81}$F$_3$NO$_8$ (M+H); 916.5914 Found; 916.5922; HRFABMS (NBA) Calcd for C$_{53}$H$_{83}$F$_3$NO$_9$ (M+H$_2$O+H); 934.6019 Found; 934.6047.

Example 4

Preparation of N,N-dioctyl-7α-acetoxy-3α, 12α-bis[(4-trifluoroacetyl)benzoxy]-5β-cholan-24-amide (Step 1) Preparation of N,N-dioctyl-7α-acetoxy-3α, 12α-dihydroxy-5 β-cholan-24-amide A solution of 136 mg (0.19 mmol) of the product of step 1 of example 3 and 52 mg (0.38 mmol) of K$_2$CO$_3$ in 2 mL of MeOH was stirred at rt for 6 h and 1.3 mL of acetic acid was added to the solution. After 30 min stirring, the solution was concentrated and the residue was dissolved in 30 mL of ether. The solution was washed with 30 mL of brine and 50 mL of water, dried over anhydrous MgSO$_4$, and concentrated. The residue was purified by silica gel column chromatography (ethyl acetate:n-hexane=2:1) to give 110 mg (86%) of the desired compound as a waxy solid.

C$_{42}$H$_{75}$NO$_5$; TLC (100 % ethyl acetate) R$_f$, 0.48; $^1$H NMR (300 MHz, CDCl$_3$) δ 4.89 (s, 1H, 7-CH), 4.01 (s, 1H, 12-CH), 3.48 (br m, 1H, 3-CH), 3.37–3.15 (m, 4H), 2.06 (s, 3H), 2.25–0.65 (m, 63H); IR (CHCl$_3$) ν$_{max}$ 3439 (br),2947, 2856, 1733, 1628, 1488, 1390, 1256 cm$^{-1}$.

(Step 2) Preparation of N,N-dioctyl-7α-acetoxy-3α, 12α-bis[(4-(trifluoroacetyl)benzoxy]-5β-cholan-24-amide A mixture of 323 mg (0.48 mmol) of the product of step 1, 212 mg (4.80 mmol) of CaH$_2$ and 40 mg (0.12 mmol) of Bu$_4$NBr in 5 mL of toluene was stirred at rt as 1.59 g (6.72 mmol) of 4-trifluoroacetyl)benzoyl chloride was added. The mixture was refluxed for 24 h, allowed to cool to rt, and filtered through celite. The celite was washed with 80 mL of ethyl acetate and the combined filtrate and washing were concentrated. To the residue were added 0.1 mL, of water, 25 g of silica gel, and 50 mL of toluene, and the mixture was stirred for 2 h. The silica gel was filtered and washed with 150 mL of ethyl acetate. The combined filtrate and washing were concentrated and the residue was dissolved in 70 mL of ether, washed twice with 70 mL of the saturated NaHCO$_3$, dried over anhydrous MGSO$_4$, and concentrated under reduced pressure. The residue was purified by silica gel column chromatography (ethyl acetate:n-hexane=1:4) to give 195 mg (38%) of the desired compound as a waxy solid.

C$_{60}$H$_{81}$F$_6$NO$_9$; TLC (ethyl acetate:n-hexane=1:1) R$_f$, 0.44; $^1$H NMR (300 MHz, CDCl$_3$) δ 8.21–8.08 (m, 4H), 8.03–7.91 (m, 4H), 5.20 (s, 1H, 12-CH), 4.93 (s, 1H, 7-CH), 4.72 (br m, 1H, 3-CH), 3.23–3.02 (m, 4H), 2.05 (s, 3H), 2.26–0.64 (m, 63H); $^{13}$C NMR (75 MHz, CDCl$_3$) δ 12.21, 13.99, 17.73, 21.46, 22.38, 22.55, 22.62, 22.89, 25.53, 26.67, 26.79, 26.95, 27.24, 27.67, 28.85, 29.01, 29.10, 29.18, 29.30, 29.62, 30.06, 31.15, 31.26, 31.66, 31.72, 31.86, 34.33, 34.53, 34.61, 34.98, 37.81, 40.78, 43.57, 45.43, 45.88, 47.91, 48.26, 70.76, 75.44, 77.18, 116.32 (q, J=291 Hz), 129.68, 129.89, 130.04, 132.78, 133.01, 136.33, 136.63, 164.18, 164.37, 169.89, 172.61, 179.87 (q, J=36 Hz), 179.91 (q, J=35 Hz); $^{19}$F NMR (282 MHz, CDCl$_3$) δ 120.14, 120.21; IR (film) ν$_{max}$ 2934, 2855, 1729, 1624, 1466, 1387, 1289, 1190, 1124, 1071, 1025, 946, 736 cm$^{-1}$; LRFABMS (NBA) m/z 1074.50 (M+H), 1092.54 (M+H$_2$O+H), 1110.52 (M+2H$_2$O+H), 1227.5 (M+NBA+H), 1245.5 (M+NBA+H$_2$O+H); HRFABMS (NBA) Calcd for C$_{60}$H$_{82}$F$_6$NO$_9$ (M+H); 1074.5894 Found; 1074.5907.

Example 5

Preparation of N,N-dioctyl-7α,12α-diacetoxy-3α-[(4-trifluoroacetyl)benzoxy]-5β-cholan-24-amide (Step 1) Preparation of N,N-dioctyl-7α,12α-diacetoxy-3α-hydroxy-5β-cholan-24-amide A solution of 632 mg (1.00 mmol) of the product of step 3 of example 2, 0.697 mL (5.00 mmol) of NEt$_3$, 61 mg (0.50 mmol) of DMAP, and 0.472 mL (5.00 mmol) of Ac$_2$O in 3 mL of CH$_2$Cl$_2$ was stirred at rt for 20 h, and volatile materials were removed under reduced pressure. The residue was dissolved in 30 mL of ether, washed twice with 30 mL of 1 M HCl, dried over anhydrous MgSO$_4$, and concentrated to obtain crude N,N-dioctyl-3α,7α,12α-triacetoxy-5β-cholan-24-amide.

The solution of the crude triacetate and 276 mg (2.00 mmol) of K$_2$CO$_3$ in 5 mL of MeOH was stirred at rt for 3 h and 3.0 mL (50.5 mmol) of acetic acid was added to the solution. The solution was stirred for 30 min and concentrated. The residue was dissolved in 40 mL of ether, washed with 40 mL of brine and 40 mL of water, dried over anhydrous MgSO$_4$, and concentrated. The residue was purified by silica gel column chromatography (ethyl acetate:n-hexane=1:1) to give 490 mg (69%) of the desired compound as a waxy solid.

C$_{44}$H$_{77}$NO$_6$; TLC (100% ethyl acetate) R$_f$, 0.60; $^1$H NMR (300 MHz, CDCl$_3$) δ 5.07 (s, 1H, 12-CH), 4.87 (s, 1H, 7-CH), 3.56 (br m, 1H, 3-CH), 3.28–3.13 (m, 4H), 2.09 (s, 3H), 2.06 (s, 3H), 2.20–0.54 (m, 63H); IR CHCl$_3$) ν$_{max}$ 3696, 2929, 1733, 1693, 1634, 1482, 1376, 1197 cm$^{-1}$.

(Step 2) Preparation of N,N-dioctyl-7α,12α-diacetoxy-3α-[(4-(trifluoroacetyl)benzoxy]-5β-cholan-24-amide A mixture of 240 mg (0.34 mmol) of the product of step 1, 46 mg (1.00 mmol) of CaH$_2$ and 22 mg (0.07 mmol) of Bu$_4$NBr in 3 mL of toluene was stirred at rt as 199 mg (0.85 mmol) of 4-trifluoroacetylbenzoyl chloride was added. The mixture was refluxed for 1 h, allowed to cool to rt, and filtered through celite. The celite was washed with 80 mL of ethyl acetate and the combined filtrate and washing were concentrated. The residue was dissolved in 70 mL of ether, washed twice with 70 mL of the saturated NaHCO$_3$, dried over anhydrous MgSO$_4$, and concentrated. The residue was purified by silica gel column chromatography (ethyl acetate:n-hexane=1:4) to give 242 mg (78% ) of the desired compound as a waxy solid.

$C_{53}H_{80}F_3NO_8$; TLC (ethyl acetate:n-hexane=1:1) $R_f$, 0.70; $^1$H NMR (300 MHz, CDCl$_3$) δ 8.17–8.15 (m, 4H), 5.12 (s, 1H, 12-CH), 4.93 (s, 1H, 7-CH), 4.85 (br m, 1H, 3-CH), 3.28–3.21 (m, 4H), 2.13 (s, 3H), 2.07 (s, 3H), 2.20–0.75 (m, 63H); $^{13}$C NMR (75 MHz, CDCl$_3$) δ 12.21, 14.06, 17.68, 21.35, 21.58, 22.56, 22.57, 22.59, 22.77, 25.56, 26.86, 26.98, 27.22, 27.71, 28.89, 29.16, 29.20, 29.23, 29.26, 29.34, 29.63, 30.20, 31.16, 31.38, 31.69, 31.74, 34.28, 34.49, 34.59, 34.97, 37.64, 40.88, 43.33, 45.00, 45.83, 47.74, 47.94, 70.60, 75.35, 75.73, 116.29 (q, J=289 Hz, CF$_3$), 129.89, 132.64, 136.48, 164.44, 170.16, 170.38, 172.65, 179.91 (q, J=36 Hz, COCF$_3$); $^{19}$F NMR (282 MHz, CDCl$_3$) 120.34; IR (film) $v_{max}$ 2934, 2861, 1729, 1637, 1473, 1381, 1282, 1256, 1183, 1117, 1065, 1019, 946, 762, cm$^{-1}$; LRFABMS (NBA) m/z 916.49 (M+H), 934.50 (M+H$_2$O+H), 1069.50 (M+NBA+H); HRFABMS (NBA) Calcd for $C_{53}H_{81}F_3NO_8$ (M+H); 916.5914 Found; 916.5922; HRFABMS (NBA) Calcd for $C_{53}H_{81}F_3NO_8$ (M+H$_2$O+H); 934.6019 Found; 934.6047.

Example 6

Preparation of N,N-dioctyl-3α,7α,12α-tris [(4-(trifluoroacetyl)benzoxy]-5β-cholan-24-amide A mixture of 190 mg (0.30 mmol) of the product of step 3 of example 2, 132 mg (3.00 mmol) of CaH$_2$, and 25 mg (0.08 mmol) of Bu$_4$NBr in 4 mL of toluene was stirred at rt as 1.49 g (6.30 mmol) of 4-trifluoroacetylbenzoyl chloride was added. The mixture was refluxed for 24 h, allowed to cool to rt, and filtered through ceiite. The celite was washed with 80 mL of ethyl acetate and the combined filtrate and washing were concentrated. To the residue were added 0.1 mL of water, 30 g of silica gel, and 60 mL of toluene and the mixture was stirred for 2 h. The silica gel was filtered and washed with 150 mL of ethyl acetate and the combined filtrate and washing were concentrated. The residue was dissolved in 70 mL of ether, washed twice with 70 mL of the saturated NaHCO$_3$, dried over anhydrous MgSO$_4$, and concentrated. The residue was purified by silica gel column chromatography (ethyl acetate:n-hexane=1:4) to give 230 mg (63%) of the desired compound as a waxy solid.

$C_{67}H_{82}F_9NO_{10}$; TLC (ethyl acetate:n-hexane=1:1) $R_f$, 0.39; $^1$H NMR (300 MHz, CDCl$_3$) δ 8.23–7.88 (m, 12H), 5.51 (s, 1H, 12-CH), 5.38 (s, 1H, 7-CH), 4.79 (br m, 1H, 3-CH), 3.31–3.05 (m, 4H), 2.20–0.83 (m, 63H); $^{13}$C NMR (75 MHz, CDCl$_3$) δ 12.25, 14.01, 17.80, 22.39, 22.56, 22.65, 23.00, 25.51, 26.55, 26.78, 26.93, 27.10, 27.64, 28.98, 29.09, 29.16, 29.18, 29.30, 29.66, 30.02, 31.22, 31.36, 31.65, 31.71, 34.41, 34.86, 34.94, 38.23, 40.53, 43.78, 45.56, 45.93, 47.98, 48.32, 72.63, 75.15, 116.22 (q, J=291 Hz), 116.26 (q, J=291 Hz), 129.40, 129.50, 129.80, 129.87, 129.97, 132.90, 133.17, 133.24, 136.02, 136.31, 136.33, 163.61, 164.12, 172.70, 172.92, 179.52 (q, J=36 Hz), 179.62 (q, J=36 Hz), 179.80 (q, J=36 Hz); $^{19}$F NMR (282 MHz, CDCl$_3$) δ 119.98, 120.00, 120.06; IR (film) $v_{max}$ 2927, 2861, 1729, 1624, 1473, 1289, 1216, 1190, 1150, 1117, 946, 736 cm$^{-1}$; LRFABMS (NBA) m/z 1232.6 (M+H), 1250.6 (M+H$_2$O+H), 1268.6 (M+2H$_2$O+H), 1385.8 (M+NBA+H), 1403.8 (M+NBA+H$_2$O+H), 1421.7 (M+NBA+2H$_2$O+H); HRFABMS (NBA) Calcd for $C_{67}H_{83}F_9NO_{10}$ (M+H); 1232.5873 Found; 1232.5880.

Example 7

Preparation of N,N-dioctyl-3α,12α-diacetoxy-7α-[(4-(trifluoroacetyl)benzoxy]-5β-cholan-24-amide (Step 1) Preparation of methyl 3α,12α-dihydroxy-7-oxo-5β-cholate A mixture of 5.00 g of cholic acid (12.4 mmol) and 5.00 g (59.5 mmol) of NaHCO$_3$ in 160 mL, of water was heated to 50° C. to result a clear solution and cooled to rt. To the solution was added 4.36 g (24.5 mmol) of N-bromosuccinimide over a period of 7 h with occasional stirring. The mixture was stirred at rt for 24 h and at 90° C. for 1 h. After the mixture was allowed to cool to 0° C., 5 M HCl aqueous solution was added slowly until the solution became acidic. After the obtained solid was filtered and washed with 300 mL of water, it was dissolved in 30 mL of MeOH and evaporated under reduced pressure (repeated 2 times). The pale yellow solid was dried under vacuum for 1 day to obtain the crude ketocholic acid.

The crude acid was dissolved in 36 mL (4.39 mmol) of HCl solution in MeOH (1 g/100 mL) and stirred at rt for 24 h. After the solution was concentrated, the resulting residue was purified by silica gel column chromatography (ethyl acetate:n-hexane=1:1), and the obtained solid was recrystallized in ethyl acetate:n-hexane (10 mL:15 mL) solution to give 3.18 g (62%) of the desired compound as a white solid.

$C_{25}H_{40}NO_5$; TLC (ethyl acetate:n-hexane=2:1) $R_f$, 0.19; mp 155–156° C.; $^1$H NMR (300 MHz, CDCl$_3$) δ 3.99 (s, 1H, 12-CH), 3.66 (s, 3H, 7-CH), 3.57 (br m, 1H, 3-CH), 2.88–2.79 (m, 1H), 2.50–0.68 (m, 32H); IR (CHCl$_3$) $v_{max}$ 3626, 3467 (br), 2957, 2878 1727, 1467, 1382, 1257, 1178 cm$^{-1}$.

(Step 2) Preparation of N,N-dioctyl-3α,12α-dihydroxy-7-oxo-5β-cholan-24-amide

A solution of 210 mg (0.50 mmol) of the product of step 1 and 42.3 mg (1.00 mmol) of LiOH in 10 mL of 50% aq. MeOH was stirred at rt for 4 h and concentrated to a small volume. After the resulting solution was diluted with 3 mL of water, 1 M HCl was added slowly with stirring to generate a solid. After the precipitate was filtered and washed twice with 30 mL, of water, it was dissolved in 10 mL of MeOH and concentrated under reduced pressure to obtain white solid. The crude acid was dried under vacuum for 1 day.

A solution of 199 mg (0.50 mmol) of the crude acid and 0.251 mL (1.80 mmol) of NEt$_3$ in 5 mL of THF was stirred at 0° C. as 0.140 mL (1.80 mmol) of methyl chloroformate was added. After stirring the mixture at 0° C. for 2 h, 0.302 mL (1.00 mmol) of N,N-dioctylamine was added, and the reaction mixture was stirred at 0° C. for 2 h and at rt for 3 h. After 5 mL (5.00 mmol) of 1 M NaOH was added slowly to the reaction mixture, it was stirred at rt for 17 h and concentrated. The residue was dissolved in 50 mL of ether, washed with 50 mL of brine and 3 times with 30 mL of 1 M HCl, dried over anhydrous MgSO$_4$, and concentrated. The residue was purified by silica gel column chromatography (ethyl acetate:n-hexane=1:1) to give 167 mg (53%) of the desired compound as a waxy solid.

$C_{40}H_{71}NO_4$; TLC (ethyl acetate:n-hexane=2:1) $R_f$, 0.61; $^1$H NMR (300 MHz, CDCl$_3$) δ 4.01 (s, 1H, 12-CH), 3.58 (br m, 1H, 3-CH), 3.38–3.15 (m, 4H), 2.78–2.89 (m, 1H), 2.65 (t, 1H, J=7.5 Hz), 2.44–0.67(m, 61H); IR (CHCl$_3$) $v_{max}$ 2928, 2855, 1710, 1631, 1472, 1393, 1058 cm$^{-1}$.

(Step 3) Preparation of N,N-dioctyl-3α,12α-diacetoxy-7α-hydroxy-5β-cholan-24-amide A mixture of 2.60 g (4.13 mmol) of the product of step 2, 2.87 mL (20.7 mmol) of NEt$_3$, 256 mg (2.16 mmol) of DMAP in 30 mL of CH$_2$Cl$_2$ was stirred at 0° C. as 1.94 mL (20.7 mmol) of Ac$_2$O was added. The mixture was stirred at rt for 3 h, and concentrated. The residue was dissolved in 100 mL of ether, washed with 100 mL of 1 M HCl, dried over anhydrous MgSO$_4$, and concentrated.

The obtained crude diacetate was dissolved in 30 mL, of THF/MeOH (2:1) and stirred at 0° C. as 177 mg (4.92 mmol) of NaBH$_4$ was added. The reaction mixture was stirred at rt for 30 min and concentrated under reduced pressure. After the residue was dissolved in 70 mL of ether, washed with 70 mL of the saturated $NaHCO_3$, 70 mL of water, and 50 mL of brine, the solution was dried over anhydrous $MgSO_4$ and distilled. The residue was purified by silica gel column chromatography (ethyl acetate:n-hexane=1:2) to give 2.69 g (91%) of the desired compound as a waxy solid.

$C_{44}H_{77}NO_6$; TLC (ethyl acetate:n-hexane=1:2) $R_f$, 0.20; $^1$H NMR (300 MHz, $CDCl_3$) δ 5.08 (s, 1H, 12-CH), 4.54 (br m, 1H, 3-CH), 3.86 (s, 1H, 7-CH), 3.28–3.15 (m, 4H), 2.09 (s, 3H), 2.00 (s, 3H), 2.30–0.74 (m, 63H); IR ($CHCl_3$) $v_{max}$ 2931, 2856, 1719, 1626, 1483, 1389, 1259, 1085 $cm^{-1}$.

(Step 4) Preparation of N,N-dioctyl-3α,12α-diacetoxy-7α-[(4-trifluoroacetyl)benzoxy]-5β-cholan-24-amide A mixture of 240 mg (0.34 mmol) of the product of step 3, 78 mg (1.70 mmol) of $CaH_2$ and 22 mg (0.07 mmol) of $Bu_4NBr$ in 3 mL of toluene was stirred at rt as 479 mg (2.04 mmol) of 4-trifluoroacetylbenzoyl chloride was added. The mixture was refluxed for 48 h, allowed to cool to rt, and filtered through celite. The celite was washed with 80 mL, of ethyl acetate and the combined filtrate and washing were concentrated. The residue was dissolved in 70 mL of ether, washed twice with 70 mL of the saturated $NAHCO_3$ dried over anhydrous $MgSO_4$, and concentrated. The residue was purified by silica gel column chromatography (ethyl acetate:n-hexane=1:4) to give 290 mg (93%) of the desired compound as a waxy solid.

$C_{53}H_{80}F_3NO_8$; TLC (ethyl acetate:n-hexane=1:1) $R_f$, 0.66; $^1$H NMR (300 MHz, $CDCl_3$) δ 8.20 (br s, 4H), 5.24 (s, 1H, 7-CH), 5.17 (s, 1H, 12-CH), 4.56 (br m, 1H, 3-CH), 3.28–3.16 (m, 4H), 2.17 (s, 3H), 1.92 (s, 3H), 2.26–0.77 (m, 63H); $^{13}$C NMR (75 MHz, $CDCl_3$) δ 12.22, 14.08, 17.81, 21.34, 22.53, 22.62, 22.69, 22.95, 25.43, 26.82, 26.91, 27.03, 27.16, 27.76, 28.89, 29.18, 29.14, 29.23, 29.29, 29.38, 29.65, 29.69, 30.24, 31.39, 31.73, 31.78, 31.95, 34.37, 34.59, 34.97, 35.04, 38.16, 40.64, 43.35, 45.10, 45.88, 47.83, 48.00, 72.72, 73.70, 75.32, 116.38 (q, J=291 Hz), 129.97, 130.05, 132.94, 136.47, 163.92, 170.20, 170.43, 172.64, 180.00 (q, J=36 Hz); $^{19}$F NMR (282 MHz, $CDCl_3$) δ 120.28; IR (film) $v_{max}$ 2934, 2861, 1729, 1631, 1473, 1374, 1282, 1256, 1183, 1117, 1065, 1025, 755 $cm^{-1}$; LRFABMS (NBA) m/z 916.49 (M+H), 934.48 (M+$H_2$O+ H), 1069.50 (M+NBA+H); HRFABMS (NBA) Calcd for $C_{53}H_{81}F_3NO_8$ (M+H); 916.5914 Found; 916.5914; HRFABMS (NBA) Calcd for $C_{53}H_{83}F_3NO_9$ (M+$H_2$O+H); 934.6019 Found; 934.6028.

Example 8

Preparation of N,N-dioctyl-12α-acetoxy-3α, 7α-bis [(4-(trifluoroacetyl)benzoxy]-5β-cholan-24-amide (Step 1) Preparation of N,N-dioctyl-12α-acetoxy-3α, 7α-dihydroxy-5β-cholan-24-amide A solution of 765 mg (1.07 mmol) of the product of step 3 of example 7, 295 mg (2.14 mmol) of $K_2CO_3$ in 45 mL of MeOH was stirred at rt for 4 h and 1.5 mL (25.2 mmol) of acetic acid was added to the solution. After 30 min, the solution was concentrated. The residue was dissolved in 30 mL of ether, washed with 30 mL of brine and 50 mL of water, dried over anhydrous $MgSO_4$, and concentrated. The residue was purified by silica gel column chromatography (ethyl acetate:n-hexane=1:1) to give 640 mg (89%) of the desired compound as a waxy solid.

$C_{44}H_{77}NO_6$; TLC (ethyl acetate:n-hexane=1:1) $R_f$, 0.23; $^1$H NMR (300 MHz, $CDCl_3$) δ 5.09 (s, 1H, 12-CH), 3.89 (s, 1H, 7-CH), 3.47 (br m, 1H, 3-CH), 3.36–3.12 (m, 4H), 2.09 (s, 3H), 2.36–0.68 (m, 63H); IR ($CHCl_3$) $v_{max}$ 2937, 2855, 1722, 1625, 1472, 1387, 1263, 1194 $cm^{-1}$.

(Step 2) Preparation of N,N-dioctyl-12α-acetoxy-3α, 7α-bis [(4-(trifluoroacetyl)benzoxy]-5β-cholan-24-amide A mixture of 260 mg (0.39 mmol) of the product of step 1, 172 mg (3.90 mmol) of $CaH_2$ and 33 mg (0.10 mmol) of $Bu_4NBr$ in 4 mL of toluene was stirred at rt as 942 mg (3.99 mmol) of 4-(trifluoroacetyl)benzoyl chloride was added. The mixture was refluxed for 18 h, allowed to cool to rt, and filtered through celite. The celite was washed with 80 riL of ethyl acetate and the combined filtrate and washing were concentrated. To the residue were added 0.1 mL, of water, 25 g of silica gel and 50 mL of toluene and the mixture was stirred for 2 h. The silica gel was filtered and washed with 150 mL of ethyl acetate. After the combined filtrate and washing were concentrated, the residue was dissolved in 70 mL of ether, washed twice with 70 mL of the saturated $NaHCO_3$, dried over anhydrous $MgSO_4$, and concentrated. The residue was purified by silica gel column chromatography (ethyl acetate:n-hexane=1.3) to give 288 mg (69%) of the desired compound as a waxy solid.

$C_{60}H_{81}F_6NO_9$; TLC (ethyl acetate:n-hexane=1:1) $R_f$, 0.46; $^1$H NMR (300 MHz, $CDCl_3$) δ 8.24–7.75 (m, 8H), 5.30 (s, 1H, 7-CH), 5.27 (s, 1H, 12-CH), 4.85 (br m, 1H, 3-CH), 3.29–3.16 (m, 4H), 2.18 (s, 3H), 2.30–0.69 (m, 63H); $^{13}$C. NMR (75 MHz, $CDCl_3$) δ 12.22, 14.06, 17.81, 21.29, 22.50, 22.61, 22.97, 25.42, 26.75, 26.90, 27.01, 27.15, 27.75, 28.91, 29.12, 29.17, 29.22, 29.28, 29.36, 30.05, 30.20, 31.36, 31.71, 31.77, 34.38, 34.49, 34.96, 38.17, 40.64, 43.32, 45.10, 45.88, 47.84, 47.99, 72.68, 73.53, 75.30, 116.30 (q, J=288 Hz), 116.32 (q, J=291 Hz), 129.65, 129.93, 132.86, 132.94, 136.28, 136.47, 163.71, 164.24, 170.08, 172.61, 179.78 (q, J=36 Hz), 179.88 (q, J=36 Hz); $^{19}$F NMR (282 MHz, $CDCl_3$) δ 120.16, 120.20; IR (film) $v_{max}$ 2940, 2861, 1723, 1618, 1473, 1387, 1282, 1183, 1117, 1065, 1025, 946, 755 $cm^{-1}$; LRFABMS (NBA) m/z 1074.50 (M+H), 1092.54 (M+$H_2$O+H), 1110.52 (M+2$H_2$O+H), 1227.5 (M+NBA+H), 1245.5 (M+NBA+$H_2$O+H); HRFABMS (NBA) Calcd for $C_{60}H_{82}F_6NO_9$ (H+H); 1074.5894 Found; 1074.5870.

Example 9

Preparation of N,N-dioctyl-3α-acetoxy-12α-[(4-(trifluoroacetyl)benzoxy]-5β-cholan-24-amide (Step 1) Preparation of 3α,12α-diformyloxy-5β-cholic acid A mixture of 5.00 g (12.7 mmol) of deoxycholic acid and 4 drops of 70% $HClO_4$ in 20 mL of 98% formic acid was stirred at 55° C. for 1.5 h. After the mixture was allowed to cool to 40° C., $Ac_2O$ was added slowly to let the temperature of the solution maintained between 55–60° C. until a large quantity of bubbles appeared. After the solution was allowed to cool to rt and poured into 200 mL of water, the precipitate was filtered, washed with water, and dried to give 5.63 g (99%) of the desired compound as a white powder.

$C_{26}H_{40}O_6$; TLC (acetone:n-hexane=3:7) $R_f$, 0.61; m.p 197–198° C.

(Step 2) Preparation of N,N-dioctyl-3α,12α-diformyloxy-5β-cholan-24-amide

A solution of 500 mg (1.11 mmol) of the product of step 1 and 0.171 mL (1.23 mmol) of $NEt_3$ in 10 mL of $CH_2Cl_2$ was stirred at 0° C. as 0.095 mL (1.23 mmol) of methyl chloroformate was added dropwise. The solution was stirred for 1 h and 0.401 mL (1.33 mmol) of N,N-dioctylamine was added at 0° C. After 2 h, the solution was diluted with 100 mL of $CH_2Cl_2$, washed with 100 mL of water, dried over anhydrous $MgSO_4$, and concentrated. The residue was purified by silica gel column chromatography (ethyl acetate:n-hexane=1:4) to give 670 mg (90%) of the desired compound as a waxy solid.

$C_{42}H_{73}NO_5$; TLC (ethyl acetate:n-hexane=3:7) $R_f$, 0.57; IR (film) $\nu_{max}$ 2934, 2861, 2736, 1729, 1644, 1466, 1381, 1190, 762 cm$^{-1}$.

(Step 3) Preparation of N,N-dioctyl-3α,12α-dihydroxy-5β-cholan-24-amide

To a solution of 1.129 g (1.68 mmol) of the product of step 2 in 20 mL of THF was added 15 mL of 30% $K_2CO_3$ in 80% aq. methanol and the mixture was stirred at 60° C. for 72 h. After the solution was concentrated to a small volume, the residual solution was diluted with 100 mL of $CH_2Cl_2$ and washed with 40 mL of saturated $NH_4Cl$ and 100 mL, of water, dried over anhydrous MgSO4, and concentrated. The residue was purified by silica gel column chromatography (ethyl acetate:n-hexane=1:1) to give 827 mg (80%) of the desired compound as a waxy solid.

$C_{40}H_{73}NO_3$; TLC (ethyl acetate:n-hexane=2:1) $R_f$, 0.59; $^1$H NMR (300 MHz, CDCl$_3$) δ 3.97 (s, 1H, 12-CH), 3.60 (br m, 1H, 3-CH), 3.35–3.18 (m, 4H), 2.39–0.68 (m, 67H); IR (film) $\nu_{max}$ 3401 (br), 2940, 2868, 1631, 1473, 1381, 1315, 1262, 1223, 1104, 1052, 762 cm$^{-1}$.

(Step 4) Preparation of N,N-dioctyl-3α-acetoxy-12α-hydroxy-5β-cholan-24-amide

A solution of 622 mg (1.01 mmol) of the product of step 3, 0.422 mL (3.03 mmol) of NEt$_3$, and 0.286 mL (3.03 mmol) of Ac$_2$O in 10 mL of $CH_2Cl_2$ was stirred at rt for 86 h. The solution was concentrated and the residue was dissolved in 50 mL of ether. The solution was washed 3 times with 50 mL of 1 M HCl, dried over anhydrous MgSO$_4$, and concentrated. The residue was purified by silica gel column chromatography (ethyl acetate:n-hexane=1:4) to give 538 mg (81%) of the desired compound as a waxy solid.

$C_{42}H_{75}NO_4$; TLC (ethyl acetate:n-hexane=3:7) $R_f$, 0.44; $^1$H NMR (300 MHz, CDCl$_3$) δ 4.71 (br m, 1H, 3-CH), 4.00 (s, 1H, 12-CH), 3.32–3.17 (m, 4H), 2.02 (s, 3H), 2.35–0.69 (m, 66H); IR (film) $\nu_{max}$ 3454 (br), 2934, 2861, 1743, 1631, 1473, 1387, 1368, 1249, 1032 cm$^{-1}$.

(Step 5) Preparation of N,N-dioctyl-3α-acetoxy-12α-[(4-(trifluoroacetyl)benzoxy]-5β-cholan-24-amide A mixture of 210 mg (0.32 mmol) of the product of step 4, 71 mg (1.60 mmol) of CaH$_2$, and 26 mg (0.08 mmol) of Bu$_4$NBr in 3 mL of toluene was stirred at rt as 264 mg (1.12 mmol) of 4-trifluoroacetylbenzoyl chloride was added. The mixture was refluxed for 14 h, allowed to cool to rt, and filtered through celite. The celite was washed with 70 mL of ethyl acetate and the combined filtrate and washing were concentrated. To the residue were added 0.1 mL of water, 10 g of silica gel, and 30 mL of toluene, and the mixture was stirred at rt for 2 h. The silica gel was filtered and washed with 150 mL of ethyl acetate. The combined filtrate and washing were concentrated, and the residue was dissolved in 50 mL of ether, washed 3 times with 50 mL of the saturated NaHCO$_3$ and once with 50 mL, of water, dried over anhydrous MgSO4, and distilled. The residue was purified by silica qel column chromatography (ethyl acetate:n-hexane=1:4) to give 200 mg (73%) of the desired compound as a waxy solid.

$C_{51}H_{78}F_3NO_6$; TLC (ethyl acetate:toluene=3:7) $R_f$, 0.54; $^1$H NMR (300 MHz, CDCl$_3$) δ 8.28–8.20 (m, 4H), 5.42 (s, 1H, 12-CH), 4.64 (br m, 1H, 3-CH), 3.32–3.09 (m, 4H), 1.91 (s, 3H), 2.29–0.82 (m, 65H); $^{13}$C NMR (75 MHz, CDCl$_3$) δ 12.56, 14.09, 17.80, 21.28, 22.61, 22.63, 23.05, 23.52, 25.86, 25.97, 26.47, 26.81, 26.86, 27.03, 27.43, 27.76, 29.09, 29.17, 29.24, 29.26, 29.38, 29.65, 30.05, 31.36, 31.73, 31.79, 32.20, 34.02, 34.66, 34.73, 35.00, 35.70, 41.71, 45.53, 45.91, 47.92, 48.41, 50.14, 73.93, 77.71, 116.41 (q, J=291 Hz), 129.96, 130.19, 132.90, 136.57, 164.31, 170.41, 172.61, 180.00 (q, J=36 Hz); $^{19}$F NMR (282 MHz, CDCl$_3$) δ 120.31; IR (film) $\nu_{max}$ 2934, 2861, 1723, 1624, 1473, 1387, 1275, 1249, 1183, 1117, 1071, 1032, 762 cm$^{-1}$; LRFABMS (NBA) m/z 858.5 (M+H), 876.5 (M+H$_2$O+H), 1011.5 (M+NBA+H); HRFABMS (NBA) Calcd for $C_{51}H_{79}F_3NO_6$ (M+H); 858.5859 Found; 858.5839; HRFABMS (NBA) Calcd for $C_{51}H_{81}F_3NO_6$ (M+H$_2$O+H); 876.5964 Found; 876.5983.

Example 10

Preparation of N,N-dioctyl-12α-acetoxy- 3α-[(4-(trifluoroacetyl)benzoxy]-5β-cholan-24-amide (Step 1) Preparation of N,N-dioctyl-3α,12α-diacetoxy-5β-cholan-24-amide A solution of 635 mg (1.03 mmol) of the product of step 3 of example 9, 0.12 mL (5.15 mmol) of NEt$_3$, 63 mg (0.52 mmol) of DMAP, and 0.490 mL (5.15 mmol) of Ac$_2$O in 5 mL of $CH_2Cl_2$ was stirred at rt for 3.5 h and concentrated. The residue was dissolved in 100 mL of ether, washed 3 times with 50 mL of 1 M HCl, dried over anhydrous MgSO$_4$, and concentrated. The residue was purified by silica gel column chromatography (ethyl acetate:n-hexane=1:9) to give 750 mg (100%) of the desired compound as a waxy solid.

$C_{44}H_{77}NO_5$; TLC (ethyl acetate:n-hexane=3:7) $R_f$, 0.59; $^1$H NMR (300 MHz, CDCl$_3$) δ 5.07 (s, 1H, 12-CH), 4.67 (br m, 1H, 3-CH), 3.28–3.14 (m, 4H), 2.07 (s, 3H), 2.01 (s, 3H), 2.29–0.71 (m, 65H); IR (film) $\nu_{max}$ 2934, 2861, 1743, 1651, 1473, 1381, 1249, 1032 cm$^{-1}$.

(Step 2) Preparation of N,N-dioctyl-12α-acetoxy-3α-hydroxy-5β-cholan-24-amide

A solution of 558 mg (0.79 mmol) of the product of step 1 and 218 mg (1.58 mmol) of $K_2CO_3$ in 5 mL of MeOH was stirred at rt for 1.5 h, and 3 mL, of acetic acid was added to the solution. After stirring for 10 min, the solution was concentrated. The residue was dissolved in 50 mL of ether, washed with 50 mL of brine and 50 mL of water, dried over anhydrous MgSO$_4$, and concentrated under reduced pressure. The resultant was purified by silica gel column chromatography (ethyl acetate:n-hexane=1:4) to give 503 mg (97%) of the desired compound as a waxy solid.

$C_{42}H_{75}NO_5$; TLC (ethyl acetate:n-hexane=3:1) $R_f$, 0.27; $^1$H NMR (300 MHz, CDCl$_3$) δ 5.08 (s, 1H, 12-CH), 3.60 (br m, 1H, 3-CH), 3.31–3.16 (m, 4H), 2.08 (s, 3H), 2.31–073 (m, 66H); IR (film) $\nu_{max}$ 3421 (br), 2934, 2861, 1743, 1637, 1473, 1381, 1249, 1052, 762 cm$^{-1}$.

(Step 3) Preparation of N,N-dioctyl-12α-acetoxy-3α-[(4-(trifluoroacetyl)benzoxy]-5β-cholan-24-amide A mixture of 210 mg (0.32 mmol) of the product of step 2, 42 mg (0.96 mmol) of CaH$_2$, and 26 mg (0.08 mmol) of Bu$_4$NBr in 3 mL of toluene was stirred at rt as 188 mg (0.08 mmol) of 4-trifluoroacetylbenzoyl chloride was added. The mixture was refluxed for 1.5 h, allowed to cool to rt, and filtered through celite. The celite was washed with 70 mL of ethyl acetate and the combined filtrate and washing were concentrated. To the residue were added 0.1 mL of water, 10 g of silica gel, and 30 mL of toluene and the mixture was stirred at rt for 2 h. The silica gel was filtered and washed with 150 mL of ethyl acetate. The combined filtrate and washing were concentrated and the residue was dissolved in 50 mL of ether, washed 3 times with 50 mL of the saturated NaHCO$_3$ and once with 50 mL of water, dried over anhydrous MgSO$_4$, and concentrated. The residue was purified by silica gel column chromatography (ethyl acetate:n-hexane=1:9) to give 230 mg (84%) of the desired compound as a waxy solid.

$C_{51}H_{78}F_3NO_6$; TLC (ethyl acetate:toluene=3:7) $R_f$, 0.49; $^1$H NMR (300 MHz, CDCl$_3$) δ 8.22–8.12 (m, 4H), 5.12 (s, 1H, 12-CH), 4.98 (br m, 1H, 3-CH), 3.32–3.18 (m, 4H), 2.11 (s, 3H), 2.36–0.75 (m, 65H); $^{13}$C NMR (75 MHz, CDCl$_3$) δ 12.38, 14.03, 17.71, 21.30, 22.57, 23.01, 23.39, 25.64, 25.80, 26.59, 26.86, 26.99, 27.34, 27.71, 29.10, 29.14, 29.18, 29.25, 29.30, 29.60, 30.12, 31.45, 31.69, 31.74, 32.18, 34.00, 34.43, 34.62, 34.95, 35.61, 41.83, 44.97, 45.91, 47.87, 48.00, 49.39, 75.85, 75.91, 116.32 (q, J=291 Hz), 129.82, 129.89, 132.66, 136.59, 164.42, 170.31, 172.84, 179.97 (q, J=35 Hz); $^{19}$F NMR (282 MHz, CDCl$_3$) δ 120.30; IR (film) ν$_{max}$ 2934, 2861, 1723, 1624, 1479, 1387, 1282, 1256, 1183, 1117, 1065, 1025, 762 cm$^{-1}$; LRFABMS (NBA) m/z 858.4 (M+H), 876.5 (M+H$_2$O+H), 1011.5 (M+NBA+H); HRFABMS (NBA) Calcd for C$_{51}$H$_{79}$F$_3$NO$_6$ (M+H); 858.5859 Found; 858.5836; HRFABMS (NBA) Calcd for C$_{51}$H$_{81}$F$_3$NO$_7$ (M+H$_2$O+H); 876.5964 Found; 876.5918.

Example 11

Preparation of N,N-dioctyl-3α,12α-bis[(4-(trifluoroacetyl)benzoxy]-5β-cholan-24-amide A mixture of 220 mg (0.36 mmol) of the product of step 3 of example 9, 158 mg (3.57 mmol) of CaH$_2$, and 29 mg (0.09 mmol) of Bu$_4$NBr in 3 mL of toluene was stirred at rt as 1.18 g (5.00 mmol) of [4-(trifluoroacetyl)benzoyl chloride was added. The mixture was refluxed for 26 h, allowed to cool to rt, and filtered through celite. The ce-eite was washed with 100 mL of ethyl acetate and the combined filtrate and washing were concentrated. To the residue were added 0.1 mL of water, 30 g of silica gel, and 60 mL of toluene and the mixture was stirred at rt for 2 h. The silica gel was filtered and washed with 150 mL of ethyl acetate. The combined filtrate and washing were concentrated and the residue was dissolved in 50 mL of ether, washed 3 times with 50 mL of the saturated NaHCO$_2$ and once with 50 mL of water, dried over anhydrous MgSO$_4$, and concentrated. The residue was purified by silica gel column chromatography (ethyl acetate:n-hexane=3:17) to give 230 mg (63%) of the desired compound as a waxy solid.

C$_{58}$H$_{79}$F$_6$NO$_7$; TLC (ethyl acetate:toluene=3:7) R$_f$, 0.22; $^1$H NMR (300 MHz, CDCl$_3$) δ 8.30–8.18 (m, 4H), 8.10–8.05 (m, 4H), 5.44 (s, 1H, 12-CH), 4.92 (br m, 1H, 3-CH), 3.32–3.10 (m, 4H), 2.36–0.85 (m, 65H); $^{13}$C NMR (75 MHz, CDCl$_3$) δ 12.59, 14.08, 17.81, 22.60, 22.62, 23.04, 23.49, 25.88, 25.95, 26.48, 26.77, 26.85, 27.02, 27.42, 27.75, 29.08, 29.16, 29.22, 29.26, 29.37, 29.69, 30.08, 31.36, 31.72, 31.78, 32.20, 34.02, 34.63, 34.81, 35.02, 35.70, 41.74, 45.52, 45.92, 41.94, 48.43, 50.22, 75.64, 77.67, 116.34 (q, J=290 Hz), 116.33 (q, J=291 Hz), 129.70, 129.89, 129.90, 130.09, 132.77, 132.93, 136.36, 136.56, 164.23, 164.38, 172.62, 179.86 (q, J=36 Hz), 179.98 (q, J=35 Hz); $^{19}$F NMR (282 MHz, CDCl$_3$) δ 120.19, 120.23; IR (film) ν$_{max}$ 2933, 2861, 1723, 1618, 1473, 1282, 1190, 1117, 946, 736 cm$^{-1}$; LRFABMS (NBA) m/z 1016.53 (M+H), 1034.54 (M+H$_2$O+H), 1052.54 (M+2H$_2$O+H), 1169.64 (M+NBA+H), 1187.61 (M+NBA+H$_2$O+H); HRFABMS (NBA) Calcd for C$_{55}$H$_{80}$F$_6$NO$_7$ (M+H); 1016.5839 Found; 1016.5834.

Example 12

Preparation of N,N-dioctyl-3α,12α-bis[(4-(trifluoroacetyl)benzoxy]-7-oxo-5β-cholan-24-amide The reaction mixture of 235 mg (0.373 mmol) of the product of step 2 of example 7, 165.3 mg (3.73 mmol) of CaH$_2$, and 30.1 mg (0.0933 mmol) of Bu$_4$NBr in 3 mL of toluene was stirred at rt as 1.236 g (5.222 mmol) of 4-(trifluoroacetyl)benzoyl chloride was added. The mixture was refluxed for 24 h, allowed to cool to rt, and filtered through celite. The celite was washed with 100 mL of ethyl acetate and the combined filtrate and washing were concentrated. To the residue were added 0.2 mL of water, 20 g of silica gel, and 20 mL, of toluene and the mixture was stirred at rt for 2 h. The silica gel was filtered and washed with 150 mL of ethyl acetate. The combined filtrate and washing were concentrated and the residue was dissolved in 50 mL of ether, washed 3 times with 50 mL of the saturated NaHCO$_3$ and once with 50 mL of water, dried over anhydrous MgSO$_4$, and concentrated. The residue was purified by silica gel column chromatography (ethyl acetate:n-hexane=2:8) to give 240 mg (62.5%) of the desired compound as a waxy solid.

C$_{58}$H$_{77}$F$_6$NO$_8$; TLC (ethyl acetate:toluene=1:1) R$_f$, 0.49; $^2$H NMR (300 MHz, CDCl$_3$) δ 8.23–8.14 (m, 4H), 8.04–7.92 (m, 4H), 5.36 (s, 1H, 12-CH), 4.84 (br m, 1H, 3-CH), 3.32–3.10 (m, 4H), 2.55–0.86 (m, 63H); $^{19}$F NMR (282 MHz, CDCl$_3$) δ –72.33, –72.35; IR (film) ν$_{max}$ 2934, 2861, 1729, 1618, 1473, 1282, 1183, 1157, 1117, 946, 742 cm$^{-1}$; LRFABMS (NBA) m/z 1030.5 (M+H), 1048.5 (M+H$_2$O+H), 1066.5 (M+2H$_2$O+H), 1183.5 (M+NBA+H), 1201.5 (M+NBA+H$_2$O+H); HRFABMS (NBA) Calcd for C$_{58}$H$_{78}$F$_6$NO$_8$ (M+H); 1030.5632 Found; 1030.5670; HRFABMS (NBA) Calcd for C$_{58}$H$_{80}$F$_6$NO$_9$, (M+H$_2$O+H); 1048.5737 Found; 108.5690.

Example 13

Preparation of 24-(3α,12α-bis[(4-(trifluoroacetyl)benzoxy]-5β-cholanyl)dodecyl ether (Step 1) Prepration of methyl 3α,12α-dihydorxy-5β-cholan-24-oate A solution of 10.0 g (25.47 mmol) of deoxycholic acid in 100 mL of MeOH was stirred at 0° C. as 5 mL of acetyl chloride was added dropwise. The solution was left at rt for 20 h and concentrated under reduced pressure. The residue was purified by silica gel column chromatography (ethyl acetate:n-hexane=3:7) to give 8.91 g (86%) of the desired compound as a white solid.

C$_{25}$H$_{42}$O$_4$; TLC (ethyl acetate) R$_f$, 0.70; $^1$H NMR (300 MHz, CDCl$_3$) δ 3.97 (s, 1H, 12-CH), 3.65 (s, 3H), 3.60 (br m, 1H, 3-CH), 2.37–2.22 (m, 2H), 1.87–0.67 (m, 35H); IR (film) ν$_{max}$ 3408 (br), 2940, 2875, 1749, 1453, 1381, 1262 m 1170, 1052, 762 cm$^{-1}$.

(Step 2) Prepration of 3α,12α-di(methoxymethoxy)-5β-cholan-24-ol

To a solution of 1.00 g of the product of step 1 and 100 mL of dimethoxymethane in 100 mL of CH$_2$Cl$_2$ was added 0.2 mL of CF$_3$SO$_3$H and the mixture was stirred at rt for 5 h. After 0.4 mL of NH$_4$OH was added dropwise, the mixture was dried over anhydrous MGSO, and concentrated to afford crude methyl 3α,12α-di(methoxy methoxy)-5β-cholan-24-oate.

A solution of the former crude product in 20 mL of ether was added to a solution of 196.5 mg (4.919 mmol) of LiAlH, in 5 mL of ether at 0° C. After the reaction mixture was stirred at rt for 2 h and cooled to 0° C., 0.197 mL of water, 0.197 mL of 15% NaOH, and 0.591 mL, of water were added dropwise, respectively. After the precipitate was filtered and washed with 150 mL of ether, the filtrate was dried over anhydrous MgSO$_4$ and concentrated. The residue was purified by silica gel column chromatography (ethyl acetate:n-hexane=3:7) to give 1.011 g (88%) of the desired compound as a transparent colorless oil.

C$_{28}$H$_{50}$O$_5$; TLC (ethyl acetate:n-hexane=1:1) R$_f$, 0.59; $^1$H NMR (300 MHz, CDCl$_3$) δ 4.71–4.64 (m, 4H), 3.79 (s, 1H, 12-H), 3.60 (t, 2H, J=6.3 Hz), 3.49 (br m, 1H, 3-CH), 3.41

(s,3H, OCH$_3$), 3.34 (s,3H, OCH$_3$), 1.87–0.92 (m, 30H), 0.89 (s, 3H), 0.68 (s, 3H); IR (film) ν$_{max}$ 3441 (br), 2940, 2868, 1479, 1453, 1387, 1223, 1150, 1111, 1052, 927, 762 cm$^{-1}$.

(Step 3) Prepration of 24-(3α,12α-di(methoxymethoxy)-5α-cholanyl)dodecyl ether

A mixture of 466.7 mg (1 mmol) of the product of step 2, 3.6 mL (15 mmol) of dodecyl bromide, 143.1 mg (0.25 mmol) of tridodecylmethylammonium chloride, and 800 mg (10 mmol) of 50% aq. NaOH in 5 mL of toluene was stirred and heated at 75° C. for 10 days. After the mixture was allowed to cool to rt, it was extracted using 30 mL of CH$_2$Cl$_2$ and 50 mL of water. The aqueous layer separated was extracted with 30 mL, of CH$_2$Cl$_2$, and the combined organic fractions were dried over anhydrous MgSO$_4$ and concentrated. The residue was purified by silica gel column chromatography (ethyl acetate:n-hexane=1:9) to give 246 mg (39%) of the desired compound as a transparent colorless oil and 211 mg (45%) of the starting material.

C$_{40}$H$_{74}$O$_5$; TLC (ethyl acetate:n-hexane=3:7) R$_f$, 0.86; $^1$H NMR (300 MHz, CDCl$_3$) δ 4.72–4.65 (m, 4H), 3.80 (s, 1H, 12-CH), 3.52 (br m, 1H, 3-CH), 3.42–3.35 (m, 10H), 1.92–0.69 (m, 58H); IR (film) ν$_{max}$ 2934, 2855, 1473, 1453, 1381, 1150, 1117, 1052, 933 cm$^{-1}$.

(Step 4) Preparation of 24-(3α,12α-dihydroxy-5α-cholanyl)dodecyl ether

A solution of 246 mg (0.387 mmol) of the product of step 3 and 0.1 mL, of c. HCl in 10 mL of MeOH and 2 mL of CH$_2$Cl$_2$ was stirred and heated at 50° C. for 2 days. The solution was concentrated and the residue was dissolved in 50 mL, of ether, washed twice with 30 mL of water, dried over anhydrous MgSO$_4$, and concentrated. The residue was purified by silica gel column chromatography (ethyl acetate:n-hexane=2:8) to give 207 mg (98%) of the desired compound as a transparent colorless oil.

C$_{36}$H$_{66}$O$_3$; TLC (ethyl acetate:n-hexane=3:7) R$_f$, 0.27; $^1$H NMR (300 MHz, CDCl$_3$) δ 3.99 (s, 1H, 12-CH), 3.60 (br m, 1H, 3-CH), 3.41–3.34 (m, 4H), 2.05–0.68 (m, 60H); IR (film) ν$_{max}$ 3388 (br), 2927, 2861, 1473, 1381, 1124, 1045, 769 cm$^{-1}$.

(Step 5) Preparation of 24-(3α,12α-bis[(4-(trifluoroacetyl)benzoxy]-5β-cholanyl)dodecyl ether A mixture of 207 mg (0.3785 mmol) of the product of step 4, 167.7 mg (3.785 mmol) of CaH$_2$, and 30.5 mg (0.0946 mmol) of Bu$_4$NBr in 5 mL of toluene was stirred at rt as 1.254 g (5.299 mmol) of 4-(trifluoroacetyl)benzoyl chloride was added. The mixture was refluxed for 24 h, allowed to cool to rt, and filtered through celite. The celite was washed with 150 mL of ethyl acetate and the combined filtrate and washing were concentrated. To the residue were added 0.1 mL of water, 25 g of silica gel, and 30 mL of toluene and the mixture was stirred at rt tor 3 h. The silica gel was filtered and washed with 150 mL of ethyl acetate. The combined filtrate and washing were concentrated and the residue was dissolved in 50 mL of ether. After the solution was washed 4 times with 30 mL of the saturated NaHCO$_3$, twice with 30 mL of 1 M HCl, and once with 30 mL of water, it was dried over anhydrous MgSO$_4$ and concentrated. The residue was purified by silica gel column chromatography (ethyl acetate:n-hexane=1:9) to give 182 mg (51%) of the desired compound as a waxy solid.

C$_{54}$H$_{72}$F$_6$O$_7$; TLC (ethyl acetate:toluene=3:7) R$_f$, 0.35; $^1$H NMR (300 MHz, CDCl$_3$) δ 8.20–8.11 (m, 4H), 8.06–7.92 (m, 4H), 5.36 (s,lH, 12-CH), 4.84 (br m, 1H, 3-CH), 3.28–3.21 (m, 4H), 1.96–0.74 (m, 58H); IR (film) ν$_{max}$ 2927, 2861, 1729, 1611, 1473, 1420, 1381, 1328, 1289, 1216, 1190, 1157, 1117, 946, 769, 736 cm$^{-1}$; negative LRFABMS (NBA) m/z 946.5 (M$^-$), 981.4 (M$^-$+2H$_2$O–H), 1098.5 (M$^-$+NBA–H), 1099.5 (M$^-$+NBA).

Example 14

Preparation of 3α,12α-bis[(4-(trifluoroacetyl)benzoxy]-5β-cholane (Step 1) Preparation of 3α,12α-di(methoxymethoxy)-5β-cholane A mixture of 2.42 g (5.19 mmol) of the product of step 2 of example 13 and 1.98 g (10.4 mmol) of p-toluenesulfonyl chloride in 5.6 mL, (69.2 mmol) of pyridine was stirred at 0° C. for 2.5 h. After the reaction mixture was diluted with 50 mL of CH$_2$Cl$_2$, it was washed twice with 50 mL of 0.1 M HCl, 50 mL of water, and 50 mL of saturated NaCHO$_3$. The solution was dried over anhydrous MgSO$_4$ and concentrated to give crude 24-(3α,12α-dihydroxy-5β-cholanyl) tosylate.

A solution of the above crude tosylate in 4 mL of ether was added dropwise to a solution of 410 mg (10.3 mmol) of LiAlH$_4$ in 20 mL of ether at 0° C. After the mixture was stirred at rt for 1.5 h and cooled to 0° C., 0.410 mL of water, 0.410 mL of 15% NaOH, and 1.23 mL of water were added dropwise, respectively. After the precipitate was filtered and washed with 150 mL of ether, the filtrate was dried over anhydrous MgSO$_4$, and concentrated. The residue was purified by silica gel column chromatography (ethyl acetate:n-hexane=1:19) to give 1.70 g (73%) of the desired compound as a transparent colorless oil.

C$_{28}$H$_{50}$O$_4$; TLC (ethyl acetate:n-hexane=2:8) R$_f$, 0.53; $^1$H NMR (400 MHz, CDCl$_3$) δ 4.71 (d, 1H, J=6.8 Hz), 4.67 (s, 2H), 4.66 (d, 1H, J=6.8 Hz), 3.80 (t, 1H, J=2.6 Hz, 12-CH), 3.50 (m, 1H, 3-CH), 3.41 (s, 3H, OCH$_3$), 3.35 (s, 3H, OCH$_3$), 1.87–0.95 (m, 26H), 0.91 (d, 3H, J=7.6 Hz, 21-CH$_3$), 0.90 (s, 3H, 19-CH$_3$), 0.85 (t, 3H, J=7.0 Hz, 24-CH$_3$), 0.68 (s, 3H, 18-CH,); IR (film) ν$_{max}$ 2934, 2868, 1467, 1449, 1373, 1213, 1147, 1104, 1046, 918 cm$^{-1}$.

(Step 2) Preparation of 3α,12α-dihydroxy-5β-cholane

A solution of 1.7 g (3.77 mmol) of the product of step 1 and 1.5 mL of c. HCl in 60 mL of MeOH and 10 mL of CH$_2$Cl$_2$ was stirred and heated at 50° C. for 2 days. After the solution was concentrated, the residue was dissolved in 80 mL of ether, washed twice with 80 mL of water, dried over anhydrous MgSO$_4$, and concentrated. The residue was purified by silica gel column chromatography (ethyl acetate:n-hexane=2:8) to give 1.31 g (96%) of the desired compound as a transparent colorless oil.

C$_{24}$H$_{42}$O$_2$; TLC (ethyl acetate:n-hexane=3:7) R$_f$, 0.11; $^1$H NMR (400 MHz, CDCl$_1$) δ 3.99 (s, 1H, 12-CH), 3.60 (m, 1H, 3-CH), 1.88–0.93 (m, 28H), 0.95 (d, 3H, J=6.6 Hz, 21-CH$_3$), 0.90 (s, 3H, 19-CH$_3$), 0.86 (t, 3H, J=7.0 Hz, 24-CH$_3$), 0.67 (s, 3H, 18-CH$_3$); IR (film) ν$_{max}$ 3376 (br), 2936, 2867, 1467, 1449, 1378, 1215, 1089, 1040, 760 cm$^{-1}$.

(Step 3) Preparation of 3α,12α-bis[(4-(trifluoroacetyl)benzoxy]-5β-cholane

A mixture of 250 mg (0.69 mmol) of the product of step 2, 290 mg (6.9 mmol) of CaH$_2$ and 56 mg (0.17 mmol) of Bu$_4$NBr in 7 mL of toluene was stirred at rt as 2.29 g (9.7 mmol) of 4-(trifluoroacetyl)benzoyl chloride was added. The mixture was refluxed for 24 h, allowed to cool to rt, and filtered through celite. The celite was washed with 200 mL of ethyl acetate and the combined filtrate and washing were concentrated. To the residue were added 0.3 mL of water, 25 g of silica gel, and 30 mL of toluene, and the mixture was stirred for 3 h. The silica gel was filtered and washed with 200 mL of ethyl acetate. The combined filtrate and washing were concentrated and the residue was dissolved in 80 mL of ether. After the solution was washed 3 times with 80 mL of the saturated NaCHO$_3$, twice with 80 mL of 1 M HCl, and once with 80 mL of water respectively, it was dried over anhydrous MgSO$_4$ and concentrated. The residue was purified by silica gel column chromatography (ethyl acetate:n-hexane=1:9) to give 182 mg (51%) of the desired compound as a waxy solid.

$C_{42}H_{48}F_6O_6$; TLC (ethyl acetate:toluene=3:7) $R_f$, 0.45; $^1H$ NMR (300 MHz, $CDCl_3$) δ 8.31–8.21 (m, 4H), 8.11–8.02 (m, 4H), 5.45 (s,1H, 12-CH), 4.93 (br m, 1H, 3-CH), 1.98–0.80 (m,38H); IR (film) $v_{max}$ 2954, 2872, 1722, 1412, 1283, 1207, 1186, 1149, 1112, 943, 755, 732 $cm^{-1}$.

Example 15

Preparation of 3α,12α-bis[(4-(trifluoroacetyl)benzoxy]-bisnor-5β-cholanyldimethylethylene (Step 1) Preparation of 3α,12α-diacetoxy-bisnor-5α-cholanyldimethylethylene A solution of 3.00 g (7.38 mmol) of the product of step 1 of example 13 and 0.060 mL of $CF_3SO_3H$ in 200 mL of dimethoxymethane was stirred at rt for 28 h. After addition of 40 drops of c. $NH_4OH$, the reaction mixture was dried over anhydrous $MgSO_4$ and concentrated. The residue was dissolved in $CH_2Cl_2$, washed with water, dried over anhydrous $MgSO_4$, and concentrated to give crude methyl 3α,12α-di(methoxymethoxy)-5β-cholan-24-oate.

A solution of the above crude product in 20 mL of ether was added to 1.4 M methyllithium in 20 mL of ether at 0° C. After the reaction mixture was stirred at 0° C. for 1 h, the water was poured slowly to the solution. The organic fraction was dried over anhydrous $MgSO_4$ and concentrated to give crude 3α,12α-di(methoxymethoxy)-24,24-dimethyl-5β-cholan-24-ol.

A solution of the crude alcohol in 60 mL of THF and 18 mL of 2 M liCl was refluxed for 24 h. After the solution was concentrated to about 20 mL and diluted with about 50 mL of ether, it was washed with 50 mL of water, 50 mL of saturated $NaCHO_3$ $_2$ and 50 mL of brine respectively. The solution was dried over anhydrous $MgSO_4$ and concentrated to afford crude 3α,12α-dihydroxy-24,24-dimethyl-5α-cholan-24-ol.

The crude triol was dissolved in 40 mL, of acetic acid and 20 mL of $Ac_2O$ and refluxed for 13 h. After the solution was concentrated under reduced pressure, the residue was diluted with 50 mL of ether, washed with 50 mL of saturated $NaCHO_3$ and 50 mL of brine, dried over anhydrous $MgSO_4$, and concentrated. The residue was purified by silica gel column chromatography (ethyl acetate:n-hexane=1:19) to give 2.57 g (74%) of the desired compound as a waxy solid.

$C_{30}H_{48}O_4$; TLC (ethyl acetate:n-hexane=2:8) $R_f$, 0.76; $^1H$ NMR (300 MHz, $CDCl_3$) δ 5.09 (br, 2H, =CH and 12-CH), 4.70 (br m, 1H, 3-CH), 2.11 (s, 3H), 2.04 (s, 3H), 1.70 (s, 3H), 1.58 (s, 3H), 1.89–0.73 (m, 33H); IR ($CHCl_3$) $v_{max}$ 2967, 2868, 1736, 1460, 1374, 1249, 1038, 920, 742 $cm^{-1}$.

(Step 2) Preparation of 3α,12α-dihydroxy-bisnor-5β-cholanyldimethylethylene

A solution of 2.57 g (5.44 mmol) of the product of step 1 in 2 N NaOH methanolic solution was refluxed for 17 h and concentrated. After the residue was dissolved in 50 mL of water and 50 mL of $CH_2Cl_2$, acetic acid was added to make the solution be acidic. The organic fraction was separated, washed with water, dried over anhydrous $MgSO_4$, and concentrated. The residue was purified by silica gel column chromatography (ethyl acetate:n-hexane=1:2) to give 1.85 g (88%) of the desired compound as a waxy solid.

$C_{26}H_{44}O_2$; TLC (ethyl acetate:n-hexane=1:1) $R_f$, 0.46; $^1H$ NMR (300 MHz, $CDCl_3$) δ 5.10 (t, 2H), 4.64 (d, 1H), 3.98 (s, 3H), 3.58 (br m, 3H), 2.42 (br s, 3H), 2.06–0.59 (m, 32H); IR (film) $v_{max}$ 3395 (br), 2940, 2861, 1453, 1381, 1223, 1104, 1052, 762 $cm^{-1}$.

(Step 3) Preparation of 3α,12α-bis[(4-(trifluoroacetyl)benzoxy]-bisnor-5β-cholanyldimethylethylene A mixture of 180 mg (0.4632 mmol) of the product of step 2, 205.3 mg (4.632 mmol) of $CaH_2$, and 37.3 mg (0.1158 mmol) of $Bu_4NBr$ in 5 mL of toluene was stirred at rt as 1.534 g (6.4848 mmol) of 4-trifluoroacetylbenzoyl chloride was added. The mixture was refluxed for 24 h, allowed to cool to rt, and flitered through celite. The celite was washed with 150 mL of ethyl acetate and the combined filtrate and washing were concentrated. To the residue were added 0.1 mnL of water, 25 g of silica gel, and 30 mL of toluene, and the mixture was stirred for 3 h. The silica gel was filtered and washed with 150 mL of ethyl acetate. The combined filtrate and washing were concentrated and the residue was dissolved in 50 mL, of other. After the solution was washed 3 times with 50 mL, of saturated $NaCHO_3$, twice with 50 mL of 1 M HCl, and once with 50 mL of water respectively, it was dried over anhydrous $MgSO_4$ and concentrated. The residue was purified by silica gel column chromatography (ethyl is acetate:n-hexane=1:9) to give 205 mg (56%) of the desired compound as a waxy solid.

$C_{44}H_{50}F_6O_6$; TLC (ethyl acetate:toluene -3:7) $R_f$, 0.28; $^1H$ NMR (300 MHz, $CDCl_3$) δ 8.30–8.20 (m, 4H), 8.09–7.90 (m, 4H), 5.43 (s, 1H, 12-CH), 5.01 (t, 1H, J=6.0 Hz, -CH=), 4.93 (br m, 1H, 3-CH), 1.98–0.79 (m, 39H); IR (film) $v_{max}$ 2927, 2875, 1729, 1618, 1460, 1420, 1328, 1282, 1190, 1157, 1104, 953, 769 $cm^{-1}$; negative LRFABMS (NBA) m/z 788.2 ($M^-$), 824.2 ($M^-+2H_2O$), 940.3 ($M^-$+NBA–H), 941.3 ($M^-$+NBA), 977.3 ($M^-$+NBA+$2H_2O$).

Example 16

Preparation of 3α,12α-bis[(4-trifluoroacetyl)benzoxy]-bisnor-5β-cholanyldiphenylethylene (Step 1) Preparation of 3α,12α-diacetoxy-bisnor-5β-cholanyldiphenylethylene To a solution of 609 mg (1.5 mmol) of the product of step 1 of example 13 in 6 mL of benzene was added 5.0 mL (15 mmol) of 3.0 M phenylmagnesium bromide in ether and the mixture was refluxed at 90° C. for 3 h. After cooling the mixture to rt, 9 mL of c. HCl and 30 mL of ice were added, and the aqueous layer was extracted twice with 50 mL of ether. The combined organic layers were washed with 100 mL of 1 M HCl, 100 mL of water, 100 mL of 1 M NaOH and 100 mL of water respectively, dried over anhydrous $MgSO_4$, and concentrated. The residue was dissolved in 6 mL of acetic acid and 3 mL of $Ac_2O$ and refluxed for 4 h. After the solution was concentrated, the residue was dissolved in 70 mL of $CH_2Cl_2$, washed with 70 mL of saturated $NaCHO_3$ $_3$ and 70 mL of water, dried over anhydrous $MgSO_4$, and concentrated. The residue was purified by silica gel column chromatography (ethyl acetate:n-hexane=2:1) to give 650 mg (73%) of the desired compound as a waxy solid.

$C_{40}H_{52}O_4$; TLC ($CH_2Cl_2$) $R_f$, 0.18; $^1H$ NMR (300 MHz, $CDCl_3$) δ 7.39–7.15 (m, 10H), 6.08 (dd, 1H, J=8.1 and 6.6 Hz, =CH), 5.08 (s, 1H, 12-CH), 4.70 (br m, 1H, 3-CH), 2.10 (s, 3H), 2.05 (s, 3H), 2.26–0.72 (m, 33H); IR ($CHCl_3$) $v_{max}$ 3085, 3032, 2960, 1736, 1604, 1460, 1368, 1256 $cm^{-1}$.

(Step 2) Preparation of 3α,12α-dihydroxy-bisnor-5β-cholanyldiphenylethylene

A solution of 450 mg (0.154 mmol) of the product of step 1 in 10 mL of 5% $K_2CO_3$ methanolic solution was stirred and refluxed for 5 h, and 4.5 mL of acetic acid was added to the solution. The mixture was stirred for 30 min at rt, diluted with 80 mL of $CH_2Cl_2$, washed with 80 mL of saturated $NaCHO_3$ and 80 mL of water, dried over anhydrous $MgSO_4$, and concentrated. The residue was purified by silica gel column chromatography (ethyl acetate:n-hexane=3:7) to give 386 mg (100%) of the desired compound as a white solid.

$C_{36}H_{48}O_2$; TLC (ethyl acetate:n-hexane=1:1) $R_f$, 0.48; $^1$H NMR (300 MHz, CDCl$_3$) δ 7.38–7.15 (m, 10H), 6.10 (dd, 1H, J=8.1 and 6.3 Hz,=CH), 3.97 (s, 1H, 12-CH), 3.60 (br m, 1H, 3-CH), 2.28–0.67 (m, 35H); IR (CHCl$_3$) $v_{max}$ 3390 (br), 3052, 3026, 2954, 1604, 1492, 1446, 1381 cm$^{-1}$.

(Step 3) Preparation of 3α,12α-bis[(4-(trifluoroacetyl) benzoxy]-bisnor-5β-cholanyldiphenylethylene A mixture of 256.4 mg (0.5 mmol) of the product of step 2, 221.6 mg (5 mmol) of CaH$_2$, and 40.3 mg (0.125 mmol) of Bu$_4$NBr in 5 mL of toluene was stirred at rt as 1.656 g (7 mmol) of 4-(trifluoroacetyl)benzoyl chloride was added. The reaction mixture was refluxed for 24 h, allowed to cool to rt, and filtered through celite. The celite was washed with 150 mL of ethyl acetate and the combined filtrate and washing were concentrated. To the residue were added 0.1 mL of water, 25 g of silica gel, and 30 mL of toluene, and the mixture was stirred for 3 h. The silica gel was filtered and washed with 150 mL of ethyl acetate. The combined filtrate and washing were concentrated and the residue was dissolved in 50 mL of ether. After the solution was washed 4 times with 30 mL of saturated NaCHO$_3$, twice with 30 mL of 1 M HCl, and once with 30 mL of water respectively, it was dried over anhydrous MgSO$_4$ and concentrated. The residue was purified by silica gel column chromatography (ethyl acetate:n-hexane=2:8) to give 280 mg (61%) of the desired compound as a waxy solid.

$C_{54}H_{54}F_6O_6$; TLC (ethyl acetate:toluene=3:7) $R_f$, 0.25; $^1$H NMR (300 MHz, CDCl$_3$) δ 8.27–8.16 (m, 4H), 8.09–8.00 (m, 4H), 7.31–7.03 (m, 10H), 6.00 (t, 1H, J=7.2 Hz, =CH), 5.43 (s, 1H, 12-CH), 4.92 (br m, 1H, 3-CH), 2.22–0.83 (m, 43H); IR (film) $v_{max}$ 3033, 2934, 2875, 1729, 1618, 1453, 1420, 1328, 1282, 1216, 1190, 1150, 1171, 946, 762 cm$^{-1}$; negative LRFABMS (NBA) m/z 912.3 (M$^-$), 929.3 (M$^-$+H$_2$O-H), 1064.4 (M$^-$+NBA-H), 1065.4 (M$^-$+ NBA).

<Experiment 1 > Application to an Ion Sensor

The response to carbonate ion, of the ion-selective membrane electrodes that use the compounds prepared in examples 2–16 as an ionophore, was examined to confirm that the above compounds could be substituted for the conventional carbonate ion-selective ionophore, TFADB.

Carbonate-ion selective membranes which comprised a matrix, a plasticizer, the compounds of examples 2–16 and a lipophilic additive were prepared, and both conventional and solid-state ion-selective electrodes were constructed with the ion-selective membrane of the above composition, and the following examination was performed.

For the preparation of carbonate ion-selective membranes, the compounds of examples 2–16, PVC, DOA and TDMA-Cl were used as an ionophore, a matrix, a plasticizer and a lipophilic additive, respectively.

Table 1 shows the compositions of the ion-selective memoranes which used the compounds of examples 2–16.

TABLE 1

| composition membrane No. | Matrix PVC | ionophore TFADB | T1 | T2 | T3 | T4 | T5 | T6 | T7 | T8 | T9 | T10 | plasticizer DOA | liphophilic additive TDMA-Cl |
|---|---|---|---|---|---|---|---|---|---|---|---|---|---|---|
| 1  | 37.3 | 5.2 |     |     |     |     |     |     |     |     |     |     | 57.5 | 13.2 |
| 2  | 33.0 |     | 1.0 |     |     |     |     |     |     |     |     |     | 66.0 | 40.0 |
| 3  | 33.0 |     |     | 1.0 |     |     |     |     |     |     |     |     | 66.0 | 40.0 |
| 4  | 33.0 |     |     |     | 1.0 |     |     |     |     |     |     |     | 66.0 | 40.0 |
| 5  | 33.0 |     |     |     |     | 1.0 |     |     |     |     |     |     | 66.0 | 40.0 |
| 6  | 33.0 |     |     |     |     |     | 1.0 |     |     |     |     |     | 66.0 | 40.0 |
| 7  | 33.0 |     |     |     |     |     |     | 1.0 |     |     |     |     | 66.0 | 40.0 |
| 8  | 33.0 |     |     |     |     |     |     |     | 1.0 |     |     |     | 66.0 | 40.0 |
| 9  | 33.0 |     |     |     |     |     |     |     |     | 1.0 |     |     | 66.0 | 40.0 |
| 10 | 33.0 |     |     |     |     |     |     |     |     |     | 1.0 |     | 66.0 | 40.0 |
| 11 | 33.0 |     |     |     |     |     |     |     |     |     |     | 1.0 | 66.0 | 40.0 |
| 12 | 37.3 |     | 5.2 |     |     |     |     |     |     |     |     |     | 57.5 | 45.0 |
| 13 | 37.3 |     |     | 5.2 |     |     |     |     |     |     |     |     | 57.5 | 45.0 |
| 14 | 37.3 |     |     |     | 5.2 |     |     |     |     |     |     |     | 57.5 | 45.0 |
| 15 | 37.3 |     |     |     |     | 5.2 |     |     |     |     |     |     | 57.5 | 45.0 |
| 16 | 37.3 |     |     |     |     |     | 5.2 |     |     |     |     |     | 57.5 | 45.0 |
| 17 | 37.3 |     |     |     |     |     |     | 5.2 |     |     |     |     | 57.5 | 45.0 |
| 18 | 37.3 |     |     |     |     |     |     |     | 5.2 |     |     |     | 57.5 | 45.0 |
| 19 | 37.3 |     |     |     |     |     |     |     |     | 5.2 |     |     | 57.5 | 45.0 |
| 20 | 37.3 |     |     |     |     |     |     |     |     |     | 5.2 |     | 57.5 | 45.0 |
| 21 | 37.3 |     |     |     |     |     |     |     |     |     |     | 5.2 | 57.5 | 45.0 | a: wt %, b: relative mol % to an ionophore
T1–T10: compounds of examples 2–11, respectively The compositions listed in table 1 were dissolved in THF and poured into a glass ring on the glass plate and dried for 1 day to prepare conventional carbonate ion-selective membranes. The said ion-selective membranes (composition membranes) were cut in the shape of circle of diameter 5.5 mm and mounted on a conventional ion-selective electrode for the experiment. A solid-state carbonate ion-selective membrane electrode was prepared by coating thinly the casting solution dissolved in THF with a pneumatic dispenser.

The following examinations were performed to investigate the electrochemical properties of the carbonate ion-selective membranes prepared with the compositions of the table 1.

Figure 2A:
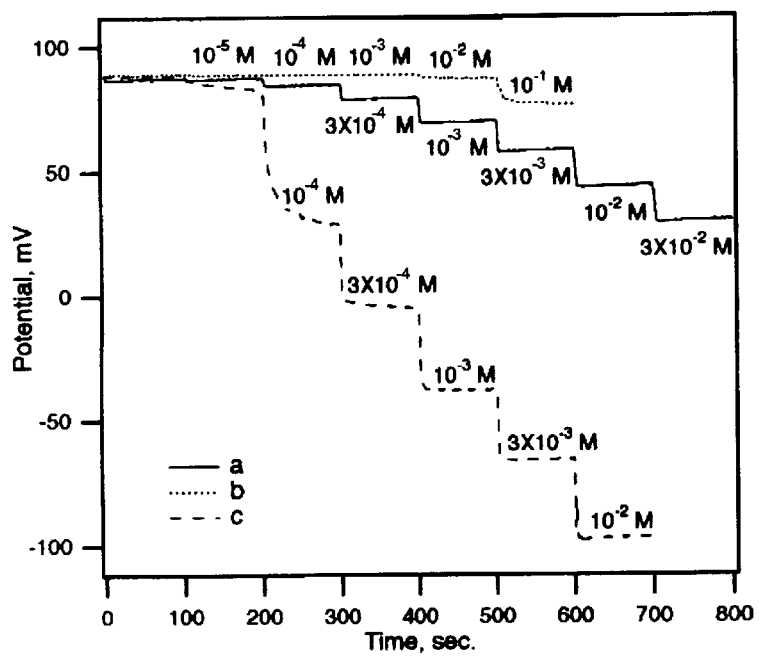
FIG. 2a depicts a graph which shows a response to carbonate ion (a), chloride ion (b) and salicylate ion (c), of a carbonate ion-selective membrane electrode prepared with TFADB as an ionophore (Hereinafter the molar concentration shown in Figures represents that of each ion.).
Figure 2B:
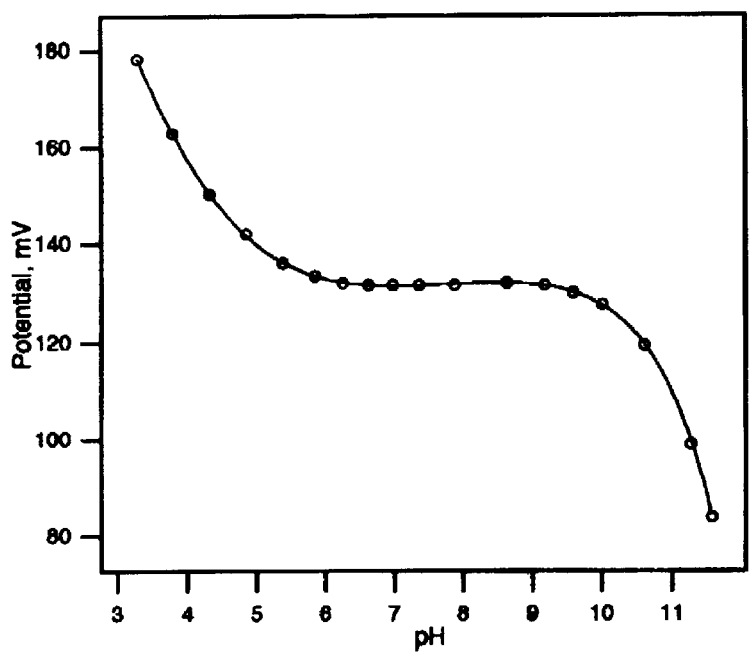
FIG. 2b depicts a graph which shows a response to the pH, of a carbonate ion-selective membrane electrode prepared with TFADB as an ionophore.

FIG. 2a depicts a graph which shows responses to carbonate ion (a), chloride ion (b) and salicylate ion (c), of a carbonate ion-selective membrane electrode prepared with the composition membrane 1 which used TFADB as an ionophore, and FIG. 2b depicts a graph which shows the response of the same electrode to the change in pH. The response to carbonate ion is good, however the response to salicylate ion, interfering ion, is better than that to carbonate ion, and so it is impossible to detect selectively carbonate ion in biological samples.

Figure 3A:
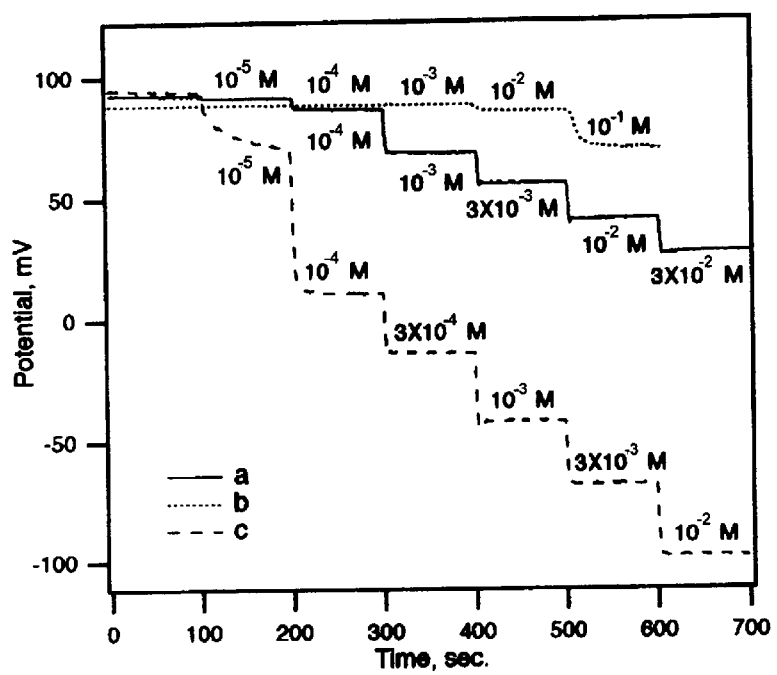
FIG. 3a depicts a graph which shows a response to carbonate ion (a), chloride ion (b) and salicylate ion (c), of the composition membrane 9 prepared with (trifluoroacetyl) phenyl (TFAP) derivative as an ionophore.
Figure 3B:
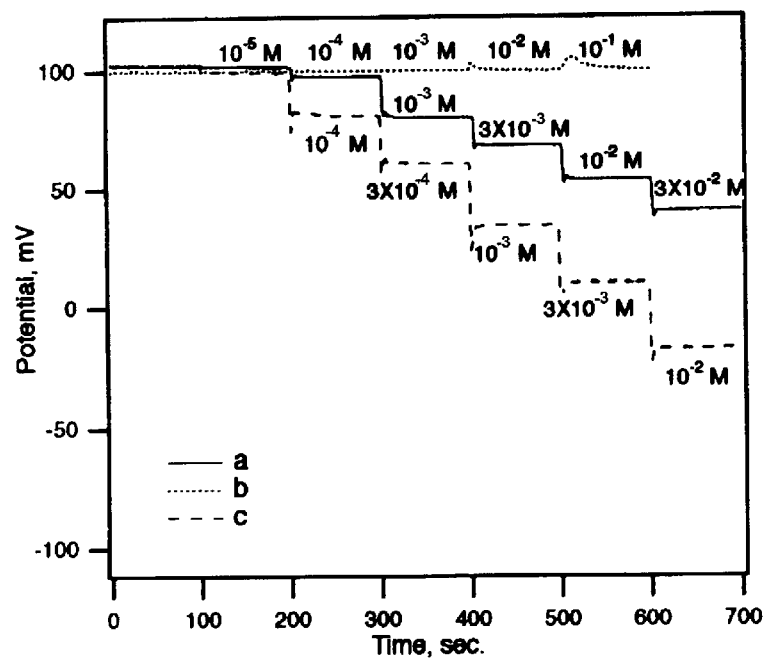
FIG. 3b depicts a graph which shows a response to carbonate ion (a), chloride ion (b) and salicylate ion (c), of the composition membrane 11 prepared with TFAP derivative as an ionophore.
Figure 3C:
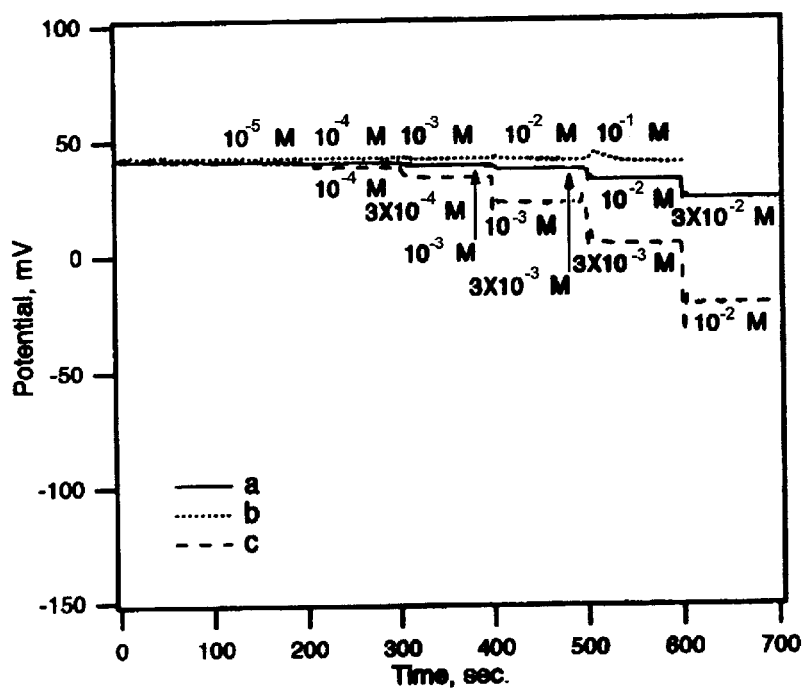
FIG. 3c depicts a graph which shows a response to carbonate ion (a), chloride ion (b) and salicylate ion (c), of the composition membrane 6 prepared with TPAP derivative as an ionophore.
Figure 3D:
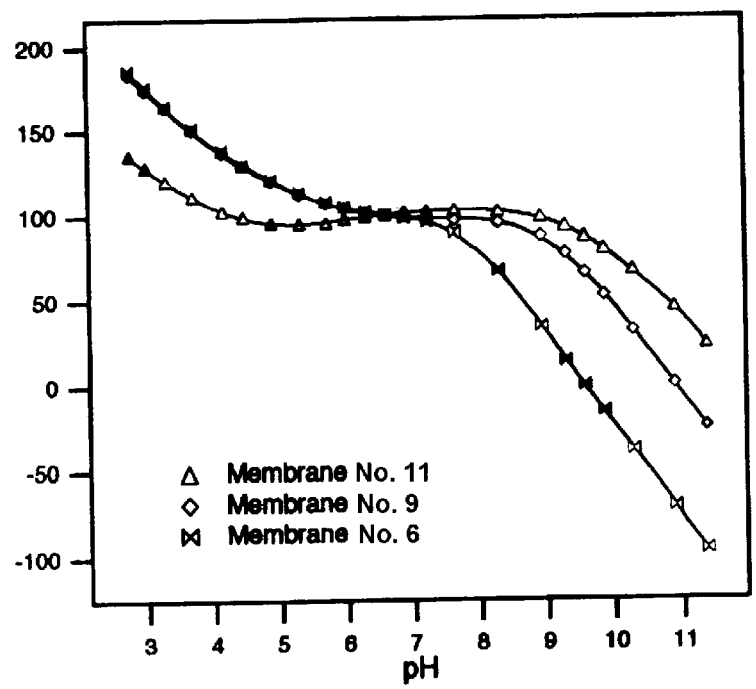
FIG. 3d depicts a graph which shows a response to the pH, of the composition membranes 9, 11 and 6 prepared with TFAP derivative as an ionophore.
Figure 4A:
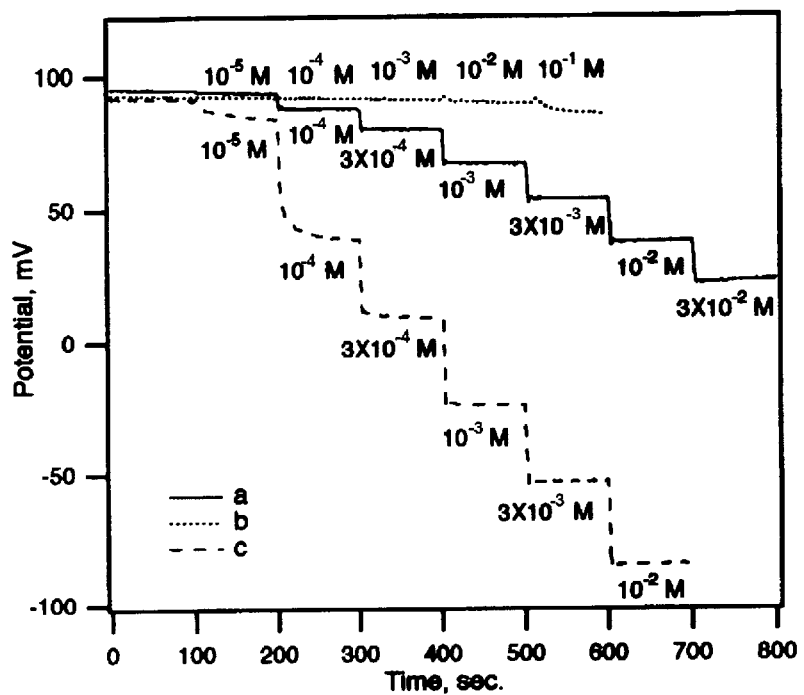
FIG. 4a depicts a graph which shows a response to carbonate ion (a), chloride ion (b) and salicylate ion (c), of the composition membrane 19 prepared with TFAP derivative as an ionophore.
Figure 4B:
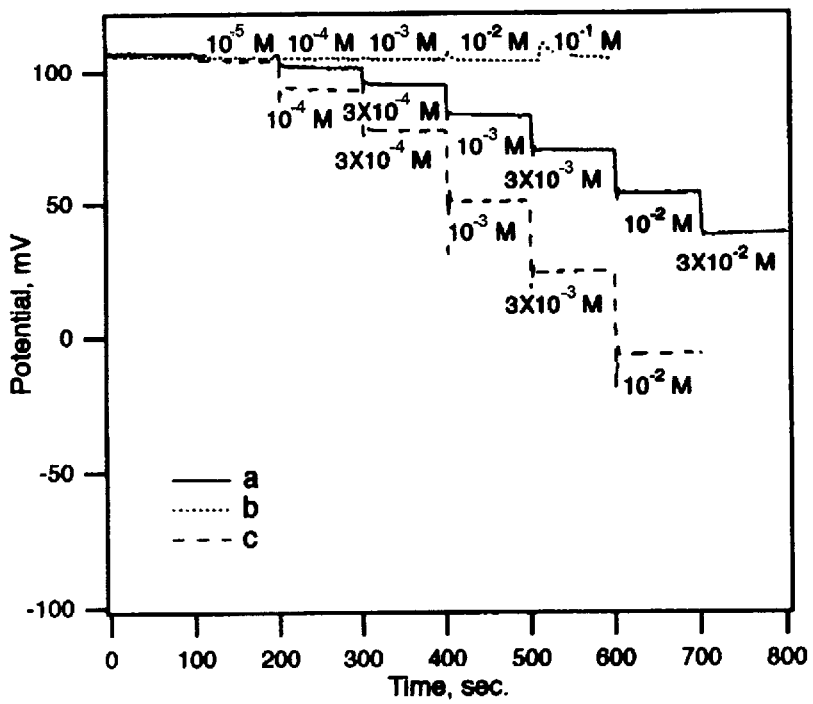
FIG. 4b depicts a graph which shows a response to carbonate ion (a), chloride ion (b) and salicylate ion (c), of the composition membrane 21 prepared with TFAP derivative as an ionophore.
Figure 4C:
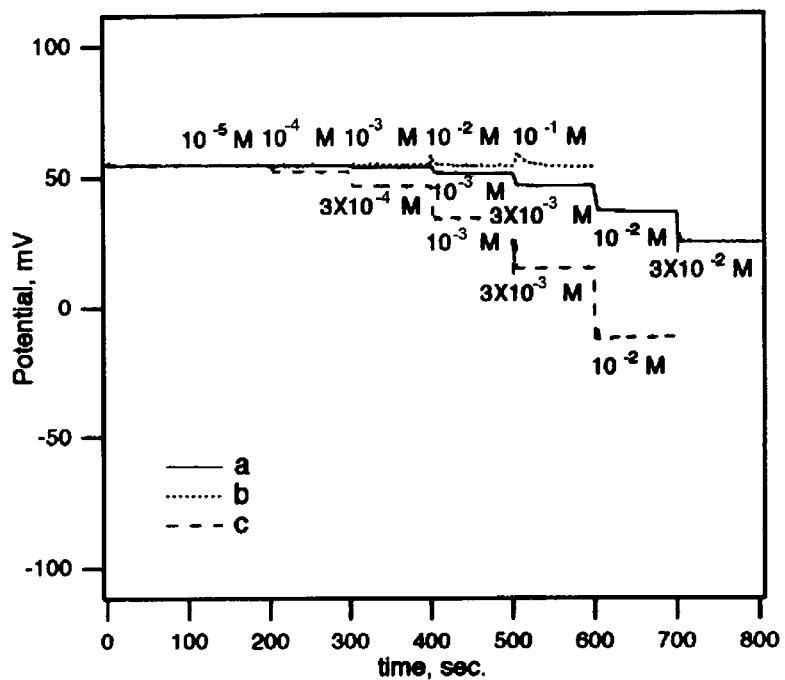
FIG. 4c depicts a graph which shows a response to carbonate ion (a), chloride ion (b) and salicylate ion (c), of the composition membrane 16 prepared with TFAP derivative as an ionophore.
Figure 4D:
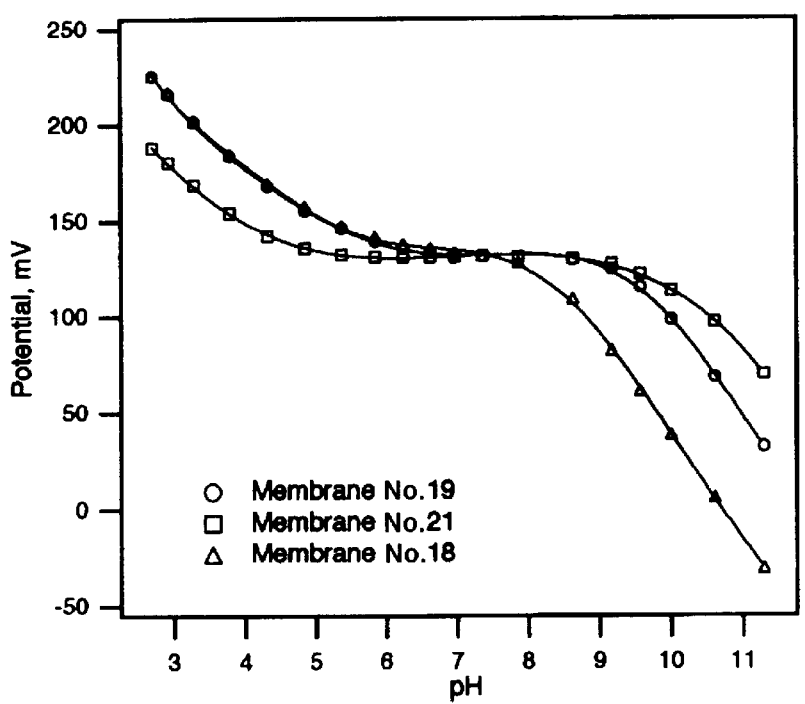
FIG. 4d depicts a graph which shows a response to the pH, of the composition membranes 19, 21 and 16 prepared with TFAP derivative as an ionophore.

FIGS. 3a–d depict the graphs which show responses to carbonate ion (a), chloride ion (b) and salicylate ion (c) of the composition membrane 9 (FIG. 3a), composition membrane 11 (FIG. 3b) and composition membrane 6 (FIG. 3c), and FIG. 3d depicts a graph which shows a response to the pH. The response to carbonate ion was similar to that of the composition membrane 1 using TFADB as an ionophore in FIG. 2a, the response of the composition membrane 9 to salicyiate ion was similar to that of the composition membrane 1, however the responses of the composition membrane 11 and 6 to salicylate ion were remarkablely decreased compared with that of the composition 1 membrane. The number of substituted TFAP groups of the derivatives used as an ionophore in the composition membranes 9, 11 and 6 are 1, 2 and 3, respectively.

As described above, it can be indirectly confirmed that a cholanic acid ring compounds having substituted TFAP groups more than two, formed 1:1 complex with carbonate ion. Also it was observed that the variation of responses to carbonate ion and salicylate ion according to the position of substituents, and the selectivity for lipophilic anions, especially salicylate ion, was evidently improved according to the number of substituents.

In FIG. 4 the compositions of a carbonate ion-selective membranes were varied, based on the result of FIG. 3, that is, the ratio of TFAP derivative was increased compared with the composition membranes of FIG. 3. As shown, the selectivity for various interfering ions including salicylate ion was much improved compared with the composition membranes of FIG. 3.

Figure 5:
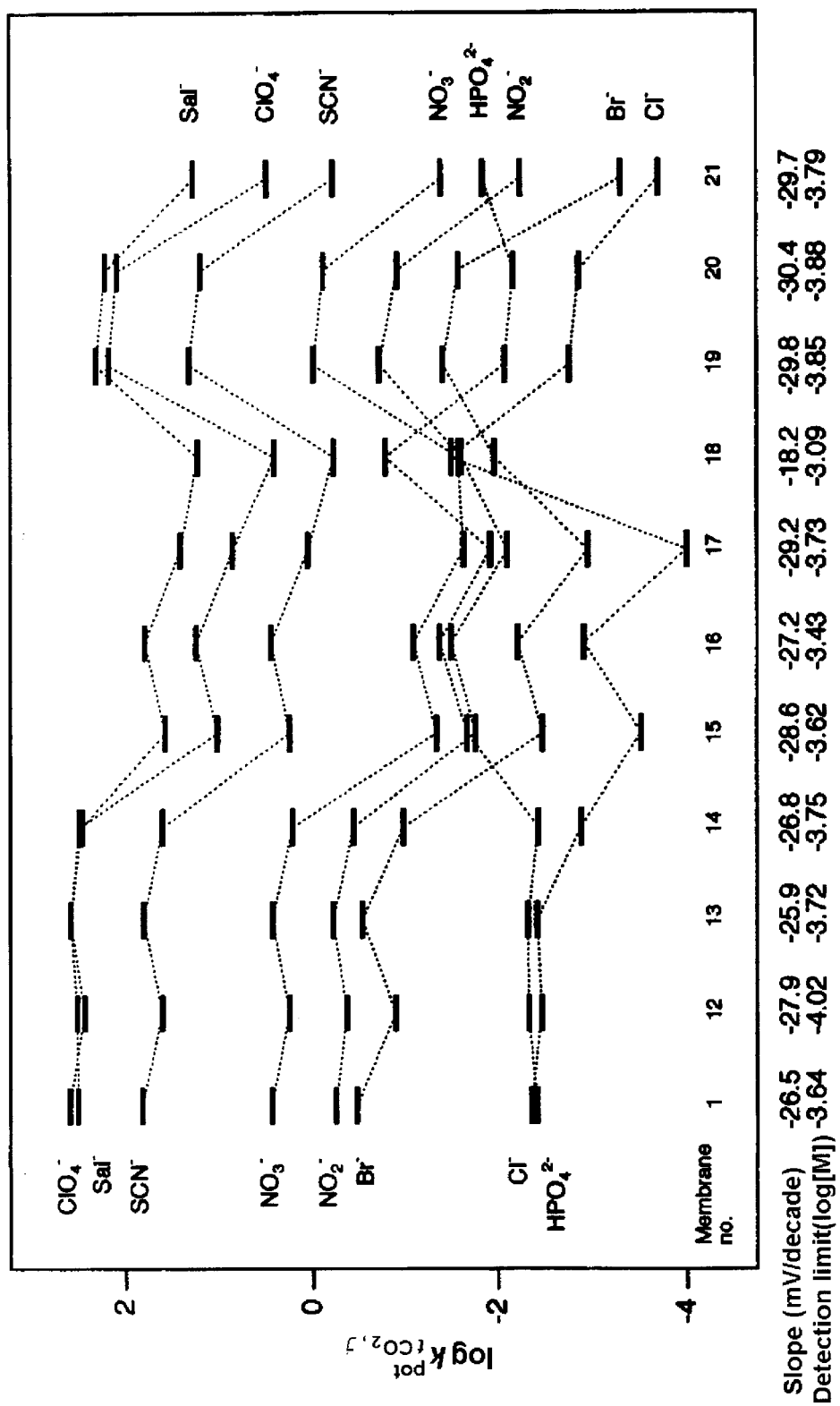
FIG. 5 depicts a graph which compares electrochemical properties (slope, selectivity parameter and detection limit) for various anions, of a carbonate ion-selective membrane electrode prepared with TFADB and TFAP derivative (compounds of examples 2–11) as ionophores.

FIG. 5 depicts a graph which compares electrochemical properties (slope, selectivity parameter and detection limit) to various anions, of the carbonate ion-selective membrane electrodes (compounds of examples 2–11) prepared with TFADB and TFAP derivatives as ionophores. The electrochemical properties of carbonate ion-selective membrane electrodes using, as an ionophore, TFAP derivatives of the present invention, were much better than those of the membrane electrode using, as an ionophore, already known TFADB, except the composition membrane 16. In particular, the selectivity over very interfering salicylate ion, of the composition membrane 12, 14, 16, 18 and 21, was evidently improved.

The compositions of an ion-selective membrane using the compounds of examples 12–16 was shown in the following table 2.

TABLE 2

| composition membrane No. | matrix PVC | ionophore T11 | T12 | T13 | T14 | T15 | plasticizer DOA | lipophilic additive TDMA-Cl |
|---|---|---|---|---|---|---|---|---|
| 22 | 37.3 | 5.2 | | | | | 57.5 | 45.0 |
| 23 | 37.3 | | 5.2 | | | | 57.5 | 45.0 |
| 24 | 37.3 | | | 5.2 | | | 57.5 | 45.0 |
| 25 | 37.3 | | | | 5.2 | | 57.5 | 45.0 |
| 26 | 37.3 | | | | | 5.2 | 57.5 | 45.0 | a: wt %, b: relative mol % to an ionophore
T11–15: compounds of examples 12–16, respectively The conventional and the solid-state ion-selective membrane electrodes using the compounds of examples 12–16 as an ionophore for carbonate ion, were prepared in the same way of the said preparation method of an electrode membrane with the composition of table 1.

The following examinations were performed to investigate the electrochemical properties of the carbonate ion-selective membranes prepared with the compositions of the table 2.

Figure 6A:
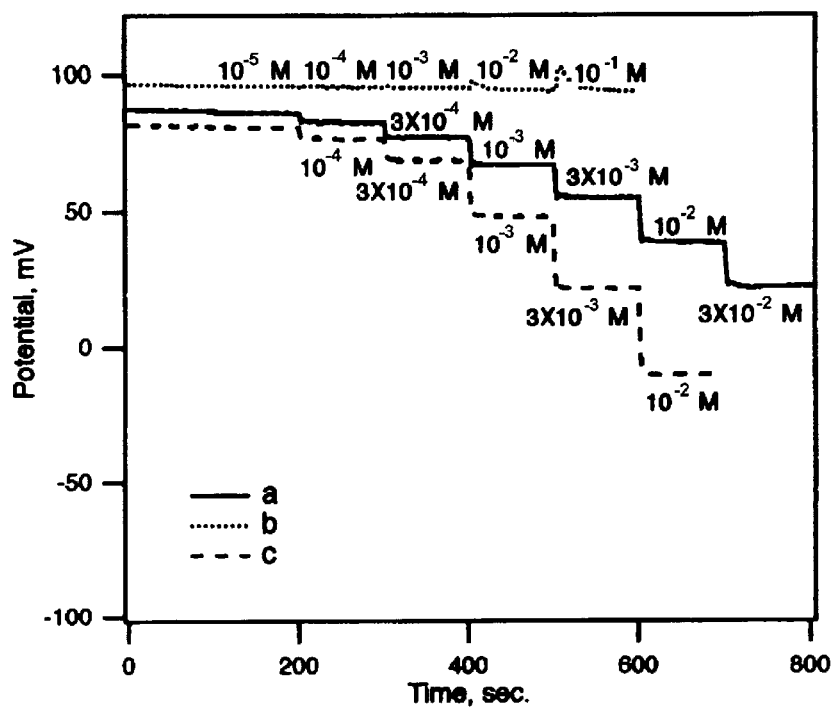
FIG. 6a depicts a graph which shows a response to carbonate ion (a), chloride ion (b) and salicylate ion (c), of the composition membrane 23 prepared with TFAP derivative as an ionophore.
Figure 6B:
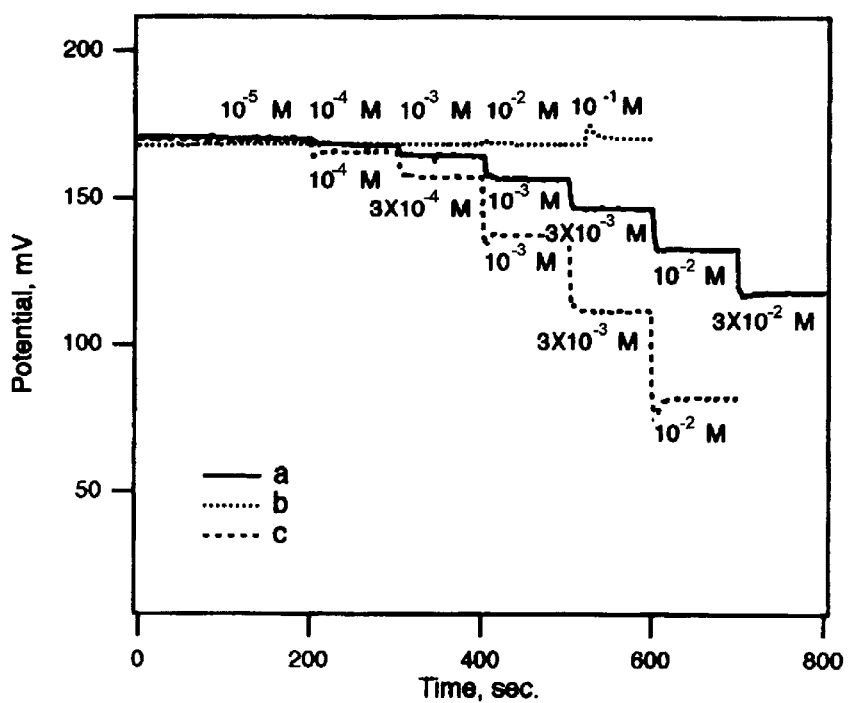
FIG. 6b depicts a graph which shows a response to carbonate ion (a), chloride ion (b) and salicylate ion (c), of the composition membrane 24 prepared with TFAP
Figure 6C:
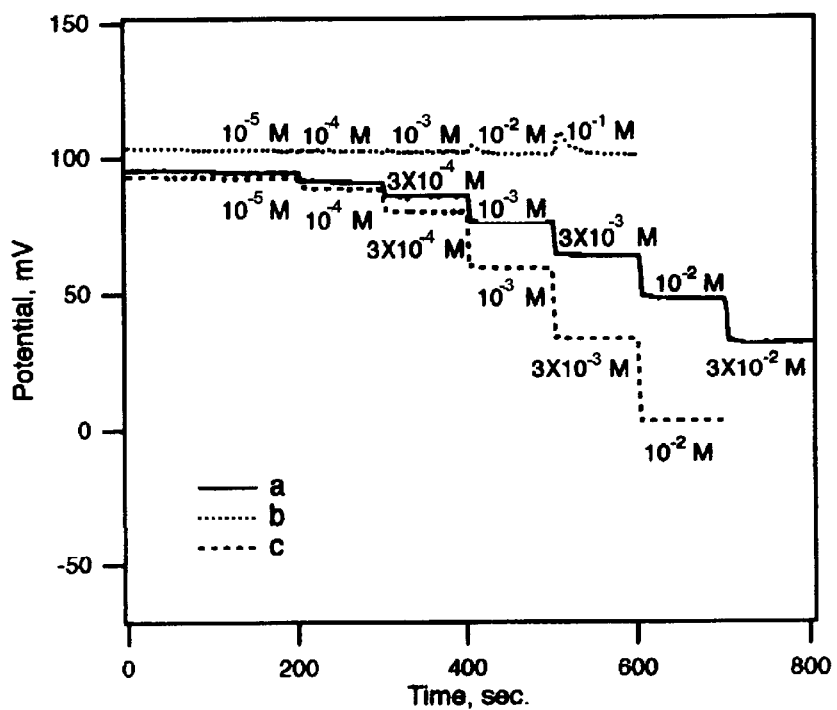
FIG. 6c depicts a graph which shows a response to carbonate ion (a), chloride ion (b) and salicylate ion (c), of the composition membrane 25 prepared with TFAP derivative as an ionophore.
Figure 6D:
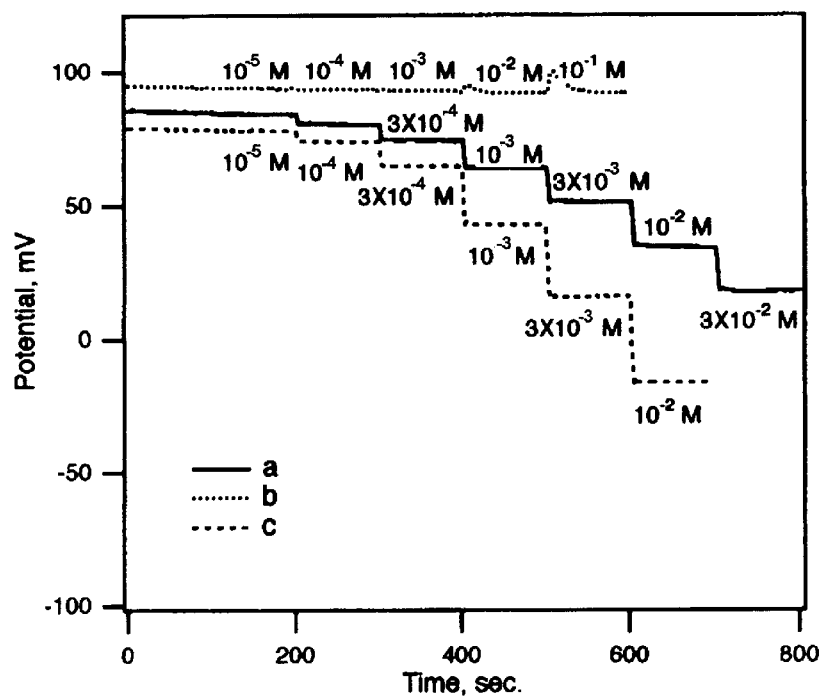
FIG. 6d depicts a graph which shows a response to carbonate ion (a), chloride ion (b) and salicylate ion (c), of the composition membrane 26 prepared with TEAP derivative as an ionophore.
Figure 6E:
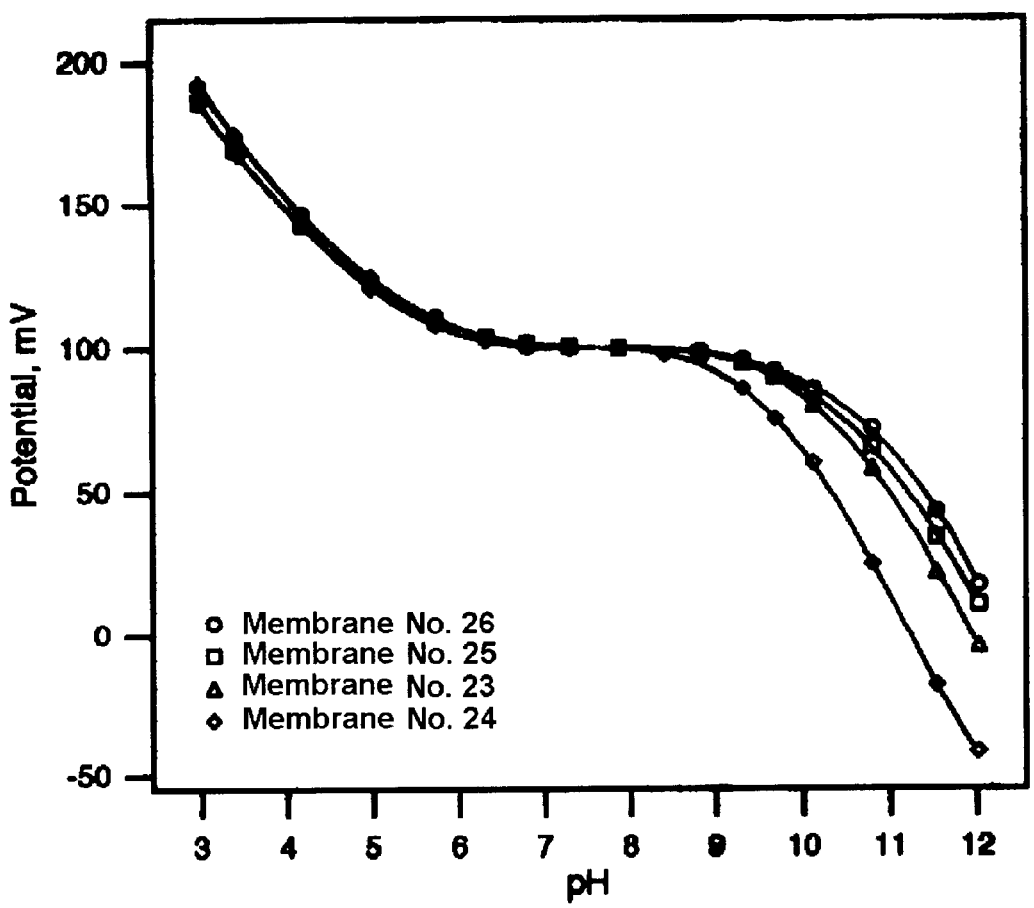
FIG. 6e depicts a graph which shows a response to the pH, of the composition membranes 23–26 prepared with TFAP derivative as an ionophore.

FIGS. 6a–d depict the graphs which show responses to carbonate ion (a), chloride ion (b) and salicylate ion (c) of the composition membranes 23 (FIG. 6a), 24 (FIG. 6b), 25 (FIG. 6c) and 26 (FIG. 6d) in a conventional electrode, which used TFAP derivatives as an ionophore, and FIG. 6e depicts a graph which shows a response to the change in pH. The response to carbonate ion was similar to those of the composition membrane 1 using TFADB as an ionophore in FIG. 2a and the composition membrane 21 showing the best electrochemical properties among the compositions of table 1, and the response to salicylate ion was evidently decreased compared with those of the composition membrane 1 and the composition membrane 21 showing the lowest response to salicylate ion among the composition membranes of table 1.

As described above, it is possible to improve the response to carbonate ion and the selectivity over interfering ions, especially salicylate ion, by transforming R functional group of a cholanic acid ring compound with two substituted TFAP groups not to dialkyl amide like as the compounds of table 1 but to alkyl, alkoxymethyl, alkoxycarbonyl, dialkylethylene or diphenylethylene.

Figure 7:
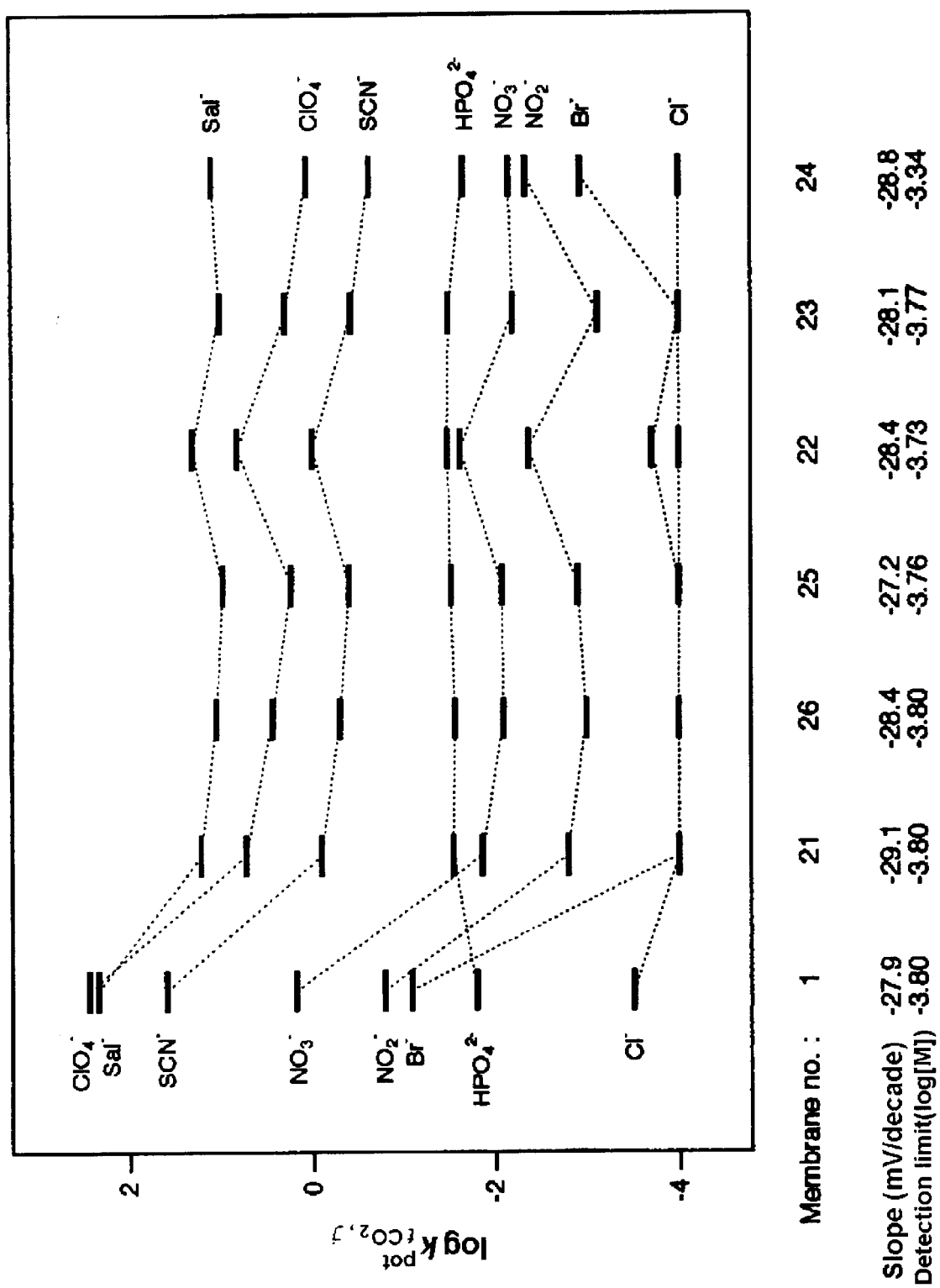
FIG. 7 depicts a graph which compares electrochemical properties (slope, selectivity parameter and detection limit) for various anions, of a carbonate ion-seioctive membrane electrode prepared with TFADB and TEAP derivative (compounds of examples 12–16) as ionophores.

FIG. 7 depicts a graph which compares the electrochemical properties (slope, selectivity parameter and detection limit) to various anions, of the carbonate ion-selective membrane electrodes (compounds of examples 12–16) prepared with TFADB and TFAP derivatives as ionophores. As represented in FIG. 7, the electrochemical properties of the carbonate ion-selective membrane electrodes using, as an ionophore, TFAP derivatives of the present invention, were much better than those of the membrane electrode using the already known TFADB (composition membrane 1) and the composition membrane 21 showing the best electrode membrane properties among the compositions of table 1 as an ionophore. In particular, the selectivity over lipophilic anoins, especially very interfering salicylate ion, of the composition membranes 22–26, was evidently improved. As a result, it will be possible to solve the interference problem of lipophilic anions, especially salicylate ion which has been a serious problem in analysis of carbonate ion of a biological sample.

<Experiment 2> Application to a Biosensor

The composition of a matrix, a TFAP derivative, a plasticizer and a lipophilic additive was dissolved in THF, poured into a glass ring on the glass plate and dried to prepare a ion-selective membrane for a urea sensor. A urease layer was introduced into the said carbonate ion-selective membrane, and the prepared membrane was attached to a conventional electrode (See FIG. 8a).

Figure 8B:
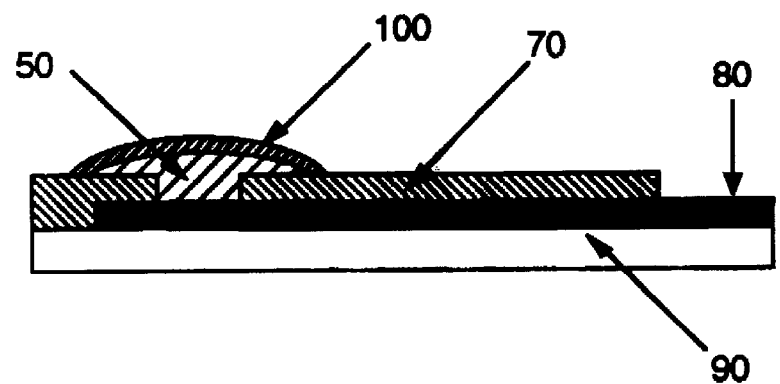
FIG. 8b depicts a schematic view of a solid-state urea sensor using, as signal transducer, a carbonate ion-selective membrane electrode prepared with TFAP derivative as an ionophore, to which an enzyme layer is introduced.

A solid-state ion-selective membrane electrode was prepared by coating thinly the composition dissolved in THF with a pneumatic dispenser, drying and introducing a urease layer (See FIG. 8b).

Figure 9A:
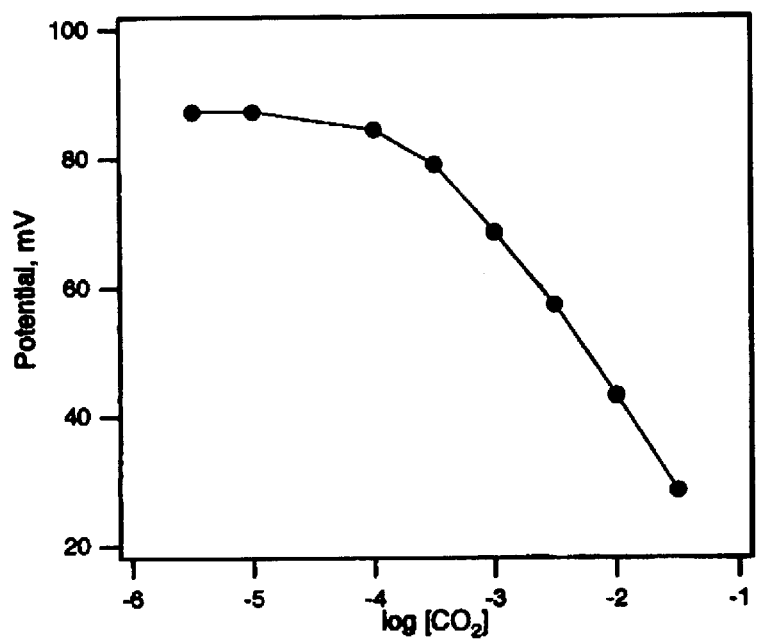
FIG. 9a depicts a graph which shows a response to carbonate ion of a conventional urea sensor using, as signal transducer, a carbonate ion-selective membrane electrode prepared with the composition membrane 21 of TFAP derivative as an ionophore.
Figure 9B:
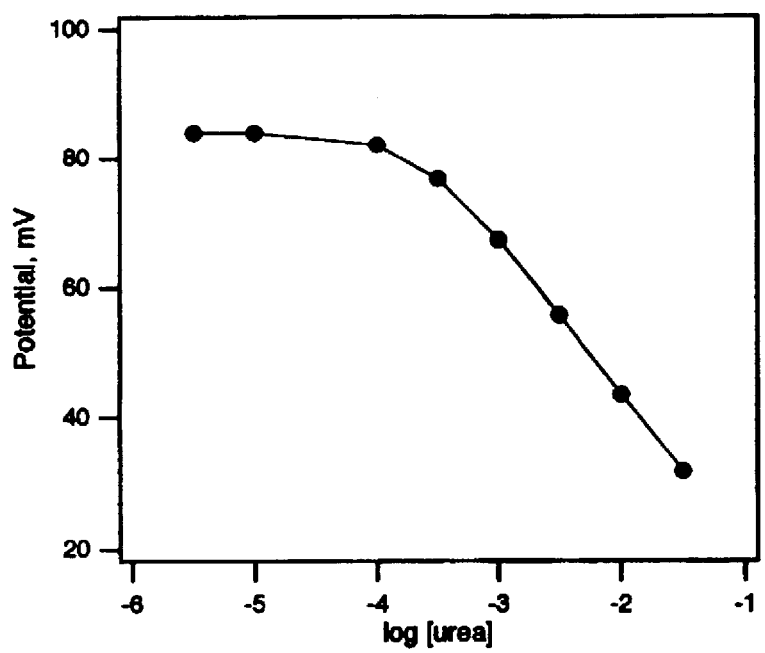
FIG. 9b depicts a graph which shows a response to carbonate ion of a solid-state urea sensor using, as signal transducer, a carbonate ion-selective membrane electrode prepared with the composition membrane 21 of TFAP derivative as an ionophore.

FIG. 9 depicts graphs which show responses to carbonate ion (FIG. 9a) and urea (FIG. 9b), of the urea sensor prepared above with the composition membrane 21 of the present invention, the carbonate ion-selective membrane used as a signal transducer showed the good response to carbonate ion despite the introduction of an enzyme layer, and the response was also good to the carbonate ion generated by an enzyme catalysis of urease and urea.

<Experiment 3> Application to a gas sensor

Figure 10:
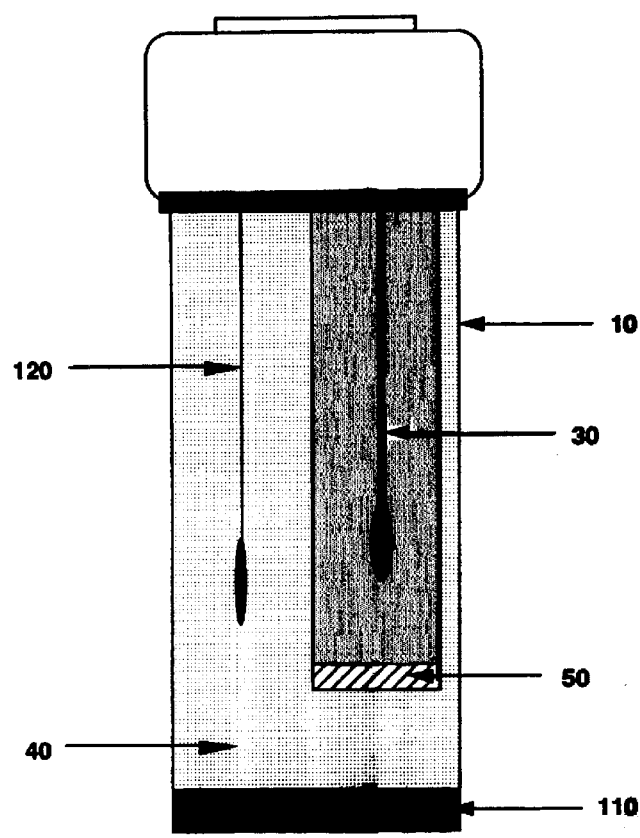
FIG. 10 depicts a schematic view of a Severinghaus-type $CO_2$ gas sensor which uses, as signal transducer, a carbonate ion-selective membrane electrode prepared with TFAP derivative as an ionophore.

The carbonate ion-selective membrane electrode whose composition was that of the table 1 and the outer reference electrode were inserted into an electrode body, an inner solution was filled and a gas permeable membrane was attached to prepare the Severinghaus-type $CO_2$ gas sensor shown in FIG. 10.

Figure 11:
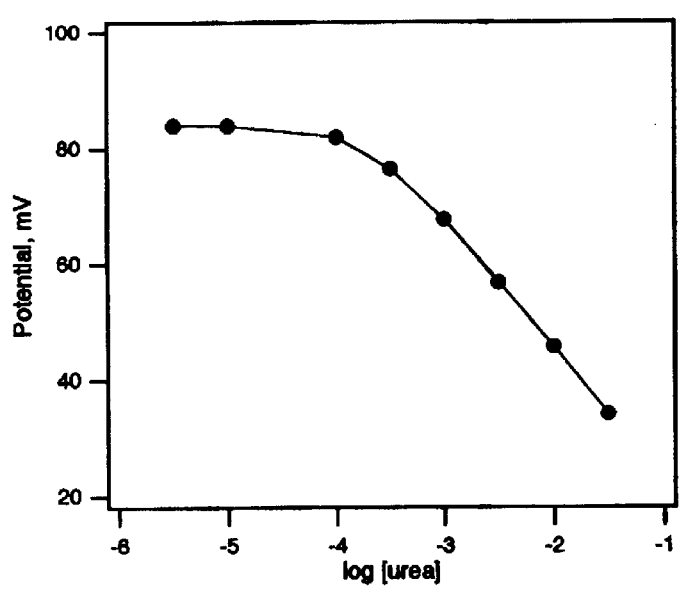
FIG. 11 depicts a graph which shows a response to $CO_2$ gas, of a $CO_2$ gas sensor which uses, as signal transducer, a carbonate ion-selective membrane electrode prepared with the composition membrane 21 of TFAP derivative as an ionophore.

FIG. 11 depicts a graph which shows response to $CO_2$ with varying the concentration thereof, of the $CO_2$ gas sensor which used the carbonate ion-selective membrane prepared with the composition membrane 21 of the present invention as a signal transducer. The carbonate ion-selective membrane used as a signal transducer, showed a good response to carbonate ion which were transformed from $CO_2$ transported across a gas permeable membrane by an inner reference solution.

What is claimed is:

1. Cholanic acid ring based 4-(trifluoroacetyl)phenyl derivatives of the following formula 1:

FORMULA 1

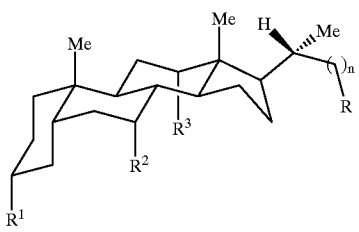

wherein, n is a value representing the length of alkyl chain and is 0–3; R represents alkyl ($C_1$–$C_{20}$), alkoxy ($C_1$–$C_{20}$) methyl, alkoxy ($C_1$–$C_{20}$) carbonyl, dialkyl ($C_1$–$C_{20}$) amide, dialkyl ($C_1$–$C_{20}$) ethylene or diphenylethylene; $R^1$ and $R^3$ represent acetoxy or 4-(trifluoroacetyl)benzoxy; and $R^2$ represents hydrogen, keto, acetoxy or 4-trifluoroacetylbenzoxy.

2. The cholanic acid ring based 4-(trifluoroacetyl)phenyl derivatives according to claim 1, wherein the compound is selected from the group comprising:

N,N-dioctyl-3α-acetoxy-7α,12α-bis[4-(trifluoroacetyl) benzoxyl]-5β-cholan-24-amide;

N,N-dioctyl-3α,7α-diacetoxy-12α-[4-(trifluoroacetyl) benzoxyl]-5β-cholan-24-amide;

N,N-dioctyl-7α-acetoxy-3α,12α-bis[4-(trifluoroacetyl) benzoxyl]-5β-cholan-24-amide;

N,N-dioctyl-7α,12α-diacetoxy-3α-[4-(trifluoroacetyl) benzoxyl]-5β-cholan-24-amide;

N,N-dioctyl-3α,7α,12α-tris[4-(trifluoroacetyl) benzoxyl]-5β-cholan-24-amide;

N,N-dioctyl-3α,12α-diacetoxy-7α-[4-(trifluoroacetyl) benzoxyl]-5β-cholan-24-amide;

N,N-dioctyl-12α-acetoxy-3α,7α-bis[4-(trifluoroacetyl) benzoxyl]-5β-cholan-24-amide;

N,N-dioctyl-3β-acetoxy-12α-[4-(trifluoroacetyl) benzoxyl]-5β-cholan-24-amide;

N,N-dioctyl-12α-acetoxy-3α-[4-(trifluoroacetyl) benzoxyl]-5β-cholan-24-amide;

N,N-dioctyl-3α,12α-bis[4-(trifluoroacetyl)benzoxyl]-5β-cholan-24-amide;

N,N-dioctyl-3α,12α-bis[4-(trifluoroacetyl)benzoxyl]-7-oxo-5β-cholan-24-amide;

24-(3α,12α-bis[4-(trifluoroacetyl)benzoxyl]-5-cholanyl) dodecyl ether;

3α,12α-bis[4-(trifluoroacetyl)benzoxyl]-5β-cholan;

3α,12α-bis[4-(trifluoroacetyl)benzoxyl]-bisnor-5β-cholanyldimethylethylene; and

3α,12α-bis[4-(trifluoroacetyl)benzoxyl]-bisnor-5β-cholanyldiphenylethylene.

3. A preparation method of cholanic acid ring based 4-(trifluoroacetyl)phenyl derivatives of claim 1, which comprises:

1) a step in which the carboxyl group of cholanic acid derivatives is converted to alkyl, alkoxymethyl, alkoxycarbonyl, dialkyl amide, dialkylethylene or diphenylethylene (step 1);

2) a step in which any one or two hydroxyl groups at the 3α,7α and 12α positions of the cholanic acid derivatives prepared in step 1 are selectively acetylated via selective acetylations, selective oxidation-reduction reactions and selective hydrolyses (step 2); and 3) a step in which the material prepared in step 1 or 2 is reacted with 4-(trifluoroacetyl)benzoyl chloride, $CaH_2$ and tetra-n-butylammonium bromide (step 3).

4. The preparation method of cholanic acid ring based 4-(trifluoroacetyl)phenyl derivatives according to claim 3, wherein the step 2 comprises the steps of 1) protecting hydroxyl groups with formyloxy groups, forming dialkylamide group by reacting with alkyl chloroformate and a base, and deprotecting formyloxy groups into hydroxyl groups;

2) reacting the cholanic acid derivatives with protected carboxyl groups with acetic anhydride ($Ac_2O$) and a base to substitute hydroxyl group into acetoxy group;

3) reacting cholanic acids with N-bromosuccinimide and $NaHCO_3$ to oxidize a 7-hydroxyl group to a keto group, acetylating the rest of hydroxyl groups, and reacting cholanic acid derivatives having keto groups with $NaBH_4$ to reduce a keto group to the original α-hydroxyl group; and 4) reacting cholanic acid derivatives protected with acetyl group with a base to hydrolyze acetoxy groups selectively to hydroxyl groups; and the step 3 comprises the step of refluxing the cholanic acid derivatives with $CaH_2$, tetra-n-butylammonium bromide, 4-(trifluoroacetyl)benzoyl chloride to substitute hydroxyl group with 4-(trifluoroacetyl) benzoxy group.

5. Compositions for host materials comprising cholanic acid ring based 4-(trifluoroacetyl)phenyl derivatives of claim 1.

6. The compositions according to claim 5, characterized by the use of cholanic acid ring based 4-(trifluoroacetyl) phenyl derivatives for the analysis of carbonate ions of environmental or biological samples.

7. The compositions according to claim 5, which is used in ion sensors, optical sensors, gas sensors, biosensors, chromatographies, photostimulated ion-binding resins, ion exchange resins and organic reactions.

8. The compositions according to claim 7, which are used for an ionophore quantifying specific ion; an ion-selective membrane acting as a signal transducer; a stationary phase separating ions or neutral organic materials; a material separating, obtaining, concentrating and removing various anions via ionic bonding; or a phase transfering agent.

9. The compositions according to claim 7, wherein the compositions for signal transducer of an ion sensor and a biosensor comprise cholanic acid ring based 4-(trifluoroacetyl)phenyl derivatives of claim 1 as an ionophore, a polymer as a matrix, a non-volatile organic solvent as a plasticizer, or comprise further a lipophilic additive, and constitutes an ion-selective membrane electrode.

10. The compositions according to claim 7, wherein the biosensor contains an enzyme layer producing carbonate ions or derivatives thereof from substrates.

11. The compositions for host materials according to claim 9, wherein the matrix is polymers selected from the group comprising poly(vinylchloride), polyurethan, silicone rubber, cellulose acetate or cellulose triacetate; the plasticizer is selected from the group comprising bis (2-ethylhexyl)adipate (DOA) bis (2-ethylhexyl) sebacate (DOS), bis (2- ethylhexyl) phthalate (DOP), bis(1-butylphenyl)adipate (BBPA) or 2-nitorphenyl octyl ether (NPOE); and the lipophilic additive is selected from the group comprising tridodecylmethylammonium chloride (TDMA-Cl) or quarternary ammonium salt.

12. The preparation method of cholanic acid ring based 4-(trifluoroacetyl)phenyl derivatives according to claim 4, wherein the alkyl group of alkyl chloroformate of 1) in step 2 is alkyl group of $C_1$–$C_5$.

13. The preparation method of cholanic acid ring based 4-(trifluoroacetyl)phenyl derivatives according to claim 4, wherein the reaction solvent of 2) in step 2 is dichloromethane ($CH_2Cl_2$).

14. The preparation method of cholanic acid ring based 4-(trifluoroacetyl)phenyl derivatives according to claim 4, wherein the reaction solvent of 3) in step 2 is methanol-THF (tetrahydrofuran) mixture.

15. The preparation method of cholanic acid ring based 4-(trifluoroacetyl)phenyl derivatives according to claim 4, wherein the reaction solvent of 4) in step 2 is methanol.

16. The preparation method of cholanic acid ring based 4-(trifluoroacetyl)phenyl derivatives according to claim 4, wherein the reaction solvent of step 3 is toluene.

17. The preparation method of cholanic acid ring based 4-(trifluoroacetyl)phenyl derivatives according to claim 4, wherein the base of 1) and 2) in step 2 is triethylamine.

18. The preparation method of cholanic acid ring based 4-(trifluoroacetyl)phenyl derivatives according to claim 4, wherein the base of 4) in step 2 is $K_2CO_3$.

* * * * *

UNITED STATES PATENT AND TRADEMARK OFFICE
CERTIFICATE OF CORRECTION

PATENT NO. : 6,177,417 B1
DATED : January 23, 2001
INVENTOR(S) : Junho Chu et al.

It is certified that error appears in the above-identified patent and that said Letters Patent is hereby corrected as shown below:

Column 8,
Line 51, "benzoxyl" should read -- benzoxy --.
Line 66, "benzoxyl" should read -- benzoxy --.

Column 9,
Line 14, "benzoxyl" should read -- benzoxy --.
Line 30, "benzoxyl" should read -- benzoxy--.
Line 45, "benzoxyl" should read -- benzoxy --.
Line 61, "benzoxyl" should read -- benzoxy --.

Column 10,
Line 14, "benzoxyl" should read -- benzoxy --.
Line 30, "benzoxyl" should read -- benzoxy --.
Line 45, "benzoxyl" should read -- benzoxy --.
Line 61, "benzoxyl" should read -- benzoxy --.

Column 11,
Line 14, "benzoxyl" should read -- benzoxy --.
Line 29, "benzoxyl" should read -- benzoxy --.
Line 43, "benzoxyl" should read -- benzoxy --.
Line 56, "benzoxyl" should read -- benzoxy --.

Column 12,
Line 16, "benzoxyl" should read -- benzoxy --.

Column 22,
Line 57, "4-trifluoroacetylbenzoyl" should read -- 4- (trifluoroacetyl)benzoyl --.

Column 24,
Line 44, "benzoxyl" should read -- benzoxy --.

Column 25,
Line 57, "4-trifluoroacetyl)benzoyl" should read -- 4-(trifluoroacetyl) benzoyl --.

Column 31,
Line 42, "4-trifluoroacetylbenzoyl" should read -- 4-(trifluoroacetyl) benzoyl --.

Column 43, claim 1,
Line 43, "4-trifluoroacetylbenzoxy" should read -- 4- (trifluoroacetyl) benzoxy --.

UNITED STATES PATENT AND TRADEMARK OFFICE
CERTIFICATE OF CORRECTION

PATENT NO.   : 6,177,417 B1
DATED         : January 23, 2001
INVENTOR(S)  : Junho Chu et al.

It is certified that error appears in the above-identified patent and that said Letters Patent is hereby corrected as shown below:

<u>Column 43, claim 2,</u>
Line 48, "benzoxyl" should read -- benzoxy --.
Line 50, "benzoxyl" should read -- benzoxy --.
Line 52, "benzoxyl" should read -- benzoxy --.
Line 54, "benzoxyl" should read -- benzoxy --.
Line 56, "benzoxyl" should read -- benzoxy --.
Line 58, "benzoxyl" should read -- benzoxy --.
Line 60, "benzoxyl" should read -- benzoxy --.
Line 61, "3β" should read -- 3d --.
Line 62, "benzoxyl" should read -- benzoxy --.
Line 64, "benzoxyl" should read -- benzoxy --.
Line 65, "benzoxyl" should read -- benzoxy --.

<u>Column 44, claim 2</u>
Line 1, "benzoxyl" should read -- benzoxy --.
Line 3, " benzoxyl]$^5$" should read -- benzoxy]$^{5\beta}$ --.
Line 5, "benzoxyl" should read -- benzoxy --.
Line 6, "benzoxyl" should read -- benzoxy --.
Line 8, "benzoxyl" should read -- benzoxy --.

Signed and Sealed this

Twenty-fifth Day of September, 2001

Attest:

NICHOLAS P. GODICI
Attesting Officer      Acting Director of the United States Patent and Trademark Office